(12) United States Patent
Oohira et al.

(10) Patent No.: US 7,662,402 B2
(45) Date of Patent: Feb. 16, 2010

(54) NITRILE COMPOUND AND ITS USE IN PEST CONTROL

(75) Inventors: Daisuke Oohira, Toyonaka (JP); Ken Otaka, Iwaki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 442 days.

(21) Appl. No.: 10/584,402

(22) PCT Filed: Dec. 22, 2004

(86) PCT No.: PCT/JP2004/019692

§ 371 (c)(1),
(2), (4) Date: Jun. 26, 2006

(87) PCT Pub. No.: WO2005/063694

PCT Pub. Date: Jul. 14, 2005

(65) Prior Publication Data

US 2007/0112068 A1    May 17, 2007

(30) Foreign Application Priority Data

Dec. 26, 2003  (JP)  ............................ 2003-431908
Feb. 13, 2004  (JP)  ............................ 2004-036230
Sep. 29, 2004  (JP)  ............................ 2004-283540

(51) Int. Cl.
*A01N 25/02* (2006.01)
*C07C 19/08* (2006.01)

(52) U.S. Cl. ...................... 424/405; 558/460

(58) Field of Classification Search ........................ None
See application file for complete search history.

(56) References Cited

U.S. PATENT DOCUMENTS 4,000,314 A    12/1976  Drabek

FOREIGN PATENT DOCUMENTS

| JP | 4-21652 | 1/1992 |
|---|---|---|
| JP | 6-116200 | 4/1994 |
| WO | 02/089579 | 11/2002 |
| WO | 02/090320 | 11/2002 |
| WO | 02/090321 | 11/2002 |
| WO | 2004/006677 | 1/2004 |
| WO | 2004/020399 | 3/2004 |

OTHER PUBLICATIONS

Key et al. "Fluorinated Organics in the Biosphere." Envrionmental Science & Technology, vol. 31 (9), 1997. pp. 2445-2554.*
Hiyama, Tamejiro. "Organofluorine Compounds: Chemistry and Applications." Springer, 2000. Esp p. 10.*
Patent Abstracts of Japan, vol. 1998, No. 06, JP10-029966, abs only.
Patent Abstracts of Japan, vol. 2003, No. 12, JP 2004-099597, abs only.

* cited by examiner

*Primary Examiner*—Kamal A Saeed
*Assistant Examiner*—Alicia L Fierro
(74) *Attorney, Agent, or Firm*—Wenderoth, Lind & Ponack, L.L.P.

(57) ABSTRACT

The present invention provides a nitrile compound represented by the formula (I): wherein R represents C1-C4 fluoroalkyl, Q represents halogen, C1-C11 alkyl optionally substituted with halogen, C2-C6 alkenyl group optionally substituted with halogen, C2-C6 alkynyl optionally substituted with halogen, C3-C7 cycloalkyl optionally substituted with halogen or (C3-C7 cycloalkyl optionally substituted with halogen) C1-C4 alkyl, which has excellent control effect against pests.

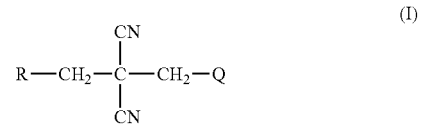

(I)

33 Claims, 3 Drawing Sheets

(a)        (b)

(a)        (b)

NITRILE COMPOUND AND ITS USE IN PEST CONTROL

TECHNICAL FIELD

The present invention relates to a nitrile compound containing a fluoroalkyl group and its use in pest control.

BACKGROUND ART

To date, some compounds for controlling pests such as insects, mites and nematodes and pest control methods using said compounds have been provided. However, those compounds can not show sufficient efficacy in some cases.

JP-A 4-21652 and JP-A 6-116200 disclose a certain nitrile compound containing a fluoroalkyl group as an intermediate for producing an active component of an antiepileptic agent.

DISCLOSURE OF INVENTION

An object of the present invention is to provide a compound having an excellent controlling effect on a pest and use of the compound in pest control.

In order to find out a compound having an excellent pest control effect, the present inventors studied intensively. As a result, the present inventors found that a nitrile compound represented by the following formula (I) had an excellent controlling activity on pests such as arthropods such as insects and mites, and nematodes, and then completed the present invention.

That is, the present invention provides a nitrile compound represented by the formula (I):

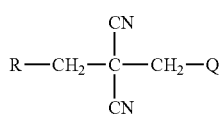

wherein R represents C1-C4 fluoroalkyl, Q represents halogen, C1-C11 alkyl optionally substituted with one or more halogen, C2-C6 alkenyl optionally substituted with one or more halogen, C2-C6 alkynyl optionally substituted with one or more halogen, C3-C7 cycloalkyl optionally substituted with one or more halogen or (C3-C7 cycloalkyl optionally substituted with one or more halogen) C1-C4 alkyl, (hereinafter, referred to as the present compound); a pesticidal composition comprising the present compound as an active ingredient, and a method of controlling a pest which comprises applying an effective amount of the present compound to said pest or a place where said pest inhabits.

MODE FOR CARRYING OUT THE INVENTION

Figure 1:
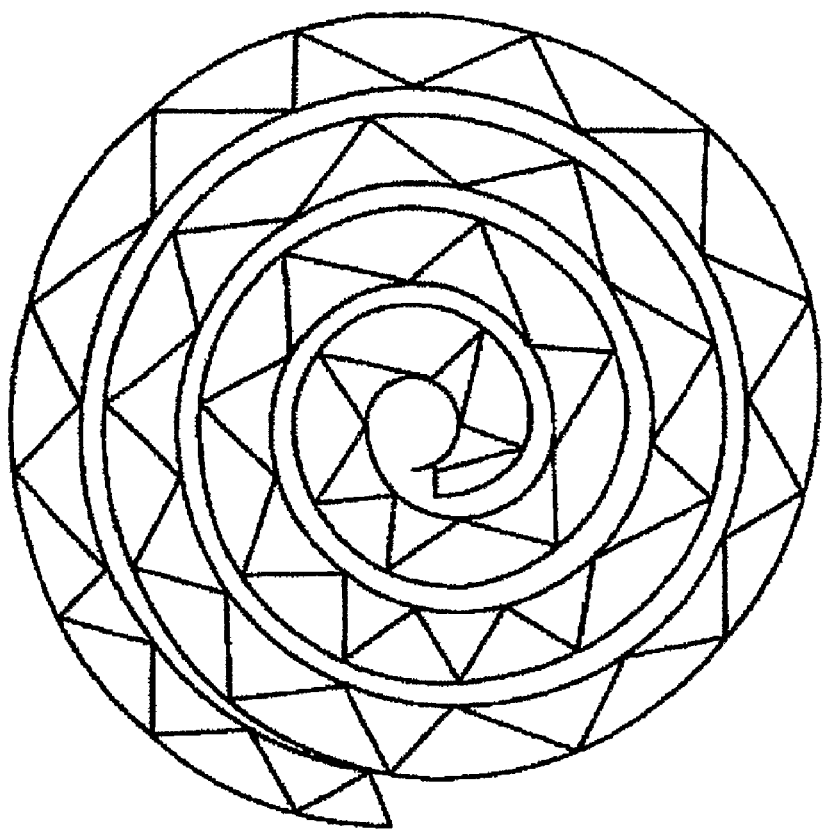
FIG. 1 is a top view of a solid carrier used in Formulation Example 9.

In the present invention, halogen represents fluorine, chlorine or bromine. The term "C1-C6 alkyl" represents alkyl whose total number of carbon atoms is 1 to 6. The term "C1-C4 fluoroalkyl" represents alkyl whose total number of carbon atoms is 1 to 4, in which one or more hydrogen atoms are substituted with a fluorine atom. The term "C3-C7" of "C3-C7 cycloalkyl" means that the total number of carbon atoms constituting the ring structure and carbon atoms of an alkyl group linked to the carbon atoms constituting said ring structure is 3 to 7.

The C1-C4 fluoroalkyl represented by R includes C1-C2 fluoroalkyl such as trifluoromethyl, 1-monofluoroethyl, 2-monofluoroethyl, 1,1-difluoroethyl, 2,2-difluoroethyl, 2,2,2-trifluoroethyl, 1,1,2,2-tetrafluoroethyl, 1,2,2,2-tetrafluoroethyl or 1,1,2,2,2-pentafluoroethyl; C3 fluoroalkyl such as 2-fluoropropyl, 3-fluoropropyl, 1,1-difluoropropyl, 2,2-difluoropropyl, 2,3-difluoropropyl, 3,3-difluoropropyl, 1,2,2-trifluoropropyl, 2,2,3-trifluoropropyl, 3,3,3-trifluoropropyl, 1,1,2,2-tetrafluoropropyl, 2,2,3,3-tetrafluoropropyl, 2,3,3,3-tetrafluoropropyl, 2,2,3,3,3-pentafluoropropyl 1,1,2,3,3,3-hexafluoropropyl or 1,1,2,2,3,3,3-heptafluoropropyl; and C4 fluoroalkyl such as 1-fluorobutyl, 2-fluorobutyl, 3-fluorobutyl, 4-fluorobutyl, 1,1-difluorobutyl, 2,2-difluorobutyl, 2,3-difluorobutyl, 2,4-difluorobutyl, 3,3-difluorobutyl, 4,4-difluorobutyl, 1,2,2-trifluorobutyl, 2,2,3-trifluorobutyl, 3,3,4-trifluorobutyl, 3,4,4-trifluorobutyl, 4,4,4-trifluorobutyl, 1,1,2,2-tetrafluorobutyl, 2,2,3,3-tetrafluorobutyl, 3,3,4,4-tetrafluorobutyl, 3,4,4,4-tetrafluorobutyl, 3,3,4,4,4-pentafluorobutyl, 2,2,3,3,4,4-hexafluorobutyl, 1,1,2,2,3,3-hexafluorobutyl 1,1,2,2,3,3,4,4-octafluorobutyl or 1,1,2,2,3,3,4,4,4-nonafluorobutyl.

The halogen represented by Q includes fluorine, chlorine and bromine.

The C1-C11 alkyl optionally substituted with one or more halogen represented by Q includes methyl, ethyl, propyl, isopropyl, butyl, isobutyl, 2-methylpropyl, 1,1-dimethylethyl, pentyl, isopentyl, neopentyl, hexyl, isohexyl, 3,3-dimethylbutyl, heptyl, octyl, nonyl, decyl, monofluoromethyl, difluoromethyl, trifluoromethyl, monochloromethyl, dichloromethyl, trichloromethyl, monobromomethyl, 1-monofluoroethyl, 2-monofluoroethyl, 1-monochloroethyl, 2-monochloroethyl, 1-monobromoethyl, 2-monobromoethyl, 1,1-difluoroethyl, 2,2-difluoroethyl, 1,2,2-trifluoroethyl, 2,2,2-trifluoroethyl, 1,1,2,2-tetrafluoroethyl, 1,1,2,2,2-pentafluoroethyl, 2-chloro-1-methylethyl, 1-fluoropropyl, 2-fluoropropyl, 3-fluoropropyl, 3-chloropropyl, 3-bromopropyl, 1,1-difluoropropyl, 2,2-difluoropropyl, 3,3-difluoropropyl, 2,3,3-trifluoropropyl, 3,3,3-trifluoropropyl, 3-chloro-3,3-difluoropropyl, 3,3-dichloro-3-fluoropropyl, 2,2,3,3-tetrafluoropropyl, 2,2,3,3,3-pentafluoropropyl, 1,1,2,3,3,3-hexafluoropropyl, 1,1,2,2,3,3,3-heptafluoropropyl, 2-chloro-3-bromo-2,3,3-trifluoropropyl, 3-bromo-2,2,3,3- tetrafluoropropyl, 2-(trifluoromethyl)-2,3,3,3-tetrafluoropropyl, 4-fluorobutyl, 4-chlorobutyl, 4-bromobutyl, 2-fluorobutyl, 2,2-difluorobutyl, 3-fluorobutyl, 3,3-difluorobutyl, 4,4-difluorobutyl, 2,2,3-trifluorobutyl, 2,2,3,3-tetrafluorobutyl, 2,2,3,4-tetrafluorobutyl, 3,3,4,4-tetrafluorobutyl, 3-chloro-3,4,4-trifluorobutyl, 4-bromo-3-chloro-3,4,4-trifluorobutyl, 3,4-dichloro-3,4,4-trifluorobutyl, 2,2,3,4,4-pentafluorobutyl, 2,2,3,4,4,4-hexafluorobutyl, 2,2,3,3,4,4-hexafluorobutyl, 3-(trifluoromethyl)-2,2,3,3,4,4,4-heptafluorobutyl, 3,4,4,4-tetrafluorobutyl, 1,1,2,2,3,3,4,4-octafluorobutyl, 1,1,2,2,3,3,4,4,4-nonafluorobutyl, 5-fluoropentyl, 5-chloropentyl, 5-bromopentyl, 2-fluoropentyl, 2-chloropentyl, 2,2-difluoropentyl, 2,3-difluoropentyl, 2,2-dichloropentyl, 2,3-dichloropentyl, 3,4-difluoropentyl, 3,4-dichloropentyl, 2,2,3-trifluoropentyl, 2,2,3,3-tetrafluoropentyl, 2,2,3,3,4-pentafluorofluoropentyl, 2,2,3,3,4,4-hexafluoropentyl, 2,2,3,3,4,4,5-heptafluoropentyl, 2,2,3,3,4,4,5,5-octafluoropentyl, 2,2,3,3,4,4,5,5,5-nonafluoropentyl, 3-fluoropentyl, 3-chloropentyl, 3,3-difluoropentyl, 3,3-dichloropentyl, 3,3,4-trifluoropentyl, 3,3,4,4-tetrafluoropentyl, 3,3,4,4,5-pentafluoropentyl, 3,4,5,5,5-pentafluoropentyl, 3,4,4,5,5-pentafluoropentyl, 3,3,4,4,5,5-hexafluoropentyl, 3,3,4,4,5,5,5-heptafluoropentyl, 4-fluoropentyl, 4,4-difluoropentyl, 4,4,5-trifluoropentyl, 4,4,5,5-tetrafluoropentyl, 4,4,5,5,5-pentafluoropentyl, 5,5-difluoropentyl, 5,5,5-trifluoropentyl, 6-fluorohexyl, 6-chlorohexyl, 6-bromohexyl, 2,2-difluorohexyl, 3-fluorohexyl, 3,3-difluorohexyl, 4-fluorohexyl, 4,4-difluorohexyl, 5,5-difluorohexyl, 2,2,3-trifluorohexyl, 2,2,3,3-hexafluorohexyl, 2,2,3,3,4-pentafluorofluorohexyl, 2,2,3,3,4,4-hexafluorohexyl, 2,2,3,3,4,4,5-heptafluorohexyl, 2,2,3,3,4,4,5,5-octafluorohexyl, 2,2,3,3,4,4,5,5,6-nonafluorohexyl, 2,2,3,3,4,4,5,5,6,6-decafluorohexyl, 2,2,3,3,4,4,5,5,6,6,6-undecafluorohexyl, 3-fluorohexyl, 1,1,2,2,3,3,4,4,5,5,6,6-dodecafluorohexyl, 3,3-difluorohexyl, 3,3,4-trifluorohexyl, 3,3,4,4-hexafluorohexyl, 3,3,4,4,5-pentafluorohexyl, 3,3,4,4,5,5-hexafluorohexyl, 3,3,4,4,5,5,6-heptafluorohexyl, 4-fluorohexyl, 4,4-difluorohexyl, 4,4,5-trifluorohexyl, 4,4,5,5-hexafluorohexyl, 4,4,5,5,6-pentafluorohexyl, 4,4,5,5,6,6-hexafluorohexyl, 4,4,5,5,6,6,6-heptafluorohexyl, 5-fluorohexyl, 5,5-difluorohexyl, 5,5,6-trifluorohexyl, 5,5,6,6-hexafluorohexyl, 5,5,6,6,6-pentafluorohexyl, 6,6-difluorohexyl and 6,6,6-trifluorohexyl.

The C2-C6 alkenyl optionally substituted with one or more halogen represented by Q includes vinyl, allyl, 1-propenyl, 2-methyl-1-propenyl, 2-methyl-2-propenyl, 3-butenyl, 2-butenyl, 1-butenyl, 3-methyl-2-butenyl, 4-pentenyl, 3-pentenyl, 2-pentenyl, 1-pentenyl, 4-methyl-3-pentenyl, 5-hexenyl, 4-hexenyl, 3-hexenyl, 2-hexenyl, 1-hexenyl, 1-fluorovinyl, 2-fluorovinyl, 1-chlorovinyl, 2-chlorovinyl, 2,2-difluorovinyl, 2,2-dichlorovinyl, 2,2-dibromovinyl, 2,3,3-trifluro-2-propenyl, 3,3,3-trifluoro-1-propenyl, 4,4-dibromo-3-butenyl, 3,4,4-trifluoro-3-butenyl, 4,4,4-trifluoro-2-butenyl, 5,5-difluoro-4-pentenyl, 4,5,5-trifluoro-4-pentenyl, 5,5,5-trifluoro-3-pentenyl, 6,6-difluoro-5-hexenyl, 5,6,6-trifluoro-5-hexenyl and 6,6,6-trifluoro-4-hexenyl.

The C2-C6 alkynyl optionally substituted with one or more halogen represented by Q includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4,4,4-trifluoro-2-butynyl and 3-chloro-2-propynyl.

The C3-C7 cycloalkyl optionally substituted with one or more halogen represented by Q includes cyclopropyl, 1-methylcyclopropyl, 2-methylcyclopropyl, 2,2-dimethylcyclopropyl, 2,3-dimethylcyclopropyl, 2,2,3-trimethylcyclopropyl, 2,2,3,3-tetramethylcyclopropyl, cyclobutyl, cyclopentyl, cyclohexyl, cycloheptyl, 1-fluorocyclopropyl, 2-fluorocyclopropyl, 2,2-difluorocyclopropyl, 2,2,3-trifluorocyclopropyl, 2,2,3,3-tetrafluorocyclopropyl, 2,2-dichlorocyclopropyl, 4-(trifluoromethyl)cyclohexyl, 3-(fluoromethyl)cyclohexyl and 2,2,3,3-tetrachlorocyclopropyl.

The (C3-C7 cycloalkyl optionally substituted with one or more halogen) C1-C4 alkyl represented by Q includes cyclopropylmethyl, 2-(cyclopropyl)ethyl, 3-(cyclopropyl)propyl, (1-methylcyclopropyl)methyl, 2-(1-methylcyclopropyl)ethyl, 3-(1-methylcyclopropyl)propyl, cyclobutylmethyl, 2-(cyclobutyl)ethyl, 3-(cyclobutyl)propyl, (2-fluorocyclopropyl)methyl, 1-(2-fluorocyclopropyl)ethyl, 2-(1-fluorocyclopropyl)ethyl, 2-(2-fluorocyclopropyl)ethyl, (2,2-difluorocyclopropyl)methyl, 2-(2,2-difluorocyclopropyl)ethyl, 1-(2,2-difluorocyclopropyl)ethyl, (2,2,3,3-tetrafluorocyclopropyl)methyl, (2,2-dichlorocyclopropyl)methyl, 2-(2,2-dichlorocyclopropyl)ethyl, cyclopentylmethyl, cyclohexylmethyl, 1-(2,2,3-trifluorocyclopropyl)ethyl, 1-(2,2,3,3-tetrafluorocyclopropyl)ethyl, 4-(cyclopropyl)butyl, 3-(cyclopropyl)butyl, 2-(cyclopropyl)butyl, 4-(1-fluorocyclopropyl)butyl, 4-(2-fluorocyclopropyl)butyl, 4-(2,2-difluorocyclopropyl)butyl, 4-(2,2,3-trifluorocyclopropyl)butyl and 4-(2,2,3,3-tetrafluorocyclopropyl)butyl.

Aspects of the present compound include, for example, the following compounds:

a nitrile compound of the formula (I) in which Q is halogen, C1-C6 alkyl optionally substituted with one or more halogen, C2-C6 alkenyl optionally substituted with one or more halogen, C2-C6 alkynyl optionally substituted with one or more halogen, C3-C7 cycloalkyl optionally substituted with one or more halogen or (C3-C7 cycloalkyl optionally substituted with one or more halogen) C1-C4 alkyl.

a nitrile compound of the formula (I) in which R is 2,2,2-trifluoroethyl;

a nitrile compound of the formula (I) in which R is 1,1,2,2-tetrafluoroethyl;

a nitrile compound of the formula (I) in which R is 1,1,2,2,3,3-hexafluoropropyl;

a nitrile compound of the formula (I) in which R is 1,1,2,2,3,3,4,4-octafluorobutyl;

a nitrile compound of the formula (I) in which R is 2,3,3,3-tetrafluoro-2-(trifluoromethyl)propyl;

a nitrile compound of the formula (I) in which R is C2-C4 fluoroalkyl having 3 to 5 fluorine atoms;

a nitrile compound of the formula (I) in which R is C3-C4 fluoroalkyl having 6 to 8 fluorine atoms;

a nitrile compound of the formula (I) in which R is trifluoromethyl;

a nitrile compound of the formula (I) in which R is C2 fluoroalkyl;

a nitrile compound of the formula (I) in which R is 2-fluoroethyl;

a nitrile compound of the formula (I) in which R is 2,2-difluoroethyl;

a nitrile compound of the formula (I) in which R is 1,2,2,2-tetrafluoroethyl;

a nitrile compound of the formula (I) in which R is 1,1,2,2,2-pentafluoroethyl;

a nitrile compound of the formula (I) in which R is C3 fluoroalkyl;

a nitrile compound of the formula (I) in which R is 2,2-difluoropropyl;

a nitrile compound of the formula (I) in which R is 3,3,3-trifluoropropyl;

a nitrile compound of the formula (I) in which R is 1,1,2,2-tetrafluoropropyl;

a nitrile compound of the formula (I) in which R is 2,2,3,3-tetrafluoropropyl;

a nitrile compound of the formula (I) in which R is 2,2,3,3,3-pentafluoropropyl;

a nitrile compound of the formula (I) in which R is C4 fluoroalkyl;

a nitrile compound of the formula (I) in which R is 2,2-difluorobutyl;

a nitrile compound of the formula (I) in which R is 1,2,2-trifluorobutyl;

a nitrile compound of the formula (I) in which R is 2,2,3-trifluorobutyl;

a nitrile compound of the formula (I) in which R is 1,1,2,2-tetrafluorobutyl;

a nitrile compound of the formula (I) in which R is 2,2,3,3-tetrafluorobutyl; a nitrile compound of the formula (I) in which R is 3,3,4,4,4-pentafluorobutyl;

a nitrile compound of the formula (I) in which R is 2,2,3,3,4,4-hexafluorobutyl;

a nitrile compound of the formula (I) in which R is 1,1,2,2,3,3-hexafluorobutyl;

a nitrile compound of the formula (I) in which R is 1,1,2,2,3,3,4,4-octafluorobutyl;

a nitrile compound of the formula (I) in which R is 1,1,2,2,3,3,4,4,4-nonafluorobutyl;

a nitrile compound of the formula (I) in which Q is halogen;

a nitrile compound of the formula (I) in which Q is bromine;

a nitrile compound of the formula (I) in which Q is chlorine;

a nitrile compound of the formula (I) in which Q is fluorine;

a nitrile compound of the formula (I) in which Q is C1-C6 alkyl optionally substituted with one or more halogen;

a nitrile compound of the formula (I) in which Q is C1 alkyl optionally substituted with one or more halogen;

a nitrile compound of the formula (I) in which Q is methyl;

a nitrile compound of the formula (I) in which Q is monofluoromethyl;

a nitrile compound of the formula (I) in which Q is difluoromethyl;

a nitrile compound of the formula (I) in which Q is trifluoromethyl;

a nitrile compound of the formula (I) in which Q is monochloromethyl;

a nitrile compound of the formula (I) in which Q is dichloromethyl;

a nitrile compound of the formula (I) in which Q is monobromomethyl;

a nitrile compound of the formula (I) in which Q is C2 alkyl optionally substituted with one or more halogen;

a nitrile compound of the formula (I) in which Q is ethyl;

a nitrile compound of the formula (I) in which Q is 2-chloro-1-methyl ethyl;

a nitrile compound of the formula (I) in which Q is 1-bromo-2,2,2-trifluoroethyl;

a nitrile compound of the formula (I) in which Q is 1-chloro-2,2,2-trifluoroethyl;

a nitrile compound of the formula (I) in which Q is 1,1-dimethylethyl;

a nitrile compound of the formula (I) in which Q is 1-monochloroethyl;

a nitrile compound of the formula (I) in which Q is 2-monochloroethyl;

a nitrile compound of the formula (I) in which Q is 2-monobromoethyl;

a nitrile compound of the formula (I) in which Q is 2-monofluoroethyl;

a nitrile compound of the formula (I) in which Q is 2,2-difluoroethyl;

a nitrile compound of the formula (I) in which Q is 2,2,2-trifluoroethyl;

a nitrile compound of the formula (I) in which Q is 1,1,2,2-tetrafluoroethyl;

a nitrile compound of the formula (I) in which Q is 1,1,2,2,2-pentafluoroethyl;

a nitrile compound of the formula (I) in which Q is C3 alkyl optionally substituted with one or more halogen;

a nitrile compound of the formula (I) in which Q is propyl;

a nitrile compound of the formula (I) in which Q is isopropyl;

a nitrile compound of the formula (I) in which Q is 3-chloropropyl;

a nitrile compound of the formula (I) in which Q is 3-chloro-2-propyl;

a nitrile compound of the formula (I) in which Q is 3-fluoropropyl;

a nitrile compound of the formula (I) in which Q is 3-bromopropyl;

a nitrile compound of the formula (I) in which Q is 2-bromopropyl;

a nitrile compound of the formula (I) in which Q is 2,3-dichloropropyl;

a nitrile compound of the formula (I) in which Q is 2,2-difluoropropyl;

a nitrile compound of the formula (I) in which Q is 3,3,3-trifluoropropyl;

a nitrile compound of the formula (I) in which Q is 2,2,3,3-tetrafluoropropyl;

a nitrile compound of the formula (I) in which Q is 2,2,3,3,3-pentafluoropropyl;

a nitrile compound of the formula (I) in which Q is 1,1,2,3,3,3-hexafluoropropyl;

a nitrile compound of the formula (I) in which Q is 1,1,2,3,3,3-heptafluoropropyl;

a nitrile compound of the formula (I) in which Q is 2,3-dichloro-2,3,3-trifluoropropyl;

a nitrile compound of the formula (I) in which Q is 2-chloro-3-bromo-2,3,3-trifluoropropyl;

a nitrile compound of the formula (I) in which Q is 3-bromo-2,2,3,3-tetrafluoropropyl;

a nitrile compound of the formula (I) in which Q is 2-(trifluoromethyl)-2,3,3,3-tetrafluoropropyl;

a nitrile compound of the formula (I) in which Q is C4 alkyl optionally substituted with one or more halogen;

a nitrile compound of the formula (I) in which Q is butyl;

a nitrile compound of the formula (I) in which Q is isobutyl;

a nitrile compound of the formula (I) in which Q is 4-fluorobutyl;

a nitrile compound of the formula (I) in which Q is 4-chlorobutyl;

a nitrile compound of the formula (I) in which Q is 2,2-difluorobutyl;

a nitrile compound of the formula (I) in which Q is 4,4-difluorobutyl;

a nitrile compound of the formula (I) in which Q is 4,4,4-trifluorobutyl;

a nitrile compound of the formula (I) in which Q is 4-bromo-3-chloro-3,4,4-trifluorobutyl;

a nitrile compound of the formula (I) in which Q is 4-bromo-3,3,4,4-tetrafluorobutyl;

a nitrile compound of the formula (I) in which Q is 3-(trifluoromethyl)-3,4,4,4-tetrafluorobutyl;

a nitrile compound of the formula (I) in which Q is 2,2,3,4,4,4-hexafluorobutyl;

a nitrile compound of the formula (I) in which Q is 3,3,4,4,4-pentafluorobutyl;

a nitrile compound of the formula (I) in which Q is 2,2,3,3,4,4,4-heptafluorobutyl;

a nitrile compound of the formula (I) in which Q is 1,1,2,2,3,3,4,4-octafluorobutyl;

a nitrile compound of the formula (I) in which Q is 1,1,2,2,3,3,4,4,4-nonafluorobutyl;

a nitrile compound of the formula (I) in which Q is C5 alkyl optionally substituted with one or more halogen;

a nitrile compound of the formula (I) in which Q is pentyl;

a nitrile compound of the formula (I) in which Q is isopentyl;

a nitrile compound of the formula (I) in which Q is 5,5,5-trifluoropentyl;

a nitrile compound of the formula (I) in which Q is 3,3,4,4,5,5,5-heptafluoropentyl;

a nitrile compound of the formula (I) in which Q is 2,2,3,3,4,4,5,5-octafluoropentyl;

a nitrile compound of the formula (I) in which Q is 2,2,3,3,4,4,5,5,5-nonafluoropentyl group;

a nitrile compound of the formula (I) in which Q is a C6 alkyl optionally substituted with one or more halogen;

a nitrile compound of the formula (I) in which Q is hexyl;

a nitrile compound of the formula (I) in which Q is isohexyl;

a nitrile compound of the formula (I) in which Q is 6,6,6-trifluorohexyl;

a nitrile compound of the formula (I) in which Q is 5,5,6,6,6-pentafluorohexyl;

a nitrile compound of the formula (I) in which Q is 4,4,5,5,6,6,6-heptafluorohexyl;

a nitrile compound of the formula (I) in which Q is 3,3,4,4,5,5,6,6-octafluorohexyl;

a nitrile compound of the formula (I) in which Q is 3,3,4,4,5,5,6,6,6-nonafluorohexyl;

a nitrile compound of the formula (I) in which Q is 1,1,2,2,3,3,4,4,5,5,6,6-dodecafluorohexyl;

a nitrile compound of the formula, (I) in which Q is C2-C6 alkenyl optionally substituted with one or more halogen;

a nitrile compound of the formula (I) in which Q is vinyl optionally substituted with one or more halogen;

a nitrile compound of the formula (I) in which Q is vinyl;

a nitrile compound of the formula (I) in which Q is 1-methylvinyl;

a nitrile compound of the formula (I) in which Q is 1-propenyl;

a nitrile compound of the formula (I) in which Q is 2-propenyl;

a nitrile compound of the formula (I) in which Q is 2,3,3-trifluoro-2-propenyl;

a nitrile compound of the formula (I) in which Q is 1-butenyl;

a nitrile compound of the formula (I) in which Q is 2-butenyl;

a nitrile compound of the formula (I) in which Q is 3-methyl-2-butenyl;

a nitrile compound of the formula (I) in which Q is 4,4,4-trifluoro-2-butenyl;

a nitrile compound of the formula (I) in which Q is 3-butenyl;

a nitrile compound of the formula (I) in which Q is 3,4,4-trifluoro-3-butenyl;

a nitrile compound of the formula (I) in which Q is C2-C6 alkynyl optionally substituted with one or more halogen;

a nitrile compound of the formula (I) in which Q is ethynyl;

a nitrile compound of the formula (I) in which Q is 1-propynyl;

a nitrile compound of the formula (I) in which Q is 2-methyl-1-propynyl;

a nitrile compound of the formula (I) in which Q is 3,3,3-trifluoro-1-propynyl;

a nitrile compound of the formula (I) in which Q is 2-propynyl;

a nitrile compound of the formula (I) in which Q is C3-C7 cycloalkyl optionally substituted with one or more halogen;

a nitrile compound of the formula (I) in which Q is cyclopropyl optionally substituted with one or more halogen;

a nitrile compound of the formula (I) in which Q is cyclopropyl;

a nitrile compound of the formula (I) in which Q is 2,2-dichlorocyclopropyl;

a nitrile compound of the formula (I) in which Q is cyclobutyl optionally substituted with one or more halogen;

a nitrile compound of the formula (I) in which Q is cyclobutyl;

a nitrile compound of the formula (I) in which Q is cyclopentyl optionally substituted with one or more halogen;

a nitrile compound of the formula (I) in which Q is cyclopentyl;

a nitrile compound of the formula (I) in which Q is cyclohexyl optionally substituted with one or more halogen;

a nitrile compound of the formula (I) in which Q is cyclohexyl;

a nitrile compound of the formula (I) in which Q is 4,4-difluorocyclohexyl;

a nitrile compound of the formula (I) in which Q is (C3-C7 cycloalkyl optionally substituted with one or more halogen) C1-C4 alkyl;

a nitrile compound of the formula (I) in which Q is C4-C6 alkyl optionally substituted with one or more halogen;

a nitrile compound of the formula (I) in which Q is cyclopropylmethyl;

a nitrile compound of the formula (I) in which Q is cyclopentylmethyl;

a nitrile compound of the formula (I) in which Q is 2,2-difluorocyclopropylmethyl;

a nitrile compound of the formula (I) in which Q is 3,3-difluorocyclopentylmethyl;

a nitrile compound of the formula (I) in which Q is C4-C6 alkyl optionally substituted with one or more fluorine;

a nitrile compound of the formula (I) in which Q is C4-C6 alkyl having 6 to 8 fluorine atoms;

a nitrile compound of the formula (I) in which Q is C3-C4 alkyl optionally substituted with one or more halogen;

a nitrile compound of the formula (I) in which Q is C3-C4 alkyl optionally substituted with one or more fluorine;

a nitrile compound of the formula (I) in which Q is C3-C4 alkyl having 6 to 8 fluorine atoms;

a nitrile compound of the formula (I) in which Q is C4 alkyl optionally substituted with one or more fluorine;

a nitrile compound of the formula (I) in which R is C2-C4 fluoroalkyl having 3 to 5 fluorine atoms and Q is C4-C6 alkyl optionally substituted with one or more halogen;

a nitrile compound of the formula (I) in which R is C3-C4 fluoroalkyl having 6 to 8 fluorine atoms and Q is C4-C6 alkyl optionally substituted with one or more halogen;

a nitrile compound of the formula (I) in which R is C2-C4 fluoroalkyl having 3 to 5 fluorine atoms and Q is C4-C6 alkyl optionally substituted with one or more fluorine atoms;

a nitrile compound of the formula (I) in which R is C3-C4 fluoroalkyl having 6 to 8 fluorine atoms and Q is C4-C6 alkyl optionally substituted with one or more fluorine atoms;

a nitrile compound of the formula (I) in which R is C2-C4 fluoroalkyl having 3 to 5 fluorine atoms and Q is C4-C6 alkyl having 6 to 8 fluorine atoms;

a nitrile compound of the formula (I) in which R is C3-C4 fluoroalkyl having 6 to 8 fluorine atoms and Q is C4-C6 alkyl having 6 to 8 fluorine atoms;

a nitrile compound of the formula (I) in which R is C2-C4 fluoroalkyl having 3 to 5 fluorine atoms and Q is C3-C4 alkyl optionally substituted with one or more halogen;

a nitrile compound of the formula (I) in which R is C3-C4 fluoroalkyl having 6 to 8 fluorine atoms and Q is C3-C4 alkyl optionally substituted with one or more fluorine atoms;

a nitrile compound of the formula (I) in which R is C2-C4 fluoroalkyl having 3 to 5 fluorine atoms and Q is C3-C4 alkyl having 6 to 8 fluorine atoms;

a nitrile compound of the formula (I) in which R is C3-C4 fluoroalkyl having 6 to 8 fluorine atoms and Q is C3-C4 alkyl optionally substituted with one or more halogen;

a nitrile compound of the formula (I) in which R is C2-C4 fluoroalkyl having 3 to 5 fluorine atoms and Q is C3-C4 alkyl optionally substituted with one or more fluorine atoms;

a nitrile compound of the formula (I) in which R is C3-C4 fluoroalkyl having 6 to 8 fluorine atoms and Q is C3-C4 alkyl having 6 to 8 fluorine atoms;

a nitrile compound of the formula (I) in which R is C2-C4 fluoroalkyl and Q is C1-C4 alkyl optionally substituted with one or more halogen;

a nitrile compound of the formula (I) in which R is C2 fluoroalkyl and Q is C1-C4 alkyl optionally substituted with one or more halogen;

a nitrile compound of the formula (I) in which R is 2,2,2-trifluoroethyl and Q is C1-C4 alkyl optionally substituted with one or more halogen;

a nitrile compound of the formula (I) in which R is C2-C4 fluoroalkyl and Q is C4 alkyl optionally substituted with one or more halogen;

a nitrile compound of the formula (I) in which R is C2-C3 fluoroalkyl substituted by at least two fluorine atoms in 2-position and Q is (C3-C5fluorocycloalkyl)methyl;

a nitrile compound of the formula (I) in which R is C2-C3 fluoroalkyl substituted by more than two fluoro atoms at least in 2-position and Q is 4,4-difuruorocyclohexyl;

a nitrile compound of the formula (I) in which R is C3-C4 fluoroalkyl substituted by at least two fluorine atoms in 1-position and at least one fluorine atoms in 3-position and Q is C2-C3 alkyl substituted by at least two fluorine atoms in 2-position;

a nitrile compound of the formula (I) in which R is C3-C4 fluoroalkyl substituted by two fluorine atoms 1-position and one or two fluorine atoms in 3-position and Q is C2-C3 alkyl substituted by at least two fluorine atoms in 2-position;

a nitrile compound of the formula (I) in which R is C2-C3 fluoroalkyl substituted by at least two fluorine atoms in 2-position and Q is C3-C4 alkyl optionally substituted with one or more halogen;

a nitrile compound of the formula (I) in which R is C2-C3 fluoroalkyl substituted by two fluorine atoms in 2-position and Q is C3 fluoroalkyl optionally substituted by chlorine or bromine;

a nitrile compound of the formula (I) in which R is C2-C3 fluoroalkyl substituted by two fluorine atoms in 2-position and Q is C3 fluoroalkyl;

a nitrile compound of the formula (I) in which R is C2-C3 fluoroalkyl substituted by two fluorine atoms in 2-position and Q is C4 fluoroalkyl;

a nitrile compound of the formula (I) in which R is C2-C3 fluoroalkyl substituted by at least two fluorine atoms in 2-position and Q is C4 fluoroalkyl substituted by two fluorine atoms in 1-position and one or two fluorine atoms in 3-position;

a nitrile compound of the formula (I) in which R is C2-C3 fluoroalkyl and Q is 1,1,2,2,3,3,4,4-octafluorobutyl;

a nitrile compound of the formula (I) in which R is C2-C3 fluoroalkyl substituted by at least two fluorine atoms at least in 2-position and Q is 1,1,2,2,3,3,4,4-octafluorobutyl;

a nitrile compound of the formula (I) in which R is C2-C4 fluoroalkyl and Q is 1,1,2,2,3,3,4,4-octafluorobutyl;

a nitrile compound of the formula (I) in which R is C3 fluoroalkyl and Q is 1,1,2,2,3,3,4,4-octafluorobutyl;

a nitrile compound of the formula (I) in which R is 2,2,2-trifluoroethyl and Q is 1,1,2,2,3,3,4,4-octafluorobutyl;

a nitrile compound of the formula (I) in which R is 2,2,3,3,3-pentafluoropropyl and Q is 1,1,2,2,3,3,4,4-octafluorobutyl;

a nitrile compound of the formula (I) in which R is C2 fluoroalkyl and Q is C4 alkyl optionally substituted with one or more halogen;

a nitrile compound of the formula (I) in which R is C2 fluoroalkyl and Q is 1,1,2,2,3,3,4,4-octafluorobutyl; and a nitrile compound of the formula (I) in which R is C4 fluoroalkyl and Q is 1,1,2,2,3,3,4,4-octafluorobutyl.

Then, a process for producing the present compound will be explained.

The present compound can be produced, for example, by any of the following (process 1) to (process 5).

(Process 1)

The present compound can be produced by reacting a compound (a) with a compound (b):

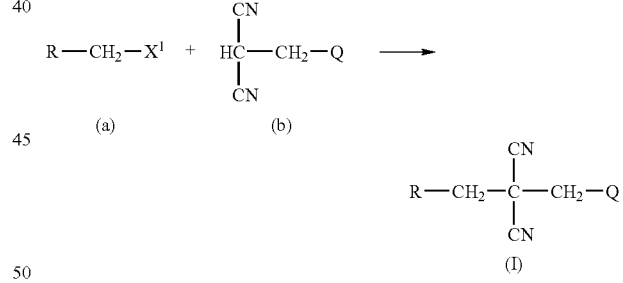

wherein R represents C1-C4 fluoroalkyl, Q represents halogen, C1-C11 alkyl optionally substituted with one or more halogen, C2-C6 alkenyl optionally substituted with one or more halogen, C2-C6 alkynyl optionally substituted with one or more halogen, C3-C7 cycloalkyl optionally substituted with one or more halogen or (C3-C7 cycloalkyl optionally substituted with one or more halogen) C1-C4 alkyl, and $X^1$ represents bromine, iodine, methanesulfonyloxy, toluenesulfonyloxy or trifluoromethanesulfonyloxy.

The reaction is usually performed in a solvent in the presence of a base.

A solvent used in the reaction includes aliphatic hydrocarbon such as hexane, heptane, octane or cyclohexane, aromatic hydrocarbon such as toluene, xylene or mesitylene, ether such as diethyl ether, methyl tert-butyl ether, tetrahydrofuran or 1,4-dioxane, acid amide such as N,N-dimethylformamide, dialkyl sulfoxide such as dimethyl sulfoxide, and a mixture thereof.

A base used in the reaction includes carbonate such as sodium carbonate or potassium carbonate, alkali metal hydride such as sodium hydride, and tertiary amine such as triethylamine or diisopropylethylamine.

The amount of the compound (a) used in the reaction is usually 1 to 10 moles per 1 mole of the compound (b).

The amount of a base used in the reaction is usually 1 to 10 moles per 1 mole of the compound (b).

The reaction temperature is usually in the range form −20 to 100° C. The reaction time is usually in the range from 0.1 to 24 hours.

After completion of the reaction, the present compound can be isolated by subjecting the reaction mixture to post-treatment such as adding the reaction mixture into water, extracting with an organic solvent, concentrating the extract and the like. The isolated present compound may be purified by chromatography, recrystallization or the like, if necessary.

(Process 2)

The present compound can be produced by reacting a compound (c) with a compound (d):

$$R-CH_2-\underset{\underset{CN}{|}}{\overset{\overset{CN}{|}}{CH}} \;+\; X^2-CH_2-Q \;\longrightarrow\; R-CH_2-\underset{\underset{CN}{|}}{\overset{\overset{CN}{|}}{C}}-CH_2-Q$$

(c)  (d)  (I)

wherein R and Q are as defined above and $X^2$ represents bromine, iodine, methanesulfonyloxy, toluenesulfonyloxy or trifluoromethanesulfonyloxy.

The reaction is usually performed in a solvent in the presence of a base.

A solvent used in the reaction includes aliphatic hydrocarbon such as hexane, heptane, octane or cyclohexane, aromatic hydrocarbon such as toluene, xylene or mesitylene, ether such as diethyl ether, methyl tert-butyl ether, tetrahydrofuran or 1,4-dioxane, acid amide such as N,N-dimethylformamide, dialkyl sulfoxides such as dimethyl sulfoxide, and a mixture thereof.

A base used in the reaction includes carbonate such as sodium carbonate or potassium carbonate, alkali metal hydride such as sodium hydride, and tertiary amine such as triethylamine or diisopropylethylamine.

The amount of the compound (d) used in the reaction is usually 1 to 10 moles per 1 mole of the compound (c).

The amount of a base used in the reaction is usually 1 to 10 moles per 1 mole of the compound (c).

The reaction temperature is usually in the range from −20 to 100° C. The reaction time is usually in the range from 0.1 to 24 hours.

After completion of the reaction, the present compound can be isolated by subjecting the reaction mixture to post-treatment such as adding the reaction mixture into water, extracting with an organic solvent, concentrating the extract and the like. The isolated present compound may be purified by chromatography, recrystallization or the like, if necessary.

(Process 3)

Among the present compounds, a compound (II) in which Q and R are the same C1-C4 fluoroalkyl group can be also produced by reacting a compound (e) with malononitrile:

$$\underset{\underset{CN}{|}}{\overset{\overset{CN}{|}}{CH_2}} \;+\; X^3-CH_2-Q^1 \;\longrightarrow\; R^1-CH_2-\underset{\underset{CN}{|}}{\overset{\overset{CN}{|}}{C}}-CH_2-Q^1$$

(X³—CH₂—R¹)

(e)  (II)

wherein $R^1$ and $Q^1$ represent the same C1-C4 fluoroalkyl group and $X^3$ represents chlorine, bromine, iodine, methanesulfonyloxy, toluenesulfonyloxy or trifluoromethanesulfonyloxy.

The reaction is usually performed in a solvent in the presence of a base.

A solvent used in the reaction includes aliphatic hydrocarbon such as hexane, heptane, octane or cyclohexane, aromatic hydrocarbon such as toluene, xylene or mesitylene, ether such as diethyl ether, methyl tert-butyl ether, tetrahydrofuran or 1,4-dioxane, acid amide such as N,N-dimethylformamide, dialkyl sulfoxides such as dimethyl sulfoxide, and a mixture thereof.

A base used in the reaction includes carbonate such as sodium carbonate or potassium carbonate, alkali metal hydride such as sodium hydride, and tertiary amine such as triethylamine or diisopropylethylamine.

The amount of malononitrile used in the reaction is usually 0.3 to 1 moles per 1 mole of the compound (e). The amount of a base used in the reaction is usually 0.6 to 5 moles per 1 mole of the compound (e).

The reaction temperature is usually in the range from −20 to 100° C. The reaction time is usually in the range from 0.1 to 36 hours.

After completion of the reaction, the present compound can be isolated by subjecting the reaction mixture to post-treatment such as adding the reaction mixture into water, extracting with an organic solvent, concentrating the extract and the like. The isolated compound (II) may be purified by chromatography, recrystallization or the like, if necessary.

(Process 4)

Among the present compounds, a compound (III) can be also produced by reacting a compound (c) with a compound (f):

$$R-CH_2-\underset{\underset{CN}{|}}{\overset{\overset{CN}{|}}{CH}} \;+\; CH_2\!\!=\!\!\overset{X^4}{\underset{X^5}{\diagup\!\!\!\diagdown}} \;\longrightarrow\; R-CH_2-\underset{\underset{CN}{|}}{\overset{\overset{CN}{|}}{C}}-CH_2-CH-X^4 \;\;\; X^5$$

(c)  (f)  (III)

wherein R is as defined above, $X^4$ represents C1-C10 perfluoroalkyl and $X^5$ represents halogen.

The reaction is usually performed in a solvent in the presence of a base.

A solvent used in the reaction includes aliphatic hydrocarbon such as hexane, heptane, octane or cyclohexane, aromatic hydrocarbon such as toluene, xylene or mesitylene, ether such as diethyl ether, methyl tert-butyl ether, tetrahydrofuran or 1,4-dioxane, acid amide such as N,N-dimethylformamide, dialkyl sulfoxides such as dimethyl sulfoxide, and a mixture thereof.

A base used in the reaction includes carbonate such as sodium carbonate or potassium carbonate, fluoride such as potassium fluoride or tetrabutylammonium fluoride, alkali metal hydride such as sodium hydride, and tertiary amine such as triethylamine or diisopropylethylamine.

The amount of the compound (f) used in the reaction is usually 1 to 10 moles per 1 mole of the compound (c). The amount of a base used in the reaction is usually 0.1 to 5 moles, preferably 0.6 to 5 moles, per 1 mole of the compound (c).

The reaction temperature is usually in the range from −20 to 100° C. The reaction time is usually in the range from 0.1 to 36 hours.

After completion of the reaction, the present compound can be isolated by subjecting the reaction mixture to post-treatment such as adding the reaction mixture into water, extracting with an organic solvent, concentrating the extract and the like. The isolated compound (III) may be purified by chromatography, recrystallization or the like, if necessary.

(Process 5)

Among the present compounds, a compound (IV) can be also produced by reacting a compound (g) with a fluorinating agent:

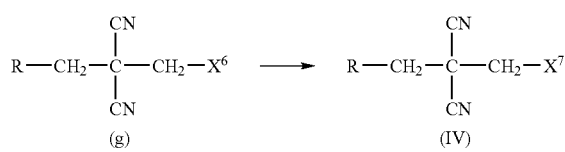

wherein R is as defined above, $X^6$ represents oxoC1-C11 alkyl, hydroxyC1-C11 alkyl, oxoC3-C6 alkenyl, hydroxyC3-C6 alkenyl, oxoC4-C6 alkynyl, hydroxyC4-C6 alkynyl, oxoC3-C7 cycloalkyl, hydroxyC3-C7 cycloalkyl, oxo(C3-C7 cycloalkyl)C1-C4 alkyl or hydroxyl(C3-C7 cycloalkyl)C1-C4 alkyl, and $X^7$ represents fluoroC1-C11 alkyl, fluoroC3-C6 alkenyl, fluoroC4-C6 alkynyl, fluoroC3-C7 alkyl, or fluoro(C3-C7 cycloalkyl)C1-C4 alkyl.

The reaction is performed in the presence or the absence of a solvent.

A solvent used in the reaction includes aliphatic hydrocarbon such as hexane, heptane, octane or cyclohexane, halogenated hydrocarbon such as carbon tetrachloride, chloroform or dichloromethane, and a mixture thereof.

A fluorinating agent used in the reaction includes diethylaminosulfur trifluoride and 2-chloro-1,1,2-trifluoroethyl-diethylamine.

The amount of a fluorinating agent used in the reaction is usually 1 to 10 moles per 1 mole of the compound (g).

The reaction temperature is usually in the range from −20 to 100° C. The reaction time is usually in the range from 0.1 to 36 hours.

After completion of the reaction, the reaction mixture may be poured into water and extracted with an organic solvent. The organic layer may be subjected to posttreatment such as drying and concentration to isolate the compound (IV). The isolated compound (IV) may be purified by chromatography, recrystallization or the like, if necessary.

Then, a process of producing an intermediate for production of the present compound will be explained.

The compound (b) can be produced, for example, by reacting a compound (d) with malononitrile:

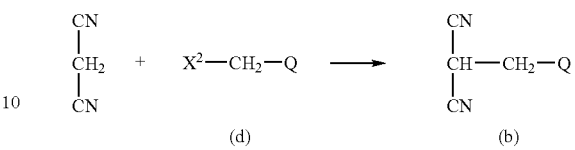

wherein Q and $X^2$ are as defined above.

The reaction is usually performed in a solvent in the presence of a base.

A solvent used in the reaction includes aliphatic hydrocarbon such as hexane, heptane, octane or cyclohexane, aromatic hydrocarbon such as toluene, xylene or mesitylene, ether such as diethyl ether, methyl tert-butyl ether, tetrahydrofuran or 1,4-dioxane, acid amide such as N,N-dimethylformamide, and a mixture thereof.

A base used in the reaction includes carbonate such as sodium carbonate or potassium carbonate, alkali metal hydride such as sodium hydride, and tertiary amine such as triethylamine or diisopropylethylamine.

The amount of malononitrile used in the reaction is usually 0.5 to 10 moles, preferably 0.5 to 1 mole, per 1 mole of the compound (d). The amount of a base used in the reaction is usually 0.5 to 5 moles per 1 mole of the compound (d).

The reaction temperature is usually in the range form −20 to 100° C. The reaction time is usually in the range from 0.1 to 24 hours.

After completion of the reaction, the present compound can be isolated by subjecting the reaction mixture to posttreatment such as adding the reaction mixture into water, extracting with an organic solvent, concentrating the extract and the like. The isolated compound (b) may be purified by chromatography, recrystallization or the like, if necessary.

The compound (c) can be produced, for example, by reacting a compound (a) with malononitrile:

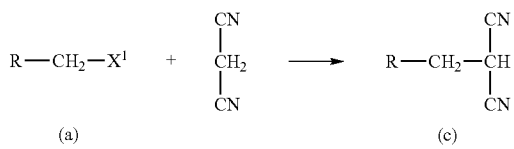

wherein R and $X^1$ are as defined above.

The reaction is usually performed in a solvent in the presence of a base.

A solvent used in the reaction includes aliphatic hydrocarbon such as hexane, heptane, octane or cyclohexane, aromatic hydrocarbon such as toluene, xylene or mesitylene, ether such as diethyl ether, methyl tert-butyl ether, tetrahydrofuran or 1,4-dioxane, acid amide such as N,N-dimethylformamide, and a mixture thereof.

A base used in the reaction includes carbonate such as sodium carbonate or potassium carbonate, alkali metal hydride such as sodium hydride, and tertiary amine such as triethylamine or diisopropylethylamine.

The amount of malononitrile used in the reaction is usually 0.5 to 10 moles, preferably 0.5 to 1 mole, per 1 mole of the compound (a). The amount of a base used in the reaction is usually 0.5 to 5 moles per 1 mole of the compound (a).

The reaction temperature is usually in the range form −20 to 100° C. The reaction time is usually in the range from 0.1 to 24 hours.

After completion of the reaction, the present compound can be isolated by subjecting the reaction mixture to post-treatment such as adding the reaction mixture into water, extracting with an organic solvent, concentrating the extract and the like. The isolated compound (c) may be purified by chromatography, recrystallization or the like, if necessary.

Alternatively, the compound (c) can be also produced by a process described in J. Chem. Soc. Perkin Trans. 1, 2589-2592(1991).

Pests against which the present compound has controlling effect include harmful arthropods such as insects and mites, and harmful nematodes. More specifically, examples thereof are listed below.

Hemiptera:
Delphacidae such as *Laodelphax striatellus, Nilaparvata lugens, Sogatella furcifera* and the like,
Deltocephalidae such as *Nephotettix cincticeps, Nephotettix virescens* and the like,
Aphididae such as *Aphis gossypii, Myzus persicae* and the like,
Pentatomidae and Alydidae, such as *Nezara antennata, Riptortus clavetus, Eysarcoris lewisi, Eysarcoris parvus, Plautia stali, Halyomorpha mista* and the like,
Aleyrodidae such as *Trialeurodes vaporariorum, Bemisia argentifolii* and the like,
Diaspididae, Coccidae and Margarodidae, such as *Aonidiella aurantii, Comstockaspis perniciosa, Unaspis citri, Ceroplastes rubens, Icerya purchasi* and the like,
Tingidae,
Cimicidae such as *Cimex lectularius* and the like,
Psyllidae, and the like;

Lepidoptera:
Pyralidae such as *Chilo suppressalis, Cnaphalocrocis medinalis, Notarcha derogata, Plodia interpunctella* and the like,
Noctuidae such as *Spodoptera litura, Pseudaletia separata, Trichoplusia* spp., *Heliothis* spp., *Helicoverpa* spp. and the like,
Pieridae such as *Pieris rapae* and the like,
Tortricidae such as *Adoxophyes* spp., *Grapholita molesta, Cydia pomonella* and the like,
Carposinidae such as *Carposina niponensis* and the like,
Lyonetiidae such as *Lyonetia* spp. and the like,
Lymantriidae such as *Lymantria* spp., *Euproctis* spp. and the like,
Yponomeutidae such as *Plutella xylostella* and the like,
Gelechiidae such as *Pectinophora gossypiella* and the like,
Arctiidae such as *Hyphantria cunea* and the like,
Tineidae such as *Tinea translucens, Tineola bisselliella* and the like;

Diptera:
Culicidae such as *Culex pipiens pallens, Culex tritaeniorhynchus, Culex quinquefasciatus* and the like,
*Aedes* spp. such as *Aedes aegypti, Aedes albopictus* and the like,
*Anopheles* spp. such as *Anopheles sinensis* and the like,
Chironomidae,
Muscidae such as *Musca domestica, Muscina stabulans* and the like,
Calliphoridae,
Sarcophagidae,
Fanniidae,
Anthomyiidae such as *Delia platura, Delia antiqua* and the like,
Tephritidae,
Drosophilidae,
Phoridae such as *Megaselia spiracularis* and the like,
Psychodidae such as *Clogmia albipunctata* and the like,
Simuliidae,
*Tabanidae,*
*Stomoxys* spp.,
Agromyzidae, and the like;

Coleoptera:
Corn rootworms such as *Diabrotica virgifera virgifera, Diabrotica undecimpunctata howardi* and the like,
Scarabaeidae such as *Anomala cuprea, Anomala rufocuprea* and the like,
Rhynchophoridae, Curculionidae and Bruchidae, such as *Sitophilus zeamais, Lissorhoptrus oryzophilus, Callosobruchus chienensis* and the like,
Tenebrionidae such as *Tenebrio molitor, Tribolium castaneum* and the like,
Chrysomelidae such as *Oulema oryzae, Aulacophora femoralis, Phyllotreta striolata, Leptinotarsa decemlineata* and the like,
Dermestidae such as *Dermestes maculates* and the like,
Anobiidae,
*Epilachna* spp. such as *Epilachna vigintioctopunctata* and the like,
Lyctidae,
Bostrychidae,
Ptinidae,
Cerambycidae,
*Paederus fuscipes*, and the like;
Blattaria: *Blattella germanica, Periplaneta fuliginosa, Periplaneta americana, Periplaneta brunnea, Blatta orientalis* and the like;
Thysanoptera: *Thrips palmi, Thrips tabaci, Frankliniella occidentalis, Frankliniella intonsa* and the like;

Hymenoptera:
Formicidae such as *Monomorium pharaosis, Formica fusca japonica, Ochetellus glaber, Pristomyrmex pungens, Pheidole noda*, and the like;
Vespidae,
Bethylidae,
Tenthredimidae such as *Athalia japonica*, and the like;

Orthoptera:
Gryllotalpidae,
Acrididae, and the like;
Aphaniptera: *Ctenocephalides felis, Ctenocephalides canis, Pulex irritans, Xenopsylla cheopis*, and the like;
Anoplura: *Pediculus humanus corporis, Phthirus pubis, Haematopinus eurysternus, Dalmalinia ovis*, and the like;

Isoptera:
Subterranean termites such as *Reticulitermes speratus, Coptotermes formosanus, Reticulitermes flavipes, Reticulitermes hesperus, Reticulitermes virginicus, Reticulitermes tibialis, Heterotermes aureus*, and the like, Dry wood termites such as *Incisitermes minor*, and the like, Damp wood termites such as *Zootermopsis nevadensis*, and the like;

Acarina:
Tetranychidae such as *Tetranychus urticae, Tetranychus kanzawai, Panonychus citri, Panonychus ulmi, Oligonychus* spp. and the like, Eriophyidae such as *Aculops pelekassi, Aculus schlechtendali*, and the like,
Tarsonemidae such as *Polyphagotarsonemus latus*, and the like,
Tenuipalpidae,
Tuckerellidae,
Ixodidae such as *Haemaphysalis longicornis, Haemaphysalis flava, Dermacentor variabilis, Ixodes ovatus, Ixodes persulcatus, Ixodes scapularis, Boophilus microplus, Amblyomma americanum, Rhipicephalus sanguineus*, and the like,
Acaridae such as *Tyrophagus putrescentiae*, and the like,
Epidermoptidae such as *Dermatophagoides farinae, Dermatophagoides ptrenyssnus*, and the like,
Cheyletidae such as *Cheyletus eruditus, Cheyletus malaccensis, Cheyletus moorei*, and the like,
Dermanyssidae such as *Dermanyssus gallinae*, and the like,
Trombiculidae such as *Leptotrombidium akamushi*, and the like;
Araneae: *Chiracanthium japonicum, Latrodectus hasseltii*, and the like;
Chilopoda: *Thereuonema hilgendorfi, Scolopendra subspinipes*, and the like;
Diplopoda: *Oxidus gracilis, Nedyopus tambanus*, and the like;
Isopoda: *Armadillidium vulgare*, and the like;
Gastropoda: *Limax marginatus, Limax flavus*, and the like;
Nematoda: *Pratylenchus coffeae, Pratylenchus fallax, Heterodera glycines, Globodera rostochiensis, Meloidogyne hapla, Meloidogyne incognita*, and the like.

Although the pesticidal composition of the present invention may be the present compound itself, it is usually formulated into a preparation by mixing with a solid carrier, a liquid carrier and/or a gaseous carrier and, further, if necessary, adding a surfactant and other adjuvants for formulation. That is, the pesticidal composition of the present invention usually contains the present compound and further contains an inert carrier. Such a preparation includes an emulsion, an oil, a shampoo preparation, a flowable preparation, a powder, a wettable agent, a granule, a paste, a microcapsule, a foam, an aerosol, a carbon dioxide gas preparation, a tablet, a resin preparation, a paper preparation, a nonwoven fabric preparation, and a knitted or woven fabric preparation. These preparations may be used in the form of a poison bait, a pesticide coil, an electric pesticide mat, a smoking preparation, a fumigant, or a sheet.

A preparation of the pesticidal composition of the present invention contains usually 0.01 to 98% by weight of the present compound.

A solid carrier used for formulation includes finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.) or chemical fertilizers (e.g., ammonium sulfate, ammonium phosphate, ammonium nitrate, ammonium chloride, urea, etc.); a substance which is in the solid form at normal temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier includes aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), acid amides (e.g., N,N-dimethylformamide, N,N-dimethylacetamide, N-methylpyrrolidone, etc.), alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), and water.

A gaseous carrier includes butane gas, chlorofluoro carbon gas, liquefied petroleum gas (LPG), dimethyl ether, and carbonic acid gas.

A surfactant includes alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

Other adjuvants for formulation include binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

A base material for a resin preparation includes polyethylene resins such as low-density polyethylene, straight low-density polyethylene and high-density polyethylene; ethylene-vinyl ester copolymers such an ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene copolymers and propylene-ethylene copolymers; poly-4-methylpentene-1, polybutene-1, polybutadiene, polystyrene, acrylonitrile-styrene resins; styrene elastomers such as acrylonitrile-butadiene-styrene resins, styrene-conjugated diene copolymers, and styrene-conjugated diene block copolymer hydrides; fluororesins; acrylic acid resins such as poly(methyl methacrylate); polyamide resins such as nylon 6 and nylon 66; polyester resins such as polyethylene terephthalate, polyethylene naphthalate, polybutylene butylate, and polycylohexylenedimethylene terephthalate; polycarbonates, polyacetals, polyacrylsulfones, polyarylate, hydroxybenzoic acid polyesters, polyetherimides, polyester carbonates, polyphenylene ether resins, polyvinyl chloride, polyvinylidene chloride, and polyurethane. These base materials may be used alone or as a mixture of two or more. A plasticizer such as phthalic acid ester (e.g., dimethyl phthalate, dioctyl phthalate, etc.), adipic acid ester or stearic acid may be added to these base materials, if necessary.

The resin preparation can be obtained by kneading the present compound into the base material, followed by molding such as injection molding, extrusion molding or press molding. The resulting resin preparation may be formed into the shape of a plate, a film, a tape, a net, a string or the like via a further step of molding, cutting, or the like, if necessary. These resin preparations may be used in the form of an animal collar, an animal ear tag, a sheet preparation, a lead, or a horticultural post.

A base material of a poison bait includes cereal powder, vegetable oil, sugar and crystalline cellulose. An antioxidant such as dibutylhydroxytoluene or nordihydroguairetic acid, a preservative such as dehydroacetic acid, an agent for preventing children or pets from erroneously eating such as hot pepper powder, and a pest-attractive perfume such as cheese perfume, onion perfume or peanut oil may be added to the base material, if necessary.

The present compound can be used in pest control by applying an effective amount of the present compound to pests directly and/or habitats of pests (e.g., plants, animals, soil, etc.).

When the pesticidal composition of the present invention is used for controlling pests in agriculture and forestry, the application amount is usually 1 to 100,000 g/ha, preferably 10 to 1,000 g/ha of the present compound. When the pesticidal composition of the present invention is the form of an emulsion, a wettable agent, a flowable agent, or a microcapsule, it is usually used after dilution with water so as to have an active ingredient concentration of 0.01 to 1,000 ppm. When the pesticidal composition of the present invention is the form of oil, powder or a granule, it is usually used as it is. These preparations may be sprayed as they are to plants to be protected from pests, or may be diluted with water and then sprayed to a plant to be protected from pests. Soil can be treated with these preparations to control pests living in the soil. Seedbeds before planting or planting holes or plant feet in planting can be also treated with these preparations. Further, a sheet preparation of the pesticidal composition of the present invention may be applied by winding around plants, disposing in the vicinity of plants, laying on the soil surface at the plant feet, or the like.

When the pesticidal composition of the present invention is used for a control of pests of epidemic, the application amount is usually 0.001 to 100 mg/m$^3$ of the present compound for application to space, and 0.001 to 1,000 mg/m$^2$ of the present compound for application to a plane. The pesticidal composition in the form of an emulsion, wettable agent or a flowable agent is usually applied after dilution with water so as to contain usually 0.001 to 100,000 ppm, preferably 0.01 to 1,000 ppm of the present compound. The pesticidal composition in the form of an oil, an aerosol, a smoking preparation or a poison bait is usually applied as it is. The pesticidal composition in the form of pesticide coil, or an electric pesticide mat is applied by emitting the active ingredient by heating depending on its form. The pesticidal composition in the form of a resin preparation, a paper preparation, a tablet, a nonwoven fabric preparation, a knitted or woven fabric preparation or a sheet preparation can be applied, for example, by leaving the preparation as it is in a space to be applied and by sending air to the preparation. A space to which the pesticidal composition of the present invention is applied for prevention of epidemics includes a closet, a Japanese-style closet, a Japanese-style chest, a cupboard, a lavatory, a bathroom, a lumber room, a living room, a dining room, a warehouse, and the car inside. The pesticidal composition may be also applied in outdoor open space.

When the pesticidal composition of the present invention is used for controlling parasites living outside of a livestock such as a cow, a horse, a pig, a sheep, a goat or a chicken, or a small animal such as a dog, a cat, a rat or a mouse, it can be used for said animal by a known method in the veterinary filed. Specifically, when systemic control is intended, the pesticidal composition is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil or an aqueous liquid, washing an animal with the pesticidal composition in the form of a shampoo preparation, and attachment of a collar or a ear tag made of the pesticidal composition in the form of a resin preparation to an animal. When administered to an animal, the amount of the present compound is usually in the range of 0.01 to 1,000 mg per 1 kg body weight of the animal.

The pesticidal composition of the present invention may be used in admixture or combination with other insecticides, nematocides, acaricides, fungicides, herbicides, plant growth regulators, synergists, fertilizers, soil conditioners, animal feed, and the like.

The active ingredient of such insecticide or acaricide includes pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin,a flumethrin, imiprothrin, etofenprox, fenvalerate, esfenvalerate, fenpropathrin, silafluofen, bifenthrin, transfluthrin, flucythrinate, tau-fluvalinate, acrinathrin, tefluthrin, cycloprothrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, dimefluthrin and empenthrin; organic phosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion; carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron, triazuron and bistrifluron; juvenile hormone-like substances such as pyriproxyfen, methoprene, hydroprene and fenoxycarb; neonicotinoid compounds such as acetamiprid, nitenpyram, thiacloprid, thiamethoxam and dinotefuran; N-phenylpyrazole compounds such as acetoprole and ethiprole; benzoylhydrazine compounds such as tebufenozide, chromafenozide, methoxyfenozide and halofenozide; diafenthiuron; pymetrozine; flonicamid; triazamate; buprofezin; spinosad; emamectin benzoate; chlorfenapyr; indoxacarb MP; pyridalyl; cyromazine; fenpyroximate; tebufenpyrad; tolfenpyrad; pyridaben; pyrimidifen; fluacrypyrim; etoxazole; fenazaquin; acequinocyl; hexythiazox; clofentezine; fenbutatin oxide; dicofol, propargite; abamectin; milbemectin; amitraz; cartap; bensultap; thiocyclam; endosulfan; spirodiclofen; spiromesifen; amidoflumet and azadirachtin.

The active ingredient of such fungicide includes strobilurin compounds such as azoxystrobin; organic phosphorus compounds such as tolclofos-methyl; azole compounds such as metconazole, hexaconazole, ipconazole, sipconazole, triflumizole, pefurazoate and difenoconazole; iodopropargyl compounds such as IPBC; isothiazolone compounds such as OIT and MEC; fthalide; flutolanil; validamycin; probenazole; diclomezine; pencycuron; dazomet; kasugamycin; IBP; pyroquilon; oxolinic acid; tricyclazole; ferimzone; mepronil; EDDP; isoprothiolane; carpropamid; diclocymet; furametpyr; fludioxonil; procymidone; and diethofencarb.

EXAMPLES

The present invention will be explained in more detail by the following Production Examples, Formulation Examples and Experimental Examples, but the present invention is not limited to them.

First, Production Examples of the present compound will be described.

Production Example 1

(1) 0.5 g of sodium hydride (60% oil) was suspended in 10 ml of N,N-dimethylformamide and thereto was added a solution of 1.6 g of (3,3,3-trifluoropropyl)malononitrile in 10 ml of N,N-dimethylformamide at about 0° C. The mixture was warmed to room temperature and N,N-dimethylformamide was added thereto to a total volume of 20 ml (hereinafter, the solution thus obtained is referred to as the solution A).

(2) 0.23 g of 1-bromo-3-chloropropane was dissolved in 1 ml of N,N-dimethylformamide and 2 ml of the solution A was added thereto. After the mixture was stirred at room temperature for 4 hours, dilute hydrochloric acid was added to the reaction mixture, followed by extraction with ethyl acetate. The organic layer was washed successively with water and aqueous saturated sodium chloride, dried over anhydrous magnesium sulfate, and then concentrated under reduced pressure. The residue was subjected to silica gel column chromatography to obtain 0.13 g of 2-(3-chloropropyl)-2-(3,3,3-trifluoropropyl)malononitrile (hereinafter, referred to as the present compound (1)).

The present compound (1):
$^1$H-NMR(CDCl$_3$, TMS) δ(ppm): 2.13-2.21 (6H, m), 2.42-2.53(2H, m), 3.62(2H, t).

Production Example 2

0.11 g of 2-(3-chloro-2-methylpropyl)-2-(3,3,3-trifluoropropyl)malononitrile (hereinafter, referred to as the present compound (2)) was obtained according to Production Example 1 (2) except that 0.17 g of 1-bromo-3-chloro-2-methylpropane was used in place of 1-bromo-3-chloropropane.

The present compound (2):
$^1$H-NMR(CDCl$_3$, TMS) δ(ppm): 1.26(3H, d), 1.84-1.92 (1H, m), 2.21-2.38(4H, m), 2.43-2.57(2H, m), 3.43-3.68(2H, m).

Production Example 3

0.17 g of 2-(4-chlorobutyl)-2-(3,3,3-trifluoropropyl)malononitrile (hereinafter, referred to as the present compound (3)) was obtained according to Production Example 1 (2) except that 0.17 g of 1-bromo-4-chlorobutane was used in place of 1-bromo-3-chloropropane.

The present compound (3):
$^1$H-NMR(CDCl$_3$, TMS) δ(ppm): 1.82-1.94(4H, m), 1.96-2.06(2H, m), 2.13-2.21(2H, m), 2.41-2.53(2H, m), 2.54(2H, t).

Production Example 4

0.12 g of 2-(2,2-dichlorocyclopropylmethyl)-2-(3,3,3-trifluoropropyl)malononitrile (hereinafter, referred to as the present compound (4)) was obtained according to Production Example 1 (2) except that 0.21 g of 2-bromomethyl-1,1-dichlorocyclopropane was used in place of 1-bromo-3-chloropropane.

The present compound (4):
$^1$H-NMR(CDCl$_3$, TMS) δ(ppm): 1.42(1H, t), 1.81-1.96 (2H, m), 2.08-2.12(1H, m), 2.22-2.29(2H, m), 2.43-2.58(3H, m).

Production Example 5

2.00 g of malononitrile and 13.0 g of 1-bromo-3,3,3-trifluoropropane were dissolved in 10 ml of N,N-dimethylformamide and then cooled in an ice bath. After 8.4 g of potassium carbonate was added thereto, the mixture was stirred at room temperature for 30 hours. To the reaction mixture ice water and ethyl acetate were added. The mixture was stirred and then separated into layers. The aqueous layer was extracted with ethyl acetate. The organic layers were combined, washed successively with water and aqueous saturated sodium chloride, dried over anhydrous magnesium sulfate, and then concentrated under reduced pressure. The residue was subjected to silica gel column chromatography to obtain 4.75 g of 2,2-bis(3,3,3-trifluoropropyl)malononitrile (hereinafter, referred to as the present compound (5)).

The present compound (5):
$^1$H-NMR(CDCl$_3$, TMS) δ(ppm): 2.26-2.33(4H, m), 2.52-2.61(4H, m).

Production Example 6

0.03 g of 2-ethyl-2-(3,3,3-trifluoropropyl)malononitrile (hereinafter, referred to as the present compound (6)) was obtained according to Production Example 1 (2) except that 0.16 g of iodoethane was used in place of 1-bromo-3-chloropropane.

The present compound (6):
$^1$H-NMR(CDCl$_3$, TMS) δ(ppm): 1.32(3H,t), 2.06(2H, q), 2.14-2.22(2H, m), 2.42-2.57(2H, m).

Production Example 7

0.05 g of 2-propyl-2-(3,3,3-trifluoropropyl)malononitrile (hereinafter, referred to as the present compound (7)) was obtained according to Production Example 1 (2) except that 0.17 g of 1-iodopropane was used in place of 1-bromo-3-chloropropane.

The present compound (7)
$^1$H-NMR(CDCl$_3$, TMS) δ(ppm): 1.08(3H, t), 1.68-1.77(2H, m), 1.91-1.96(2H,m), 2.13-2.21(2H, m), 2.43-2.57(2H, m).

Production Example 8

0.11 g of 2-butyl-2-(3,3,3-trifluoropropyl)malononitrile (hereinafter, referred to as the present compound (8)) was obtained according to Production Example 1 (2) except that 0.18 g of 1-iodobuthane was used in place of 1-bromo-3-chloropropane.

The present compound (8):
$^1$H-NMR(CDCl$_3$, TMS) δ(ppm): 0.98(3H, t), 1.46(2H, q), 1.63-1.72(2H, m), 1.94-2.03(2H, m), 2.18-2.23(2H, m), 2.43-2.55(2H, m).

Production Example 9

0.10 g of 2-pentyl-2-(3,3,3-trifluoropropyl)malononitrile (hereinafter, referred to as the present compound (9)) was obtained according to Production Example 1 (2) except that 0.20 g of 1-iodopentane was used in place of 1-bromo-3-chloropropane.

The present compound (9):
$^1$H-NMR(CDCl$_3$, TMS) δ(ppm): 0.91-1.02(3H, m), 1.38-1.45(4H,m), 1.61-1.74(2H, m), 1.93-2.07(2H, m), 2.13-2.24(2H, m), 2.47-2.54(2H, m).

Production Example 10

0.13 g of 2-hexyl-2-(3,3,3-trifluoropropyl)malononitrile (hereinafter, referred to as the present compound (10)) was obtained according to Production Example 1 (2) except that 0.21 g of 1-iodohexane was used in place of 1-bromo-3-chloropropane.

The present compound (10):
$^1$H-NMR(CDCl$_3$, TMS) δ(ppm): 0.87(3H,t), 1.28-1.43(6H, m), 1.63-1.72(2H, m), 1.91-2.01(2H, m), 2.13-2.19(2H, m), 2.42-2.51(2H, m).

Production Example 11

0.10 g of 2-heptyl-2-(3,3,3-trifluoropropyl)malononitrile (hereinafter, referred to as the present compound (11)) was obtained according to Production Example 1 (2) except that 0.23 g of 1-iodoheptane was used in place of 1-bromo-3-chloropropane.

The present compound (11):
$^1$H-NMR(CDCl$_3$, TMS) δ(ppm): 0.90(3H, t), 2.21-2.42(8H, m), 2.59-2.68(2H, m), 1.91-2.02(2H, m), 2.12-2.28(2H, m), 2.41-2.53(2H, m).

Production Example 12

0.17 g of 2-octyl-2-(3,3,3-trifluoropropyl)malononitrile (hereinafter, referred to as the present compound (12)) was obtained according to Production Example 1 (2) except that 0.24 g of 1-iodooctane was used in place of 1-bromo-3-chloropropane.

The present compound (12):
$^1$H-NMR(CDCl$_3$, TMS) δ(ppm): 0.89(3H, t), 1.21-1.42(10H, m), 1.63-1.71(2H, m), 1.92-1.97(2H, m), 2.13-2.19(2H, m), 2.41-2.58(2H, m).

Production Example 13

0.19 g of 2-nonyl-2-(3,3,3-trifluoropropyl)malononitrile (hereinafter, referred to as the present compound (13)) was obtained according to Production Example 1 (2) except that 0.21 g of 1-bromononane was used in place of 1-bromo-3-chloropropane.

The present compound (13):
$^1$H-NMR(CDCl$_3$, TMS) δ(ppm): 0.89(3H, t), 1.21-1.48(12H, m), 1.68-1.77(2H, m), 1.96-2.03(2H, m), 2.19-2.23(2H, m), 2.43-2.61(2H, m).

Production Example 14

0.15 g of 2-decyl-2-(3,3,3-trifluoropropyl)malononitrile (hereinafter, referred to as the present compound (14)) was obtained according to Production Example 1 (2) except that 0.22 g of 1-bromodecane was used in place of 1-bromo-3-chloropropane.

The present compound (14):
$^1$H-NMR(CDCl$_3$, TMS) δ(ppm): 0.89(3H, t), 1.22-1.48(14H, m), 1.68-1.74(2H, m), 1.97-2.01(2H, m), 2.18-2.22(2H, m), 2.48-2.63(2H, m).

Production Example 15

0.12 g of 2-allyl-2-(3,3,3-trifluoropropyl)malononitrile (hereinafter, referred to as the present compound (15)) was obtained according to Production Example 1 (2) except that 0.12 g of allyl bromide was used in place of 1-bromo-3-chloropropane.

The present compound (15):
$^1$H-NMR(CDCl$_3$, TMS) δ(ppm): 2.12-2.21(2H, m), 2.43-2.58(2H, m), 2.75(2H, d), 5.43-5.51(2H, m), 5.84-5.95(1H, m)

Production Example 16

0.13 g of 2-(3-butenyl)-2-(3,3,3-trifluoropropyl)malononitlire (hereinafter, referred to as the present compound (16)) was obtained according to Production Example 1 (2) except that 0.14 g of 1-bromo-3-butene was used in place of 1-bromo-3-chloropropane.

The present compound (16):
$^1$H-NMR(CDCl$_3$, TMS) δ(ppm): 2.06-2.10(2H,m), 2.21-2.24(2H, m), 2.45-2.58(4H, m), 5.14-5.23(2H, m), 5.81-5.85(1H,m).

Production Example 17

0.19 g of 2-(3,3,4-trifluoro-3-butenyl)-2-(3,3,3-trifluoropropyl)malononitrile (hereinafter, referred to as the present compound (17)) was obtained according to Production Example 1 (2) except that 0.19 g of 1-bromo-3,4,4-trifluoro-3-butene was used in place of 1-bromo-3-chloropropane.

The present compound (17):
¹H-NMR(CDCl₃, TMS) δ(ppm): 2.23-2.27(4H, m), 2.52-2.61(2H, m), 2.69-2.80(2H, m).

Production Example 18

0.4 g of 2-(3,3,3-trifluoropropyl)malononitrile and 0.5 g of cyclopropylmethyl bromide were dissolved in 5 ml of dimethyl sulfoxide and thereto was added 0.41 g of potassium carbonate. The mixture was stirred at room temperature for 5 hours. Then, dilute hydrochloric acid was added to the reaction mixture, followed by extraction with ethyl acetate. The organic layer was washed successively with water and aqueous saturated sodium chloride, dried over anhydrous magnesium sulfate, and then concentrated under reduced pressure. The residue was subjected to silica gel column chromatography to obtain 0.34 g of 2-cyclopropylmethyl-2-(3,3,3-trifluoropropyl)malononitrile (hereinafter, referred to as the present compound (18)).

The present compound (18):
¹H-NMR(CDCl₃, TMS) δ(ppm): 0.40(2H, dd), 0.72(2H, dd), 0.91-0.98(1H, m), 1.95(2H, d) 2.16-2.23(2H, m), 2.43-2.52(2H, m).

Production Example 19

0.34 g of 2-cyclobutylmethyl-2-(3,3,3-trifluoropropyl)malononitrile (hereinafter, referred to as the present compound (19)) was obtained according to Production Example 18 except that 0.44 g of cyclobutylmethyl bromide was used in place of cyclopropylmethyl bromide.

The present compound (19):
¹H-NMR(CDCl₃, TMS) δ(ppm): 1.81-1.92(2H, m), 1.93-2.01(2H, m), 2.06(2H, d), 2.11-2.19(2H, m), 2.22-2.27(2H, m), 2.41-2.52(2H, m), 2.61-2.69(1H, m).

Production Example 20

0.34 g of 2-(2,2,3,3-tetrafluoropropyl)-2-(3,3,3-trifluoropropyl)malononitrile (hereinafter, referred to as the present compound (20)) was obtained according to Production Example 18 except that 0.44 g of 2,2,3,3-tetrafluoropropyl trifluoromethanesulfonate was used in place of cyclopropylmethyl bromide.

The present compound (20):
¹H-NMR(CDCl₃, TMS) δ(ppm): 2.34-2.41(2H, m), 2.55-2.63(2H, m), 2.74(2H, t), 5.88(1H, tt).

Production Example 21

0.2 g of 2-(2,2,2-trifluoroethyl)-2-(3,3,3-trifluoropropyl)malononitrile (hereinafter, referred to as the present compound (21)) was obtained according to Production Example 18 except that 1.2 g of 2,2,2-trifluoroethyl trifluoromethanesulfonate was used in place of cyclopropylmethyl bromide.

The present compound (21):
¹H-NMR(CDCl₃, TMS) δ(ppm): 2.30-2.38(2H, m), 2.51-2.69(2H, m), 2.87(2H, q).

Production Example 22

0.2 g of 2-(2,2,3,3,3-pentafluoropropyl)-2-(3,3,3-trifluoropropyl)malononitrile (hereinafter, referred to as the present compound (22)) was obtained according to Production Example 18 except that 1.3 g of 2,2,3,3,3-pentafluoropropyl trifluoromethanesulfonate was used in place of cyclopropylmethyl bromide.

The present compound (22):
¹H-NMR(CDCl₃, TMS) δ(ppm): 2.35-2.41(2H, m), 2.57-2.67(2H, m), 2.81(2H, t).

Production Example 23

0.34 g of 2-(2,2,3,4,4,4-hexafluorobutyl)-2-(3,3,3-trifluoropropyl)malononitrile (hereinafter, referred to as the present compound (23)) was obtained according to Production Example 18 except that 2.4 g of 2,2,3,4,4,4-hexafluorobutyl trifluoromethanesulfonate was used in place of cyclopropylmethyl bromide.

The present compound (23):
¹H-NMR(CDCl₃, TMS) δ(ppm): 2.36-2.40(2H, m), 2.57-2.68(2H, m), 2.81-2.91(2H, m), 4.85-5.03(1H, m).

Production Example 24

2.0 g of 2-(2,2,3,3,4,4,4-heptafluorobutyl)-2-(3,3,3-trifluoropropyl)malononitrile (hereinafter, referred to as the present compound (24)) was obtained according to Production Example 18 except that 15 g of 2,2,3,3,4,4,4-heptafluorobutyl trifluoromethanesulfonate was used in place of cyclopropylmethyl bromide.

The present compound (24):
¹H-NMR(CDCl₃, TMS) δ(ppm): 2.37-2.41(2H, m), 2.58-2.80(2H, m), 2.86(2H, t).

Production Example 25

0.4 g of 2-(2-fluoroethyl)-2-(3,3,3-trifluoropropyl)malononitrile (hereinafter, referred to as the present compound (25)) was obtained according to Production Example 18 except that 2.2 g of 2-fluoroethyl toluenesulfonate was used in place of cyclopropylmethyl bromide.

The present compound (25):
¹H-NMR(CDCl₃, TMS) δ(ppm): 2.29-2.34(2H, m), 2.40-2.42(2H, m), 2.46-2.59(2H, m), 4.82(2H, dt).

Production Example 26

0.6 g of 2-((2-perfluorohexyl)ethyl)-2-(3,3,3-trifluoropropyl)malononitrile (hereinafter, referred to as the present compound (26)) was obtained according to Production Example 18 except that 4.7 g of (2-perfluorohexyl)ethyl iodide was used in place of cyclopropylmethyl bromide.

The present compound (26):
¹H-NMR(CDCl₃, TMS) δ(ppm): 2.27-2.35(4H, m), 2.47-2.61(4H, m).

Production Example 27

0.94 g of 2-(3,3,3-trifluoropropyl)-2-(2-propynyl)malononitrile (hereinafter, referred to as the present compound (27)) was obtained according to Production Example 18 except that 1.2 g of 3-bromo-1-propyne was used in place of cyclopropylmethyl bromide.

The present compound (27):
¹H-NMR(CDCl₃, TMS) δ(ppm): 2.34-2.39(2H, m), 2.44-2.57(3H, m), 3.00(2H, s).

Production Example 28

0.64 g of 2-cyclohexylmethyl-2-(3,3,3-trifluoropropyl)malononitrile (hereinafter, referred to as the present compound (28)) was obtained according to Production Example 18 except that 1.8 g of (bromomethyl)cyclohexane was used in place of cyclopropylmethyl bromide.

The present compound (28):
¹H-NMR(CDCl₃, TMS) δ(ppm): 1.14-1.71(5H, m), 1.80-1.98(8H, m), 2.06-2.11(2H, m), 2.21-2.28(2H, m).

Production Example 29

1.8 g of 2-(3,3,4,4,4-pentafluorobutyl)-2-(3,3,3-trifluoropropyl)malononitrile (hereinafter, referred to as the present compound (29)) was obtained according to Production Example 18 except that 2.8 g of 3,3,4,4,4-pentafluorobutyl iodide was used in place of cyclopropylmethyl bromide.

The present compound (29):
¹H-NMR(CDCl₃, TMS) δ(ppm): 2.12-2.20(4H, m), 2.23-2.59(4H, m).

Production Example 30

0.89 g of 2-(4-bromo-3-chloro-3,4,4-trifluorobutyl)-2-(3,3,3-trifluoropropyl)malononitrile (hereinafter, referred to as the present compound (30)) was obtained according to Production Example 18 except that 2.8 g of 1-bromo-2-chloro-4-iodo-1,1,2-trifluorobutane was used in place of cyclopropylmethyl bromide.

The present compound (30):
¹H-NMR(CDCl₃, TMS) δ(ppm): 2.30-2.65(7H, m), 2.74-2.83(1H, m).

Production Example 31

0.54 g of 2-(2,2,3,3,4,4,5,5-octafluoropentyl)-2-(3,3,3-trifluoropropyl)malononitrile (hereinafter, referred to as the present compound (31)) was obtained according to Production Example 18 except that 1.6 g of 2,2,3,3,4,4,5,5-octafluoropentyl trifluoromethanesulfonate was used in place of cyclopropylmethyl bromide.

The present compound (31):
¹H-NMR(CDCl₃, TMS) δ(ppm): 2.36-2.41(2H, m), 2.57-2.65(2H, m), 2.84(2H, t), 6.07(1H, tt).

Production Example 31-2

1.4 g of 2-(2,2,3,3,4,4,5,5-octafluoropentyl)malononitrile and 1.2 g of 1-bromo-3,3,3-trifluoropropane were dissolved in 10 ml of ethylene glycol dimethyl ether, 0.97 g of potassium carbonate was added, and the mixture was stirred at room temperature for 10 hours. Thereafter, dilute hydrochloric acid was added to the reaction mixture, followed by extraction with methyl tert-butyl ether. The organic layer was washed successively with water, an aqueous saturated sodium bicarbonate solution and aqueous saturated sodium chloride, dried over anhydrous magnesium sulfate, and then concentrated under reduced pressure. The residue was subjected to silica gel column chromatography to obtain 0.74 g of the present compound (31).

Production Example 32

0.70 g of 2-(2,2,3,3,4,4,5,5,6,6,7,7-dodecafluoroheptyl)-2-(3,3,3-trifluoropropyl)malononitrile (hereinafter, referred to as the present compound (32)) was obtained according to Production Example 18 except that 1.6 g of (2,2,3,3,4,4,5,5,6,6,7,7-dodecafluoroheptyl)trifluoromethanesulfonic acid ester was used in place of cyclopropylmethyl bromide.

The present compound (32):
¹H-NMR(CDCl₃, TMS) δ(ppm): 2.36-2.41(2H, m), 2.58-2.65(2H, m), 2.84(2H, t), 6.06(1H, tt).

Production Example 33

2.0 g of 2-((2-perfluorodecyl)ethyl)-2-(3,3,3-trifluoropropyl)malononitrile (hereinafter, referred to as the present compound (33)) was obtained according to Production Example 18 except that 3.2 g of 2-(perfluorodecyl)ethyl iodide was used in place of cyclopropylmethyl bromide.

The present compound (33):
¹H-NMR(CDCl₃, TMS) δ(ppm): 2.66-2.80(4H, m), 3.23-3.29(4H, m).

Production Example 34

0.1 g of 2-((2-perfluorooctyl)ethyl)-2-(3,3,3-trifluoropropyl)malononitrile (hereinafter, referred to as the present compound (34)) was obtained according to Production Example 18 except that 2.4 g of 2-(perfluorooctyl)ethyl iodide was used in place of cyclopropylmethyl bromide.

The present compound (34):
¹H-NMR(CDCl₃, TMS) δ(ppm): 2.27-2.35(4H, m), 2.45-2.58(4H, m).

Production Example 35

0.53 g of 2-(4-bromo-3,3,4,4-tetrafluorobutyl)-2-(3,3,3-trifluoropropyl)malononitrile (hereinafter, referred to as the present compound (35)) was obtained according to Production Example 18 except that 1.7 g of 1-bromo-4-iodo-1,1,2,2-tetrafluorobutane was used in place of cyclopropylmethyl bromide.

The present compound (35):
¹H-NMR(CDCl₃, TMS) δ(ppm): 2.26-2.36(4H, m), 2.47-2.61(4H, m).

Production Example 36

0.53 g of 2-(3,4,4,4-tetrafluoro-3-(trifluoromethyl)butyl)-2-(3,3,3-trifluoropropyl)malononitrile (hereinafter, referred to as the present compound (36)) was obtained according to Production Example 18 except that 1.7 g of 4-iodo-1,1,1,2-tetrafluoro-2-(trifluoromethyl)butane was used in place of cyclopropylmethyl bromide.

The present compound (36):
¹H-NMR(CDCl₃, TMS) δ(ppm): 2.23-2.32(4H, m), 2.47-2.61(4H, m).

Production Example 37

0.23 g of 2-(3,3,4,4,5,5,5-heptafluoropentyl)-2-(3,3,3-trifluoropropyl)malononitrile (hereinafter, referred to as the present compound (37)) was obtained according to Production Example 18 except that 1.6 g of 5-iodo-1,1,1,2,2,3,3-heptafluoropentane was used in place of cyclopropylmethyl bromide.

The present compound (37):
$^1$H-NMR(CDCl$_3$, TMS) δ(ppm): 2.28-2.35(4H, m), 2.48-2.61(4H, m).

Production Example 38

0.64 g of 2-(3,3,4,4,5,5,6,6,6-nonafluorohexyl)-2-(3,3,3-trifluoropropyl)malononitrile (hereinafter, referred to as the present compound (38)) was obtained according to Production Example 18 except that 2.1 g of 3,3,4,4,5,5,6,6,6-nonafluorohexyl iodide was used in place of cyclopropyl methyl bromide.

The present compound (38):
$^1$H-NMR(CDCl$_3$, TMS) δ(ppm): 2.26-2.35(4H, m), 2.50-2.62(4H, m).

Production Example 39

0.62 g of 2-(3-fluoropropyl)-2-(3,3,3-trifluoropropyl)malononitrile (hereinafter, referred to as the present compound (39)) was obtained according to Production Example 18 except that 1.4 g of 3-fluoropropyl bromide was used in place of cyclopropylmethyl bromide.

The present compound (39):
$^1$H-NMR(CDCl$_3$, TMS) δ(ppm): 2.05-2.11(2H, m), 2.13-2.19(2H, m), 2.20-2.28(2H, m), 3.49-2.59(2H, m), 4.57(2H, dt).

Production Example 40

2.3 g of 2-(2-bromoethyl)-2-(3,3,3-trifluoropropyl)malononitrile (hereinafter, referred to as the present compound (40)) was obtained according to Production Example 18 except that 5.6 g of 1,2-dibromoethane was used in place of cyclopropylmethyl bromide.

The present compound (40):
$^1$H-NMR(CDCl$_3$, TMS) δ(ppm): 2.23-2.30(2H, m), 2.49-2.58(4H, m), 3.59(2H, t).

Production Example 41

2.3 g of 2-(3-bromopropyl)-2-(3,3,3-trifluoropropyl)malononitrile (hereinafter, referred to as the present compound (41)) was obtained according to Production Example 18 except that 5.6 g of 1,3-dibromopropane was used in place of cyclopropylmethyl bromide.

The present compound (41):
$^1$H-NMR(CDCl$_3$, TMS) δ(ppm): 2.16-2.30(6H, m), 2.47-2.59(2H, m), 3.51(2H, t).

Production Example 42

6.0 g of 2-(4-pentenyl)-2-(3,3,3-trifluoropropyl)malononitrile (hereinafter, referred to as the present compound (42)) was obtained according to Production Example 18 except that 7.2 g of 5-bromo-1-pentene was used in place of cyclopropylmethyl bromide.

The present compound (42):
$^1$H-NMR(CDCl$_3$, TMS) δ(ppm): 1.78-1.85(2H, m), 1.97-2.01(2H, m), 2.18-2.23(4H, m), 2.46-2.57(2H, m), 5.06-5.12(2H, m), 5.72-5.82(1H, m).

Production Example 43

400 mg of 2-(2,2-dimethylpropyl)malononitrile was dissolved in 5 ml of N,N-dimethylformamide and then cooled in an ice bath. To this was added 120 mg of sodium hydride (60% oil). After generation of hydrogen gas ceased, 750 mg of 1-bromo-3,3,3-trifluoropropane was added dropwise and the mixture was stirred at room temperature for 12 hours. Thereafter, ice water and ethyl acetate were added to the reaction mixture. The mixture was stirred and then separated into layers. The aqueous layer was extracted with ethyl acetate. The organic layers were combined, washed successively with water and aqueous saturated sodium chloride, dried over anhydrous magnesium sulfate, and then concentrated under reduced pressure. The residue was subjected to silica gel column chromatography to obtain 437 mg of 2-(2,2-dimethylpropyl)-2-(3,3,3-trifluoropropyl)malononitrile (hereinafter, referred to as the present compound (43)).

The present compound (43):
$^1$H-NMR(CDCl$_3$, TMS) δ(ppm): 1.21(9H, s), 1.92(2H, s), 2.19-2.23(2H, m), 2.49-2.61(2H, m).

Production Example 44

0.20 of 2-(2-methyl-2-propenyl)-2-(3,3,3-trifluoropropyl)malononitrile (hereinafter, referred to as the present compound (44)) was obtained according to Production Example 1 (2) except that 0.12 g of 3-bromo-methylpropene was used in place of 1-bromo-3-chloropropane.

The present compound (44):
$^1$H-NMR(CDCl$_3$, TMS) δ(ppm): 1.97(3H, s), 2.19-2.24(2H, m), 2.48-2.60(2H, m), 2.71(2H, s), 5.16(2H, d).

Production Example 45

0.16 g of 2-(2-methylpropyl)-2-(3,3,3-trifluoropropyl)malononitrile (hereinafter, referred to as the present compound (45)) was obtained according to Production Example 1 (2) except that 0.14 g of 1-bromo-2-methylpropane was used in place of 1-bromo-3-chloropropane.

The present compound (45):
$^1$H-NMR(CDCl$_3$, TMS) δ(ppm): 1.17(6H, d), 1.89(2H, d), 2.08-2.18(1H, m), 2.19-2.23(2H, m), 2.47-2.62(2H, m).

Production Example 46

1.2 g of 2-(2,2,3,4,4,4-hexafluorobutyl)malononitrile and 1.5 g of 2-chloro-1,4-dibromo-1,1,2-trifluorobutane were dissolved in 10 ml of dimethyl sulfoxide, 0.7 g of potassium carbonate was added, and the mixture was stirred at room temperature for 5 hours. Thereafter, dilute hydrochloric acid was added to the reaction mixture, followed by extraction with ethyl acetate. The organic layer was washed successively with water and aqueous saturated sodium chloride, dried over anhydrous magnesium sulfate, and then concentrated under reduced pressure. The residue was subjected to silica gel column chromatography to obtain 0.14 g of 2-(4-bromo-3-chloro-3,4,4-trifluorobutyl)-2-(2,2,3,4,4,4-hexafluorobutyl)malononitrile (hereinafter, referred to as the present compound (46)).

The present compound (46):
$^1$H-NMR(CDCl$_3$, TMS) δ(ppm): 2.39-2.93(6H, m), 4.86-5.02(1H, m).

Production Example 47

0.56 g of 2-(2,2,3,3,4,4,5,5-octafluoropentyl)malononitrile and 0.30 g of allyl bromide were dissolved in 5 ml of dimethyl sulfoxide, 0.28 g of potassium carbonate was added, and the mixture was stirred at room temperature for 5 hours. Thereafter, dilute hydrochloric acid was added to the reaction mixture, followed by extraction with ethyl acetate. The organic layer was washed successively with water and aqueous saturated sodium chloride, dried over anhydrous magnesium sulfate, and then concentrated under reduced pressure. The residue was subjected to silica gel column chromatography to obtain 0.15 g of 2-(allyl)-2-(2,2,3,3,4,4,5,5-octafluoropentyl)malononitrile (hereinafter, referred to as the present compound (47)).

The present compound (47):
$^1$H-NMR(CDCl$_3$, TMS) δ(ppm): 2.75(2H, t), 2.87(2H, d), 5.47-5.72(2H, m), 5.86-6.21(2H, m).

Production Example 48

1.0 g of 2-(4,4,4-trifluorobutyl)-2-(3,3,3-trifluoropropyl)malononitrile (hereinafter, referred to as the present compound (48)) was obtained according to Production Example 18 except that 1.2 g of 1-iodo-4,4,4-trifluorobutane was used in place of cyclopropylmethyl bromide.

The present compound (48):
$^1$H-NMR(CDCl$_3$, TMS) δ(ppm): 2.00-2.11(4H, m), 2.21-2.32(4H, m), 2.48-2.59(2H, m).

Production Example 49

14.6 g of 2,2,3,3,4,4,5,5-octafluoropentyl trifluoromethanesulfonate was dissolved in 30 ml of dimethyl sulfoxide, and 5.5 g of potassium carbonate was added. Further, 2.6 g of malononitrile dissolved in 10 ml of dimethyl sulfoxide was added dropwise, and the mixture was stirred at room temperature for 3 hours. Further, 7.0 g of 2,2,3,3,4,4,5,5-octafluoropentyl trifluoromethanesulfonate and 2.7 g of potassium carbonate were added, and the mixture was stirred for 1 hour. Thereafter, dilute hydrochloric acid was added to the reaction mixture, followed by extraction with ethyl acetate. The organic layer was washed successively with water and aqueous saturated sodium chloride, dried over anhydrous magnesium sulfate, and then concentrated under reduced pressure. The residue was subjected to silica gel column chromatography. The resulting fraction was concentrated and washed with chloroform to obtain 0.13 g of 2,2-bis(2,2,3,3,4,4,5,5-octafluoropentyl)malononitrile (hereinafter, referred to as the present compound (49)).

The present compound (49):
$^1$H-NMR(CDCl$_3$, TMS) δ(ppm): 3.00(4H, t), 6.07(2H, tt).

Production Example 50

7.5 g of malononitrile was dissolved in 50 ml of N,N-dimethylformamide and 10.4 g of potassium carbonate was added. The mixture was stirred at room temperature for 1 hour, 10.0 g of 2,2,3,3-tetrafluoropropyl trifluoromethanesulfonate dissolved in 20 ml of N,N-dimethylformamide was added dropwise, and the mixture was stirred overnight. Thereafter, the reaction mixture was poured to water and extracted with diethyl ether. The organic layer was washed successively with water and aqueous saturated sodium chloride, dried over anhydrous magnesium sulfate, and then concentrated under reduced pressure. The residue was subjected to silica gel column chromatography. The resulting fraction was washed with chloroform to obtain 0.08 g of 2,2-bis(2,2,3,3-tetrafluoropropyl)malononitrile (hereinafter, referred to as the present compound (50)).

The present compound (50):
$^1$H-NMR(CDCl$_3$, TMS) δ(ppm): 2.89(4H, t), 5.88(2H, tt).

Production Example 51

1.4 g of 2-(2,2,3,3,4,4,5,5-octafluoropentyl)malononitrile and 1.0 g of iodopentane were dissolved in 10 ml of dimethyl sulfoxide, 0.70 g of potassium carbonate was added, and the mixture was stirred at room temperature for 3 hours. Thereafter, dilute hydrochloric acid was added to the reaction mixture, followed by extraction with ethyl acetate. The organic layer was washed successively with water and aqueous saturated sodium chloride, dried over anhydrous magnesium sulfate, and then concentrated under reduced pressure. The residue was subjected to silica gel column chromatography to obtain 0.90 g of 2-(2,2,3,3,4,4,5,5-octafluoropentyl)-2-pentylmalononitrile (hereinafter, referred to as the present compound (51)).

The present compound (51):
$^1$H-NMR(CDCl$_3$, TMS) δ(ppm): 0.94(3H, t), 1.37-1.45(4H, m), 1.71-1.79(2H, m), 2.07-2.11(2H, m), 2.76(2H, t), 6.06(1H, tt).

Production Example 52

3.2 g of 2-(3,3,3-trifluoropropyl)malononitrile, 7.0 g of dibromomethane and 5.5 g of potassium carbonate were added to 40 ml of dimethyl sulfoxide, and the mixture was stirred at room temperature for 18 hours. Thereafter, the reaction mixture was poured to water and then extracted with diethyl ether. The organic layer was washed successively with water and aqueous saturated sodium chloride, dried over anhydrous sodium sulfate and then concentrated under reduced pressure. The residue was subjected to silica gel column chromatography to obtain 3.4 g of 2-bromomethyl-2-(3,3,3-trifluoropropyl)malononitrile (hereinafter, referred to as the present compound (52)).

The present compound (52):
$^1$H-NMR(CDCl$_3$, TMS) δ(ppm): 2.32-2.38(2H, m), 2.50-2.59(2H, m), 3.72(2H, s).

Production Example 53

2.0 g of 2-(3,3,3-trifluoropropyl)malononitrile and 4.7 g of 2,2,3,3,4,4,5,5,5-nonafluoropentyl trifluoromethanesulfonate were dissolved in 10 ml of N,N-dimethylformamide, 2.0 g of potassium carbonate was added, and the mixture was stirred at 60° C. for 4 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.87 g of 2-(2,2,3,3,4,4,5,5,5-nonafluoropentyl)-2-(3,3,3-trifluoropropyl)malononitrile (hereinafter, referred to as the present compound (5.3)).

The present compound (53):
¹H-NMR(CDCl₃, TMS) δ(ppm): 2.36-2.41(2H, m), 2.56-2.67(2H, m), 2.84(2H, t).

Production Example 54

1.6 g of 2-(3,3,3-trifluoropropyl)malononitrile and 3.1 g of 1,2-dichloro-4-iodo-1,1,2-trifluorobutane were dissolved in 5 ml of dimethyl sulfoxide, 1.4 g of potassium carbonate was added, and the mixture was stirred at room temperature for 6 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 1.9 g of 2-(3,4-dichloro-3,4,4-trifluorobutyl)-2-(3,3,3-trifluoropropyl)malononitrile (hereinafter, referred to as the present compound (54)).

The present compound (54):
¹H-NMR(CDCl₃, TMS) δ(ppm): 2.28-2.61(7H, m), 2.71-2.80(1H, m).

Production Example 55

0.29 g of diethylaminosulfur trifluoride was dissolved in 5 ml of chloroform and thereto was added dropwise at 0° C. 0.40 g of 2-(5-hydroxypentyl)-2-(3,3,3-trifluoropropyl)malononitrile dissolved in 3 ml of chloroform. The mixture was stirred at room temperature for 9 hours. Thereafter, water was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.12 g of 2-(5-fluoropentyl)-2-(3,3,3-trifluoropropyl)malononitrile (hereinafter, referred to as the present compound (55)).

The present compound (55):
¹H-NMR(CDCl₃, TMS) δ(ppm): 1.54-1.61(2H, m), 1.70-1.84(4H, m), 1.99-2.03(2H, m), 2.19-2.23(2H, m), 2.46-2.58 (2H,m), 4.48(2H, dt).

Production Example 56

0.66 g of malononitrile and 9.7 g of 1-iodo-3,4,4,4-tetrafluoro-3-trifluoromethylbutane were dissolved in 10 ml of ethylene glycol dimethyl ether, 4.1 g of potassium carbonate was added, and the mixture was stirred at room temperature for 15 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.04 g of 2,2-bis(3,4,4,4-tetrafluoro-3-trifluoromethylbutyl)malononitrile (hereinafter, referred to as the present compound (56)).

The present compound (56):
¹H-NMR(CDCl₃, TMS) δ(ppm): 2.27-2.31(4H, m), 2.47-2.57(4H, m).

Production Example 57

1.4 g of 2-(2,2,3,3,4,4,5,5-octafluoropentyl)malononitrile was dissolved in 6 ml of a solution (1 mol/L) of tetrabutylammonium fluoride in tetrahydrofuran and then cooled to 0° C. Thereto 1.1 g of 2-bromo-3,3,3-trifluoropropene dissolved in 3 ml of tetrahydrofuran was added dropwise, and the mixture was stirred at room temperature for 8 hours and at 60° C. for 5 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.02 g of 2-(2,2,3,3,4,4,5,5-octafluoropentyl)-2-(2-bromo-3,3,3-trifluoropropyl)malononitrile (hereinafter, referred to as the present compound (57)).

The present compound (57):
¹H-NMR(CDCl₃, TMS) δ(ppm): 2.71-2.98(4H, m), 4.33-4.46(1H, m), 6.03(1H, tt).

Production Example 58

1.6 g of 2-(3,3,3-trifluoropropyl)malononitrile was dissolved in 20 ml of a solution (1 mol/L) of tetrabutylammonium fluoride in tetrahydrofuran, 5 ml of 2-chloro-3,3,3-trifluoropropene was added thereto at 0° C., and the mixture was stirred at room temperature for 3 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.22 g of 2-(2-chloro-3,3,3-trifluoropropyl)-2-(3,3,3-trifluoropropyl)malononitrile (hereinafter, referred to as the present compound (58)).

The present compound (58):
¹H-NMR(CDCl₃, TMS) δ(ppm): 2.31-2.40(2H, m), 2.54-2.66(4H, m), 4.47-4.52(1H, m).

Production Example 59

0.15 g of 2-(2,2,3,3,4,4,5,5-octafluoropentyl)-2-(3-oxobutyl)malononitrile was added to 2 ml of diethylaminosulfur trifluoride cooled to 0° C., and the mixture was stirred at room temperature for 8 hours. Thereafter, the reaction mixture was added to water and then extracted with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.12 g of 2-(3,3-difluorobutyl)-2-(2,2,3,3,4,4,5,5-octafluoropentyl)malononitrile (hereinafter, referred to as the present compound (59)).

The present compound (59):
¹H-NMR(CDCl₃, TMS) δ(ppm): 1.72(3H, t), 2.21-2.36 (4H, m), 2.80(2H, t), 6.03(1H, tt).

Production Example 60

1.1 g of diethylaminosulfur trifluoride was dissolved in 3 ml of chloroform, and thereto 0.80 g of 2-(5-oxopentyl)-2-(3,3,3-trifluoropropyl)malononitrile dissolved in 3 ml of chloroform was added dropwise at 0° C. The mixture was stirred at room temperature for 7 hours. Thereafter, the reaction mixture was added to water and then extracted with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.45 g of 2-(5,5-difluoropentyl)-2-(3,3,3-trifluoropropyl)malononitrile (hereinafter, referred to as the present compound (60)).

The present compound (60):
$^1$H-NMR(CDCl$_3$, TMS) δ(ppm): 1.58-1.66(2H,m), 1.75-1.83(2H, m), 1.85-1.98(2H, m), 1.99-2.04(2H, m), 2.19-2.23 (2H, m), 2.46-2.58(2H, m), 5.85(1H, tt).

Production Example 61

1.4 g of 2-(2,2,3,3,4,4,5,5-octafluoropentyl)malononitrile and 4.0 g of 2,2,3,3-tetrafluoropropyl trifluoromethanesulfonate were dissolved in 10 ml of ethylene glycol dimethyl ether, 1.4 g of potassium carbonate was added, and the mixture was stirred at room temperature for 8 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.36 g of 2-(2,2,3,3,4,4,5,5-octafluoropentyl)-2-(2,2,3,3-tetrafluoropropyl)malononitrile (hereinafter, referred to as the present compound (61)).

The present compound (61):
$^1$H-NMR(CDCl$_3$, TMS) δ(ppm): 2.91(2H, t), 2.99(2H, t), 5.89(1H, tt), 6.06(1H, tt).

Production Example 62

1.4 g of 2-(2,2,3,3,4,4,5,5-octafluoropentyl)malononitrile and 2.2 g of 1,3-dibromobutane were dissolved in 10 ml of dimethyl sulfoxide, 0.83 g of potassium carbonate was added, and the mixture was stirred at room temperature for 4 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 1.2 g of 2-(3-bromobutyl)-2-(2,2,3,3,4,4,5,5-octafluoropentyl)malononitrile (hereinafter, referred to as the present compound (62)).

The present compound (62):
$^1$H-NMR(CDCl$_3$, TMS) δ(ppm): 1.81(3H, d), 2.14-2.47 (4H, m), 2.83(2H, t), 4.13-4.18(1H, m), 6.07(1H, tt).

Production Example 63

3.3 g of 2-(3,3,3-trifluoropropyl)malononitrile and 8.6 g of 1,4-dibromobutane were dissolved in 20 ml of dimethyl sulfoxide, 3.0 g of potassium carbonate was added, and the mixture was stirred at room temperature for 2 hours. Thereafter, dilute hydrochloric acid was added to the reaction mixture, followed by extraction with methyl tert-butyl ether. The organic layer was washed successively with water, aqueous saturated sodium hydrogen carbonate and aqueous sodium chloride, dried over anhydrous magnesium sulfate, and then concentrated under reduced pressure. The residue was subjected to silica gel column chromatography to obtain 3.2 g of 2-(4-bromobutyl)-2-(3,3,3-trifluoropropyl)malononitrile (hereinafter, referred to as the present compound (63)).

The present compound (63):
$^1$H-NMR(CDCl$_3$, TMS) δ(ppm): 1.85-1.93(2H, m), 1.95-2.04(4H, m), 2.18-2.23(2H, m), 2.42-2.55(2H, m), 3.41(2H, t).

Production Example 64

1.2 g of 2-(3-oxobutyl)-2-(3,3,3-trifluoropropyl)malononitrile was added to 1.6 g of diethylaminosulfur trifluoride cooled to 0° C. The mixture was adjusted to room temperature and stirred for 3 hours. Thereafter, the reaction mixture was added to water and then extracted with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.85 g of 2-(3,3-difluorobutyl)-2-(3,3,3-trifluoropropyl)malononitrile (hereinafter, referred to as the present compound (64)).

The present compound (64):
$^1$H-NMR(CDCl$_3$, TMS) δ(ppm): 1.68(3H, m), 2.18-2.27 (6H, m), 2.43-2.56(2H, m).

Production Example 65

3.2 g of 2-(2,2,3,3,4,4,5,5-octafluoropentyl)malononitrile and 8.6 g of 1,3-dibromopropane were dissolved in 20 ml of dimethyl sulfoxide, 3.0 g of potassium carbonate was added, and the mixture was stirred at room temperature for 2 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 3.2 g of 2-(3-bromopropyl)-2-(2,2,3,3,4,4,5,5-octafluoropentyl)malononitrile (hereinafter, referred to as the present compound (65)).

The present compound (65):
$^1$H-NMR(CDCl$_3$, TMS) δ(ppm): 2.30(4H, m), 2.78(2H, t), 3.52(2H, t), 6.02(1H, tt).

Production Example 66

1.4 g of 2-(2,2,3,3,4,4,5,5-octafluoropentyl)malononitrile and 1.2 g of 1-iodo-4,4,4-trifluorobutane were dissolved in 5 ml of dimethyl sulfoxide, 0.83 g of potassium carbonate was added, and the mixture was stirred at room temperature for 5 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.35 g of 2-(2,2,3,3,4,4,5,5-octafluoropentyl)-2-(4,4,4-trifluorobutyl)malononitrile (hereinafter, referred to as the present compound (66)).

The present compound (66):
$^1$H-NMR(CDCl$_3$, TMS) δ(ppm): 2.01-2.13(2H, m), 2.16-2.32(4H, m), 2.78(2H, t), 6.02(1H, tt).

Production Example 67

1.4 g of 2-(2,2,3,3,4,4,5,5-octafluoropentyl)malononitrile and 1.5 g of 1,2-dichloro-4-iodo-1,1,2-trifluorobutane were dissolved in 5 ml of dimethyl sulfoxide, 0.83 g of potassium carbonate was added, and the mixture was stirred at room temperature for 9 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.05 g of 2-(3,4-dichloro-3,4,4-trifluorobutyl)-2-(2,2,3,3,4,4,5,5-octafluoropentyl)malononitrile (hereinafter, referred to as the present compound (67)).

The present compound (67):
$^1$H-NMR(CDCl$_3$, TMS) δ(ppm): 2.42-2.49(2H, m), 2.54-2.70(2H, m), 2.87(2H, t), 6.07(1H, tt).

Production Example 68

1.4 g of 2-(2,2,3,3,4,4,5,5-octafluoropentyl)malononitrile and 1.4 g of 1-iodo-3,3,4,4,4-pentafluorobutane were dissolved in 5 ml of dimethyl sulfoxide, 0.83 g of potassium carbonate was added, and the mixture was stirred at room temperature for 7 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.45 g of 2-(2,2,3,3,4,4,5,5-octafluoropentyl)-2-(3,3,4,4,4-pentafluorobutyl)malononitrile (hereinafter, referred to as the present compound (68)).

The present compound (68):
$^1$H-NMR(CDCl$_3$, TMS) δ(ppm): 2.40-2.60(4H, m), 2.87 (2H, t), 6.07(1H, tt).

Production Example 69

1.4 g of 2-(2,2,3,3,4,4,5,5-octafluoropentyl)malononitrile was dissolved in 10 ml of a solution (1 mol/L) of tetrabutylammonium fluoride in tetrahydrofuran and thereto 5 ml of 2-chloro-3,3,3-trifluoropropene was added at 0° C. The mixture was then stirred at room temperature for 3 days. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.03 g of 2-(2-chloro-3,3,3-trifluoropropyl)-2-(2,2,3,3,4,4,5,5-octafluoropentyl)malononitrile (hereinafter, referred to as the present compound (69)).

The present compound (69):
$^1$H-NMR(CDCl$_3$, TMS) δ(ppm): 2.67-2.80(2H, m), 2.86-3.06(2H, m), 4.50-4.58(1H, m), 6.07(1H, tt).

Production Example 70

1.2 g of 2-(3-oxopentyl)-2-(3,3,3-trifluoropropyl)malononitrile was added to 1.6 g of diethylaminosulfur trifluoride cooled to 0° C., and the mixture was stirred at room temperature for 5 hours. Thereafter, the reaction mixture was added to water and then extracted with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.15 g of 2-(3,3-difluoropentyl)-2-(3,3,3-trifluoropropyl)malononitrile (hereinafter, referred to as the present compound (70)).

The present compound (70):
$^1$H-NMR(CDCl$_3$, TMS) δ(ppm): 1.07(3H, t), 1.87-2.01 (2H, m), 2.16-2, 2.28 (6H, m), 2.48-2.60(2H, m).

Production Example 71

1.4 g of 2-(2,2,3,3,4,4,5,5-octafluoropentyl)malononitrile and 1.6 g of 1-iodo-3,3,4,4,5,5,5-heptafluoropentane were dissolved in 5 ml of ethylene glycol dimethyl ether, 0.83 g of potassium carbonate was added, and the mixture was stirred at room temperature for 8 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.75 g of 2-(3,3,4,4,5,5,5-heptafluoropentyl)-2-(2,2,3,3,4,4,5,5-octafluoropentyl)malononitrile (hereinafter, referred to as the present compound (71)).

the present compound (71):
$^1$H-NMR(CDCl$_3$, TMS) δ(ppm): 2.41-2.45(2H, m), 2.50-2.64(2H, m), 2.87 (2H, t), 6.07(1H, tt).

Production Example 72

1.4 g of 2-(2,2,3,3,4,4,5,5-octafluoropentyl)malononitrile and 1.4 g of bromomethylcyclopropane were dissolved in 10 ml of dimethyl sulfoxide, 1.4 g of potassium carbonate was added, and the mixture was stirred at room temperature for 2 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.35 g of 2-cyclopropylmethyl-2-(2,2,3,3,4,4,5,5-octafluoropentyl)malononitrile (hereinafter, referred to as the present compound (72)).

The present compound (72):
¹H-NMR(CDCl₃, TMS) δ(ppm): 0.43(2H, dd), 0.78(2H, dd), 1.06-1.13(1H, m), 2.09(2H, d), 2.81(2H, t), 6.06(1H, tt).

Production Example 73

1.4 g of 2-(2,2,3,3,4,4,5,5-octafluoropentyl)malononitrile and 1.4 g of 4-bromo-1-butene were dissolved in 10 ml of dimethyl sulfoxide, 1.4 g of potassium carbonate was added, and the mixture was stirred at room temperature for 5 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.09 g of 2-(3-butenyl)-2-(2,2,3,3,4,4,5,5-octafluoropentyl)malononitrile (hereinafter, referred to as the present compound (73)).

The present compound (73):
¹H-NMR(CDCl₃, TMS) δ(ppm): 2.18-2.22(2H, m), 21.50-2.55(2H, m), 2.79(2H, t), 5.15(2H, m), 5.78-5.87(1H, m), 6.07(1H, tt).

Production Example 74

1.4 g of 2-(2,2,3,3,4,4,5,5-octafluoropentyl)malononitrile and 1.0 g of 1-bromo-3-fluoropropane were dissolved in 10 ml of ethylene glycol dimethyl ether, 0.97 g of potassium carbonate was added, and the mixture was stirred at room temperature for 10 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.67 g of 2-(3-fluoropropyl)-2-(2,2,3,3,4,4,5,5-octafluoropentyl)malononitrile (hereinafter, referred to as the present compound (74)).

The present compound (74):
¹H-NMR(CDCl₃, TMS) δ(ppm): 2.10-2.23(2H, m), 2.27-2.31(2H, m), 2.81(2H, t), 4.58 (2H, dt), 6.07(1H, tt).

Production Example 75

1.4 g of 2-(2,2,3,3,4,4,5,5-octafluoropentyl)malononitrile and 1.3 g of 1-bromo-3,4,4-trifluoro-3-butene were dissolved in 10 ml of ethylene glycol dimethyl ether, 0.97 g of potassium carbonate was added, and the mixture was stirred at room temperature for 10 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.45 g of 2-(2,2,3,3,4,4,5,5-octafluoropentyl)-2-(3,4,4-trifluoro-3-butenyl) malononitrile (hereinafter, referred to as the present compound (75)).

The present compound (75):
¹H-NMR(CDCl₃, TMS) δ(ppm): 2.35-2.39(2H, m), 2.74-2.87(4H, m), 6.06(1H, tt).

Production Example 76

1.4 g of 2-(2,2,3,3,4,4,5,5-octafluoropentyl)malononitrile and 0.83 g of 1-bromo-2-propyne were dissolved in 10 ml of ethylene glycol dimethyl ether, 0.97 g of potassium carbonate was added, and the mixture was stirred at room temperature for 4 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.65 g of 2-(2-propynyl)-2-(2,2,3,3,4,4,5,5-octafluoropentyl)malononitrile (hereinafter, referred to as the present compound (76)).

The present compound (76):
¹H-NMR(CDCl₃, TMS) δ(ppm): 2.52(1H, t), 2.94(2H, t), 3.14(2H, d), 6.07(1H, tt).

Production Example 77

1.4 g of 2-(2,2,3,3,4,4,5,5-octafluoropentyl)malononitrile and 1.1 g of 1-bromo-3-methylbutane were dissolved in 10 ml of ethylene glycol dimethyl ether, 0.97 g of potassium carbonate was added, and the mixture was stirred at room temperature for 5 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.15 g of 2-(3-methylbutyl)-2-(2,2,3,3,4,4,5,5-octafluoropentyl)malononitrile (hereinafter, referred to as the present compound (77)).

The present compound (77):
¹H-NMR(CDCl₃, TMS) δ(ppm): 0.98(6H, d), 1.58-1.74 (3H, m), 2.08-2.12(2H, m), 2.77(2H, t), 6.06(1H, tt).

Production Example 78

1.4 g of 2-(2,2,3,3,4,4,5,5-octafluoropentyl)malononitrile and 1.1 g of 1-bromo-3-methyl-2-butene were dissolved in 10 ml of ethylene glycol dimethyl ether, 0.97 g of potassium carbonate was added, and the mixture was stirred at room temperature for 7 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.50 g of 2-(3-methyl-2-butenyl)-2-(2,2,3,3,4,4,5,5-octafluoropentyl)malononitrile (hereinafter, referred to as the present compound (78)).

The present compound (78):
¹H-NMR(CDCl₃, TMS) δ(ppm): 1.76(3H, s), 1.86(3H, s), 2.73(2H, t), 2.85(2H, d), 5.30(1H, t), 6.07(1H, tt).

Production Example 79

1.4 g of 2-(2,2,3,3,4,4,5,5-octafluoropentyl)malononitrile and 3.3 g of 2,2,3,3,4,4,4-heptafluorobutyl trifluoromethanesulfonate were dissolved in 10 ml of ethylene glycol dimethyl ether, 0.97 g of potassium carbonate was added, and the mixture was stirred at room temperature for 7 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.07 g of 2-(2,2,3,3,4,4,4-heptafluorobutyl)-2-(2,2,3,3,4,4,5,5-octafluoropentyl)malononitrile (hereinafter, referred to as the present compound (79)).

The present compound (79):
$^1$H-NMR(CDCl$_3$, TMS) δ(ppm): 3.01(4H, t), 6.07(1H, tt).

Production Example 80

1.4 g of 2-(2,2,3,3,4,4,5,5-octafluoropentyl)malononitrile and 1.3 g of 1-iodobutane were dissolved in 10 ml of ethylene glycol dimethyl ether, 0.97 g of potassium carbonate was added, and the mixture was stirred at room temperature for 7 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 1.1 g of 2-butyl-2-(2,2,3,3,4,4,5,5-octafluoropentyl)malononitrile (hereinafter, referred to as the present compound (80)).

The present compound (80):
$^1$H-NMR(CDCl$_3$, TMS) δ(ppm): 1.00(3H, t), 1.43-1.53 (2H, m), 1.69-1.77(2H, m), 2.07-2.12(2H, m), 2.72(2H, t), 6.06(1H, tt).

Production Example 81

1.4 g of 2-(2,2,3,3,4,4,5,5-octafluoropentyl)malononitrile and 3.1 g of 2,2,3,4,4,4-hexafluorobutyl trifluoromethanesulfonate were dissolved in 10 ml of ethylene glycol dimethyl ether, 0.97 g of potassium carbonate was added, and the mixture was stirred at room temperature for 7 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.06 g of 2-(2,2,3,4,4,4-hexafluorobutyl)-2-(2,2,3,3,4,4,5,5-octafluoropentyl)malononitrile (hereinafter, referred to as the present compound (81)).

The present compound (81):
$^1$H-NMR(CDCl$_3$, TMS) δ(ppm): 2.89-3.04(4H, m), 4.89-5.02(1H, m), 6.07(1H, tt).

Production Example 82

1.4 g of 2-(2,2,3,3,4,4,5,5-octafluoropentyl)malononitrile and 1.3 g of 1-iodopropane were dissolved in 10 ml of ethylene glycol dimethyl ether, 0.97 g of potassium carbonate was added, and the mixture was stirred at room temperature for 10 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 1.1 g of 2-(2,2,3,3,4,4,5,5-octafluoropentyl)-2-propylmalononitrile (hereinafter, referred to as the present compound (82)).

The present compound (82):
$^1$H-NMR(CDCl$_3$, TMS) δ(ppm): 1.10(3H, t), 1.75-1.85 (2H, m), 2.06-2.10(2H, m), 2.77(2H, t), 6.07(1H, tt).

Production Example 83

1.2 g of 2-(3,3,3-trifluoropropyl)malononitrile and 0.76 g of 4-bromomethyl-1,1-difluorocyclohexane were dissolved in 10 ml of N,N-dimethylformamide, 0.99 g of potassium carbonate was added, and the mixture was stirred at room temperature overnight. Thereafter, water was added to the reaction mixture and the mixture was extracted with ethyl acetate. The organic layer was washed successively with dilute hydrochloric acid and aqueous saturated sodium chloride, dried over anhydrous magnesium sulfate, and then concentrated under reduced pressure. The residue was subjected to silica gel column chromatography to obtain 0.51 g of 2-(4,4-difluorocyclohexyl)methyl-2-(3,3,3-trifluoropropyl)malononitrile (hereinafter, referred to as the present compound (83)).

The present compound (83):
$^1$H-NMR(CDCl$_3$, TMS) δ (ppm): 1.42-1.56(2H, m), 1.71-1.96(5H, m), 1.99-2.08(2H, m), 2.10-2.25(4H, m), 2.46-2.60 (2H, m).

Production Example 84

56 mg of 2-[2-(3,3-difluorocyclopentyl)ethyl]-2-(3,3,3-trifluoropropyl)malononitrile (hereinafter, referred to as the present compound (84)) was obtained according to Production Example 83 except that 0.17 g of 3-(2-bromoethyl)-1,1-difluorocyclopentane was used in place of 4-bromomethyl-1,1-difluorocyclohexane.

The present compound (84):
$^1$H-NMR(CDCl$_3$, TMS) δ (ppm): 1.47(1H, m), 1.63-1.85 (3H, m), 1.92-2.61(11H, m).

Production Example 85

0.26 g of 2-(4-trifluoromethylcyclohexyl)methyl]-2-(3,3,3-trifluoropropyl)malononitrile (cis/trans ratio=5/1) (hereinafter, referred to as the present compound (85)) was obtained according to Production Example 83 except that 0.20 g of 1-bromomethyl-4-trifluoromethylcyclohexane was used in place of 4-bromomethyl-1,1-difluorocyclohexane.

The present compound (85):
$^1$H-NMR(CDCl$_3$, TMS) δ (ppm): 1.10-1.22(0.33H, m), 1.36-1.49(0.33H, m), 1.51-1.85(6.34H, m), 1.90(0.33H, d), 2.00(1.67H, d), 2.24-2.40(5H, m), 2.43-2.61(2H,m).

Production Example 86

0.35 g of 2-(4-methylcyclohexyl)methyl-2-(3,3,3-trifluoropropyl)malononitrile (cis/trans ratio=2/1) (hereinafter, referred to as the present compound (86)) was obtained according to Production Example 83 except that 0.29 g of 1-bromomethyl-4-methylcyclohexane was used in place of 4-bromomethyl-1,1-difluorocyclohexane.

The present compound (86):
$^1$H-NMR(CDCl$_3$, TMS) δ (ppm): 0.90(1H, d), 0.93(2H, d), 0.97-1.29(3H, m), 1.48-1.78(6H, m), 1.87(0.67H, d), 1.91-2.00(2.33H, m), 2.16-2.24(2H,m), 2.45-2.59(2H, m).

Production Example 87

0.10 g of cis-2-(3-difluoromethylcyclohexyl)methyl]-2-(3,3,3-trifluoropropyl)malononitrile (hereinafter, referred to as the present compound (87)) was obtained according to Production Example 60 except that 0.18 g of cis-2-(3-formyl-cyclohexyl)methyl-2-(3,3,3-trifluoropropyl)malononitrile was used in place of 2-(5-oxopentyl)-2-(3,3,3-trifluoropropyl)malononitrile.

The present compound (87):
$^1$H-NMR(CDCl$_3$, TMS) δ (ppm): 0.97-1.49(4H, m), 1.78-2.13(8H, m), 2.19-2.29(2H, m), 2.47-2.62(2H, m), 5.58(1H, dt).

Production Example 88

0.12 g of cis-2-(3-fluoromethylcyclohexyl)methyl]-2-(3,3,3-trifluoropropyl)malononitrile (hereinafter, referred to as the present compound (88)) was obtained according to Production Example 55 except that 0.32 g of cis-2-(3-hydroxymethylcyclohexyl)methyl-2-(3,3,3-trifluoropropyl)malononitrile was used in place of 2-(5-hydroxypentyl)-2-(3,3,3-trifluoropropyl)malononitrile.

The present compound (88):
$^1$H-NMR(CDCl$_3$, TMS) δ (ppm): 0.86-1.13(3H, m), 1.38 (1H, m), 1.74-2.09(8H, m), 2.16-2.26(2H, m), 2.46-2.60(2H, m), 4.17-4.37(2H, m).

Production Example 89

At 0° C., 18.6 g of trifluoromethanesulfonic anhydride was added dropwise to 10.7 g of 4,4,5,5,5-pentafluoropentanol. The mixture was stirred at room temperature for an hour and then at 80° C. for 2 hours. Thereafter, the reaction mixture was poured into ice water and then extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure to obtain 6.2 g of 4,4,5,5,5-pentafluoropentyl trifluoromethanesulfonate.

To 10 ml of ethylene glycol dimethyl ether, 6.2 g of 4,4,5,5,5-pentafluoropentyl trifluoromethanesulfonate, 1.6 g of 2-(3,3,3-trifluoropropyl)malononitrile and 1.4 g of potassium carbonate were added and the mixture was stirred at room temperature for 5 hours. Thereafter, dilute hydrochloric acid was added to the reaction mixture and the mixture was extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.65 g of 2-(4,4,5,5,5-pentafluoropentyl)-2-(3,3,3-trifluoropropyl)malononitrile (hereinafter, referred to as the present compound (89)).

The present compound (89):
$^1$H-NMR(CDCl$_3$, TMS) δ (ppm): 2.05-2.26(8H, m), 2.48-2.60(2H, m).

Production Example 90

To 2 ml of diethylaminosulfur trifluoride cooled to 0° C., 1.4 g of 2-(4-oxopentyl)-2-(3,3,3-trifluoropropyl)malononitrile was added and the mixture was stirred at room temperature for 5 hours. Thereafter, the reaction mixture was poured into water and then extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.37 g of 2-(4,4-difluoropentyl)-2-(3,3,3-trifluoropropyl)malononitrile (hereinafter, referred to as the present compound (90)).

The present compound (90):
$^1$H-NMR(CDCl$_3$, TMS) δ (ppm): 1.65(3H, t), 1.86-2.89 (6H, m), 2.20-2.24(2H, m), 2.47-2.59(2H, m).

Production Example 91

In 20 ml of acetone, 2.8 g of 2-(2,2,3,3,4,4,5,5-octafluoropentyl)malononitrile and 4.5 g of 2,2,3,3,3-pentafluoropropyl trifluoromethanesulfonate were dissolved, 2.2 g of potassium carbonate was added and the mixture was stirred at room temperature for 8 hours. Thereafter, dilute hydrochloric acid was added to the reaction mixture and the mixture was extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.10 g of 2-(2,2,3,3,4,4,5,5-octafluoropentyl)-2-(2,2,3,3,3-pentafluoropropyl)malononitrile (hereinafter, referred to as the present compound (91)).

The present compound (91):
$^1$H-NMR(CDCl$_3$, TMS) δ (ppm): 2.96(2H, t), 3.00(2H, t), 6.07(1H, tt).

Production Example 92

In 20 ml of acetone, 2.1 g of 2-(2,2,3,3,3-pentafluoropropyl)malononitrile and 4.5 g of 2,2,3,3,3-pentafluoropropyl trifluoromethanesulfonate were dissolved, 2.2 g of potassium carbonate was added and the mixture was stirred at room temperature for 10 hours. Thereafter, dilute hydrochloric acid was added to the reaction mixture and the mixture was extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.05 g of 2,2-bis (2,2,3,3,3-pentafluoropropyl)malononitrile (hereinafter, referred to as the present compound (93)).

The present compound (93):
$^1$H-NMR(CDCl$_3$, TMS) δ (ppm): 2.96(4H, t).

Production Example 93

In 50 ml of acetone, 2.0 g of 2-(2,2,3,4,4,4-hexafluorobutyl)malononitrile and 5.3 g of 2,2,3,4,4,4-hexafluorobutyl trifluoromethanesulfonate were dissolved, 1.9 g of potassium carbonate was added and the mixture was stirred at room temperature for 10 hours. Thereafter, dilute hydrochloric acid was added to the reaction mixture and the mixture was extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.05 g of 2,2-bis (2,2,3,4,4,4-hexafluorobutyl)malononitrile (hereinafter, referred to as the present compound (95)).

The present compound (95):
$^1$H-NMR(CDCl$_3$, TMS) δ (ppm): 2.84-3.06(4H, m), 4.85-5.05(2H, m).

Production Example 94

In 50 ml of acetone, 3.2 g of 2-(2,2,3,3,3-pentafluoropropyl)malononitrile and 7.2 g of 5-iodo-1,1,1,2,2,3,3-heptafluoropentane were dissolved, 3.2 g of potassium carbonate was added and the mixture was stirred at room temperature for 10 hours. Thereafter, dilute hydrochloric acid was added to the reaction mixture and the mixture was extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.05 g of 2-(3,3,4,4,5,5,5-heptafluoropentyl)-2-(2,2,3,3,3-pentafluoropropyl)malononitrile (hereinafter, referred to as the present compound (96)):

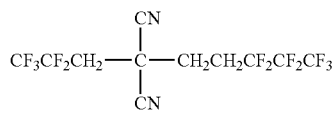

The present compound (96):
$^1$H-NMR(CDCl$_3$, TMS) δ (ppm): 2.41-2.45(2H, m), 2.50-2.64(2H, m), 2.82(2H, t).

The compounds of the present invention will be shown specifically below, but the present invention is not limited to them.

A compound represent by the formula (I):

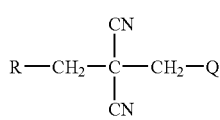

Combinations of R and Q in the formula will be shown in Table 1 to Table 4.

TABLE 1

| Compound No. | R | Q |
|---|---|---|
| 1 | CH$_2$CF$_3$ | CH$_2$CH$_2$Cl |
| 2 | CH$_2$CF$_3$ | CH(CH$_3$)CH$_2$Cl |
| 3 | CH$_2$CF$_3$ | CH$_2$CH$_2$CH$_2$Cl |

TABLE 1-continued

| Compound No. | R | Q |
|---|---|---|
| 4 | CH$_2$CF$_3$ | cyclopropyl with CCl$_2$ (CH-CCl$_2$-CH$_2$ ring) |
| 5 | CH$_2$CF$_3$ | CH$_2$CF$_3$ |
| 6 | CH$_2$CF$_3$ | CH$_3$ |
| 7 | CH$_2$CF$_3$ | CH$_2$CH$_3$ |
| 8 | CH$_2$CF$_3$ | CH$_2$CH$_2$CH$_3$ |
| 9 | CH$_2$CF$_3$ | CH$_2$CH$_2$CH$_2$CH$_3$ |
| 10 | CH$_2$CF$_3$ | CH$_2$CH$_2$CH$_2$CH$_2$CH$_3$ |
| 11 | CH$_2$CF$_3$ | CH$_2$CH$_2$CH$_2$CH$_2$CH$_2$CH$_3$ |
| 12 | CH$_2$CF$_3$ | CH$_2$CH$_2$CH$_2$CH$_2$CH$_2$CH$_2$CH$_3$ |
| 13 | CH$_2$CF$_3$ | CH$_2$CH$_2$CH$_2$CH$_2$CH$_2$CH$_2$CH$_2$CH$_3$ |
| 14 | CH$_2$CF$_3$ | CH$_2$CH$_2$CH$_2$CH$_2$CH$_2$CH$_2$CH$_2$CH$_2$CH$_3$ |
| 15 | CH$_2$CF$_3$ | CH=CH$_2$ |
| 16 | CH$_2$CF$_3$ | CH$_2$CH=CH$_2$ |
| 17 | CH$_2$CF$_3$ | CH$_2$CF=CF$_2$ |
| 18 | CH$_2$CF$_3$ | cyclopropyl (CH-CH$_2$-CH$_2$ ring) |
| 19 | CH$_2$CF$_3$ | cyclobutyl (CH-CH$_2$-CH$_2$-CH$_2$ ring) |
| 20 | CH$_2$CF$_3$ | CF$_2$CHF$_2$ |
| 21 | CH$_2$CF$_3$ | CF$_3$ |
| 22 | CH$_2$CF$_3$ | CF$_2$CF$_3$ |
| 23 | CH$_2$CF$_3$ | CF$_2$CHFCF$_3$ |
| 24 | CH$_2$CF$_3$ | CF$_2$CF$_2$CF$_3$ |
| 25 | CH$_2$CF$_3$ | CH$_2$F |

TABLE 2

| Compound No. | R | Q |
|---|---|---|
| 26 | CH$_2$CF$_3$ | CH$_2$CF$_2$CF$_2$CF$_2$CF$_2$CF$_2$CF$_3$ |
| 27 | CH$_2$CF$_3$ | C≡CH |
| 28 | CH$_2$CF$_3$ | cyclopentyl (CH-CH$_2$-CH$_2$-CH$_2$-CH$_2$ ring) |
| 29 | CH$_2$CF$_3$ | CH$_2$CF$_2$CF$_3$ |
| 30 | CH$_2$CF$_3$ | CH$_2$CFClCBrF$_2$ |
| 31 | CH$_2$CF$_3$ | CF$_2$CF$_2$CF$_2$CHF$_2$ |
| 32 | CH$_2$CF$_3$ | CF$_2$CF$_2$CF$_2$CF$_2$CF$_2$CHF$_2$ |
| 33 | CH$_2$CF$_3$ | CH$_2$CF$_2$CF$_2$CF$_2$CF$_2$CF$_2$CF$_2$CF$_2$CF$_2$CF$_2$CF$_3$ |
| 34 | CH$_2$CF$_3$ | CH$_2$CF$_2$CF$_2$CF$_2$CF$_2$CF$_2$CF$_2$CF$_3$ |
| 35 | CH$_2$CF$_3$ | CH$_2$CF$_2$CBrF$_2$ |
| 36 | CH$_2$CF$_3$ | CH$_2$CF(CF$_3$)$_2$ |
| 37 | CH$_2$CF$_3$ | CH$_2$CF$_2$CF$_2$CF$_3$ |
| 38 | CH$_2$CF$_3$ | CH$_2$CF$_2$CF$_2$CF$_2$CF$_3$ |
| 39 | CH$_2$CF$_3$ | CH$_2$CH$_2$F |
| 40 | CH$_2$CF$_3$ | CH$_2$Br |
| 41 | CH$_2$CF$_3$ | CH$_2$CH$_2$Br |
| 42 | CH$_2$CF$_3$ | CH$_2$CH$_2$CH=CH$_2$ |
| 43 | CH$_2$CF$_3$ | C(CH$_3$)$_3$ |
| 44 | CH$_2$CF$_3$ | C(CH$_3$)=CH$_2$ |
| 45 | CH$_2$CF$_3$ | CH(CH$_3$)$_2$ |
| 46 | CF$_2$CHFCF$_3$ | CH$_2$CFClCF$_2$Br |
| 47 | CF$_2$CF$_2$CF$_2$CHF$_2$ | CH=CH$_2$ |
| 48 | CH$_2$CF$_3$ | CH$_2$CH$_2$CF$_3$ |
| 49 | CF$_2$CF$_2$CF$_2$CHF$_2$ | CF$_2$CF$_2$CF$_2$CHF$_2$ |
| 50 | CF$_2$CHF$_2$ | CF$_2$CHF$_2$ |

TABLE 3

| Compound No. | R | Q |
|---|---|---|
| 51 | $CF_2CF_2CF_2CHF_2$ | $CH_2CH_2CH_2CH_3$ |
| 52 | $CH_2CF_3$ | Br |
| 53 | $CH_2CF_3$ | $CF_2CF_2CF_2CF_3$ |
| 54 | $CH_2CF_3$ | $CH_2CFClCF_2Cl$ |
| 55 | $CH_2CF_3$ | $CH_2CH_2CH_2CH_2F$ |
| 56 | $CH_2CF(CF_3)_2$ | $CH_2CF(CF_3)_2$ |
| 57 | $CF_2CF_2CF_2CHF_2$ | $CHBrCF_3$ |
| 58 | $CH_2CF_3$ | $CHClCF_3$ |
| 59 | $CF_2CF_2CF_2CHF_2$ | $CH_2CF_2CH_3$ |
| 60 | $CH_2CF_3$ | $CH_2CF_3$ |
| 61 | $CF_2CF_2CF_2CHF_2$ | $CF_2CF_2H$ |
| 62 | $CF_2CF_2CF_2CHF_2$ | $CH_2CHBrCH_3$ |
| 63 | $CH_2CF_3$ | $CH_2CH_2CH_2Br$ |
| 64 | $CH_2CF_3$ | $CH_2CF_2CH_3$ |
| 65 | $CF_2CF_2CF_2CHF_2$ | $CH_2CH_2Br$ |
| 66 | $CF_2CF_2CF_2CHF_2$ | $CH_2CH_2CF_3$ |
| 67 | $CF_2CF_2CF_2CHF_2$ | $CH_2CFClCF_2Cl$ |
| 68 | $CF_2CF_2CF_2CHF_2$ | $CH_2CF_2CF_3$ |
| 69 | $CF_2CF_2CF_2CHF_2$ | $CHClCF_3$ |
| 70 | $CH_2CF_3$ | $CH_2CF_2CH_2CH_3$ |
| 71 | $CF_2CF_2CF_2CHF_2$ | $CH_2CF_2CF_2CF_3$ |
| 72 | $CF_2CF_2CF_2CHF_2$ | $CH\!<\!\!\begin{array}{c}CH_2\\|\\CH_2\end{array}$ |
| 73 | $CF_2CF_2CF_2CHF_2$ | $CH_2CH\!=\!CH_2$ |
| 74 | $CH_2CH_2F$ | $CF_2CF_2CF_2CHF_2$ |
| 75 | $CF_2CF_2CF_2CHF_2$ | $CH_2CF\!=\!CF_2$ |

TABLE 4

| Compound No. | R | Q |
|---|---|---|
| 76 | $CF_2CF_2CF_2CHF_2$ | $C\!\equiv\!CH$ |
| 77 | $CF_2CF_2CF_2CHF_2$ | $CH_2CH(CH_3)_2$ |
| 78 | $CF_2CF_2CF_2CHF_2$ | $CH\!=\!C(CH_3)_2$ |
| 79 | $CF_2CF_2CF_2CHF_2$ | $CF_2CF_2CF_3$ |
| 80 | $CF_2CF_2CF_2CHF_2$ | $CH_2CH_2CH_3$ |
| 81 | $CF_2CF_2CF_2CHF_2$ | $CF_2CHFCF_3$ |
| 82 | $CF_2CF_2CF_2CHF_2$ | $CH_2CH_3$ |
| 83 | $CH_2CF_3$ | cyclohexyl with $CF_2$ |
| 84 | $CH_2CF_3$ | cyclohexyl with $CF_2$ |
| 85 | $CH_2CF_3$ | cyclohexyl with $CH\!-\!CF_3$ (cis/trans = 5/1 mixture) |
| 86 | $CH_2CF_3$ | cyclohexyl with $CH\!-\!CH_3$ (cis/trans = 5/1 mixture) |

TABLE 4-continued

| Compound No. | R | Q |
|---|---|---|
| 87 | $CH_2CF_3$ | cyclohexyl with $CHF_2$ (cis form) |
| 88 | $CH_2CF_3$ | cyclohexyl with $CH_2F$ (cis form) |
| 89 | $CH_2CF_3$ | $CH_2CH_2CF_2CF_3$ |
| 90 | $CH_2CF_3$ | $CH_2CH_2CF_2CH_3$ |
| 91 | $CF_2CF_3$ | $CF_2CF_2CF_2CHF_2$ |
| 92 | $CH_2CF_2CF_3$ | $CH_2CF_2CF_3$ |
| 93 | $CF_2CF_3$ | $CF_2CF_3$ |
| 94 | $CH_2CF_3$ | $CF_2CF\!=\!CF_2$ |
| 95 | $CF_2CHFCF_3$ | $CF_2CHFCF_3$ |

Then, for production of an intermediate of the present compound, Reference Production Examples will be described.

Reference Production Example 1

$$CF_3CH_2CH_2\!-\!Br \;+\; \begin{array}{c}CN\\|\\CH_2\\|\\CN\end{array} \longrightarrow CF_3CH_2CH_2\!-\!\begin{array}{c}CN\\|\\CH\\|\\CN\end{array}$$

27.6 g of malononitrile was dissolved in 50 ml of N,N-dimethylformamide, 27.6 g of potassium carbonate was added, and the mixture was stirred at room temperature for 1 hour. Thereafter, a mixture of 17.7 g of 1-bromo-3,3,3-trifluoropropane and 20 ml of N,N-dimethylformamide was added thereto and the mixture was further stirred for 1 hour. Thereafter, the reaction mixture was poured to water and then extracted with diethyl ether. The organic layer was washed successively with water and aqueous saturated sodium chloride, dried over anhydrous magnesium sulfate, and then concentrated under reduced pressure. The residue was subjected to silica gel column chromatography to obtain 11.3 g of 2-(3,3,3-trifluoropropyl)malononitrile.

2-(3,3,3-trifluoropropyl)malononitrile:
$^1$H-NMR(CDCl$_3$, TMS) δ(ppm): 2.32-2.42(2H,m), 2.43-2.52(2H,m), 3.91(1H,t).

Reference Production Example 2

$$CHF_2CF_2CH_2\!-\!OH \;+\; F_3C\!-\!\underset{\underset{O}{\|}}{\overset{\overset{O}{\|}}{S}}\!-\!O\!-\!\underset{\underset{O}{\|}}{\overset{\overset{O}{\|}}{S}}\!-\!CF_3 \longrightarrow$$

-continued

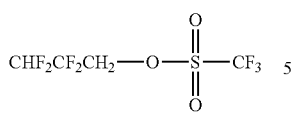

100 ml of trifluoromethanesulfonic anhydride was added dropwise to 79.2 g of 2,2,3,3-tetrafluoropropanol at 0° C. Then, the mixture was stirred at room temperature for 1 hour and at 60° C. for 3 hours. Thereafter, the reaction mixture was poured to ice water and then extracted with diethyl ether. The organic layer was washed successively with water and aqueous saturated sodium chloride, dried over anhydrous magnesium sulfate, and then concentrated under reduced pressure to obtain 100 g of 2,2,3,3-tetrafluoropropyl trifluoromethanesulfonate.

2,2,3,3-hexafluoropropyl trifluoromethanesulfonate:
$^1$H-NMR(CDCl$_3$, TMS) δ(ppm): 4.73(2H, t), 5.97(1H, tt).

Reference Production Example 3

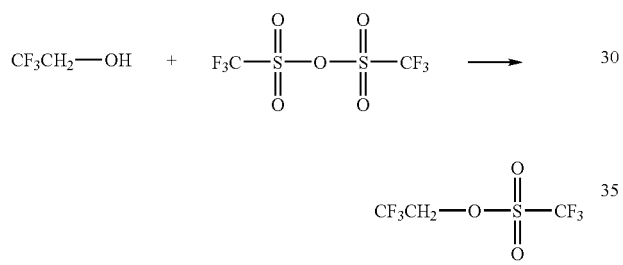

1.2 g of 2,2,2-pentafluoroethyl trifluoromethanesulfonate was obtained according to Reference Production Example 2 except that 2.0 g of 2,2,2-trifluoroethanol was used in place of 2,2,3,3-tetrafluoropropanol.

2,2,2-trifluoroethyl trifluoromethanesulfonate:
$^1$H-NMR(CDCl$_3$, TMS) δ(ppm): 4.71(2H, q).

Reference Production Example 4

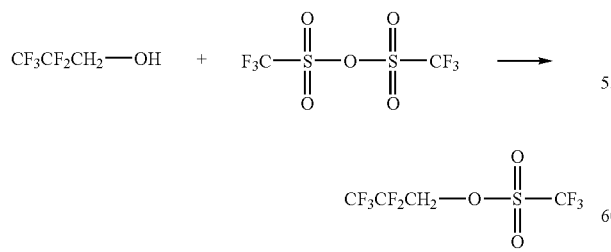

4.1 g of 2,2,3,3,3-pentafluoropropyl trifluoromethanesulfonate was obtained according to Reference Production Example 2 except that 4.8 g of 2,2,3,3,3-pentafluoropropanol was used in place of 2,2,3,3-tetrafluoropropanol.

2,2,3,3,3-pentafluoropropyl trifluoromethanesulfonate:
$^1$H-NMR(CDCl$_3$, TMS) δ(ppm): 4.72(2H, t).

Reference Production Example 5

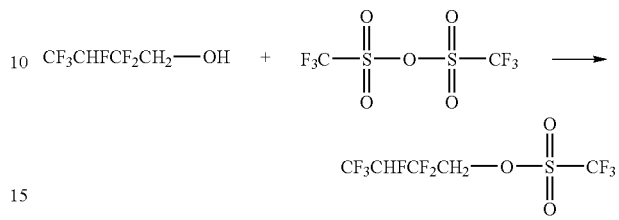

16.5 g of 2,2,3,4,4,4-hexafluorobutyl trifluoromethanesulfonate was obtained according to Reference Production Example 2 except that 14.1 g of 2,2,3,4,4,4-hexafluorobutanol was used in place of 2,2,3,3-tetrafluoropropanol.

2,2,3,4,4,4-hexafluorobutyl trifluoromethanesulfonate:
$^1$H-NMR(CDCl$_3$, TMS) δ(ppm): 4.71-4.79(2H, m), 4.92-5.11(1H, m).

Reference Production Example 6

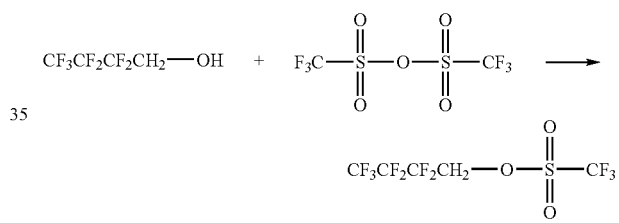

10 g of 2,2,3,3,4,4,4-heptafluorobutyl trifluoromethanesulfonate ester was obtained according to Reference Production Example 2 except that 8.0 g of 2,2,3,3,4,4,4-heptafluorobutanol was used in place of 2,2,3,3-tetrafluoropropanol.

2,2,3,3,4,4,4-heptafluorobutyl trifluoromethanesulfonate:
$^1$H-NMR(CDCl$_3$, TMS) δ(ppm): 4.80(2H, t).

Reference Production Example 7

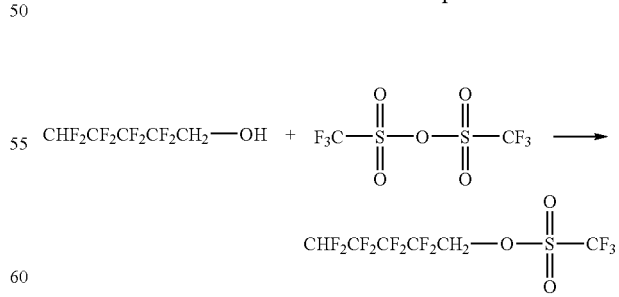

187 g of 2,2,3,3,4,4,5,5-octafluoropentyl trifluoromethanesulfonate was obtained according to Reference Production Example 2 except that 139 g of 2,2,3,3,4,4,5,5-octafluoropentanol was used in place of 2,2,3,3-tetrafluoropropanol.

2,2,3,3,4,4,5,5-octafluoropentyl trifluoromethanesulfonate:

$^1$H-NMR(CDCl$_3$, TMS) δ(ppm): 4.82(2H, m), 6.04(1H, tt).

Reference Production Example 8

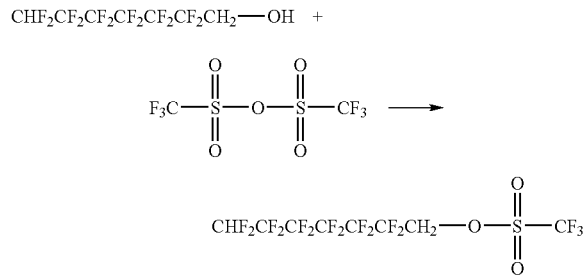

20.5 g of 2,2,3,3,4,4,5,5,6,6,7,7-dodecafluoroheptyl trifluoromethanesulfonate was obtained according to Reference Production Example 2 except that 16.6 g of 2,2,3,3,4,4,5,5,6,6,7,7-dodecafluoroheptanol was used in place of 2,2,3,3-tetrafluoropropanol.

2,2,3,3,4,4,5,5,6,6,7,7-dodecafluoroheptyl trifluoromethanesulfonate:

$^1$H-NMR(CDCl$_3$, TMS) δ(ppm): 4.83(2H, t), 6.07(1H, tt).

Reference Production Example 9

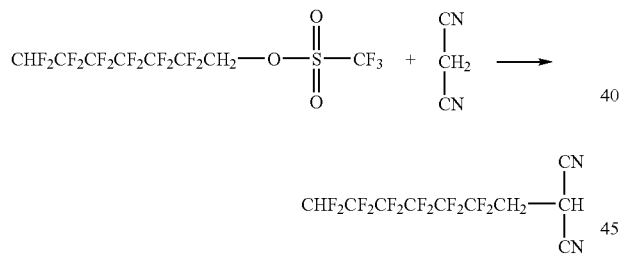

14.6 g of 2,2,3,3,4,4,5,5,6,6,7,7-dodecafluoroheptyl trifluoromethanesulfonate was dissolved in 20 ml of dimethyl sulfoxide, and 5.5 g of potassium carbonate was added. 2.6 g of malononitrile dissolved in 10 ml of dimethyl sulfoxide was added dropwise thereto, and the mixture was stirred at room temperature for 3 hours. The reaction mixture was poured to water and then extracted with diethyl ether. The organic layer was washed successively with water and aqueous saturated sodium chloride, dried over anhydrous magnesium sulfate, and then concentrated under reduced pressure. The residue was subjected to silica gel column chromatography to obtain 2.0 g of 2-(2,2,3,3,4,4,5,5,6,6,7,7-dodecafluoroheptyl)malononitrile.

2-(2,2,3,3,4,4,5,5,6,6,7,7-dodecafluoroheptyl)malononitrile $^1$H-NMR(CDCl$_3$, TMS) δ(ppm): 2.91(2H, dt), 4.14(1H, t), 6.05(1H, tt).

Reference Production Example 10

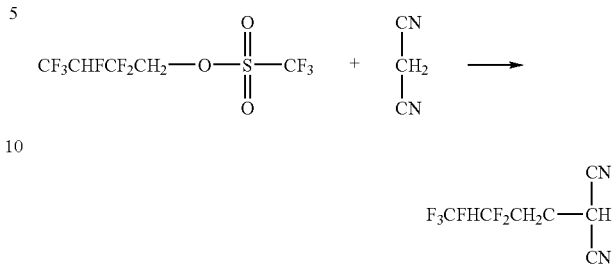

8.0 g of 2,2,3,4,4,4-hexafluorobutyl trifluoromethanesulfonate was dissolved in 15 ml of dimethyl sulfoxide, and 6.9 g of potassium carbonate was added. 5.0 g of malononitrile dissolved in 15 ml of dimethyl sulfoxide was added dropwise thereto, and the mixture was stirred at room temperature for 3 hours. The reaction mixture was poured to water and then extracted with diethyl ether. The organic layer was washed successively with water and aqueous saturated sodium chloride, dried over anhydrous magnesium sulfate, and then concentrated under reduced pressure. The residue was subjected to silica gel column chromatography to obtain 2.0 g of 2-(2,2,3,4,4,4-hexafluorobutyl)malononitrile.

2-(2,2,3,4,4,4-hexafluorobutyl)malononitrile:

$^1$H-NMR(CDCl$_3$, TMS) δ(ppm): 2.79-2.91(2H, m), 4.15 (1H, t), 4.84-5.04(1H, m).

Reference Production Example 11

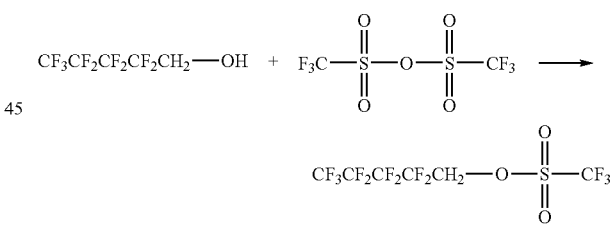

6.8 g of trifluoromethanesulfonic anhydride was added dropwise to 5.0 g of 2,2,3,3,4,4,5,5,5-nonafluoropentanol at 0° C., and the mixture was stirred at room temperature for 5 hours and at 100° C. for 3 hours. Thereafter, the reaction mixture was poured to ice water and then extracted with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure to obtain 4.7 g of 2,2,3,3,4,4,5,5,5-nonafluoropentyl trifluoromethanesulfonate.

2,2,3,3,4,4,5,5,5-nonafluoropentyl trifluoromethanesulfonate:

$^1$H-NMR(CDCl$_3$, TMS) δ(ppm): 4.82(2H, t).

Reference Production Example 12

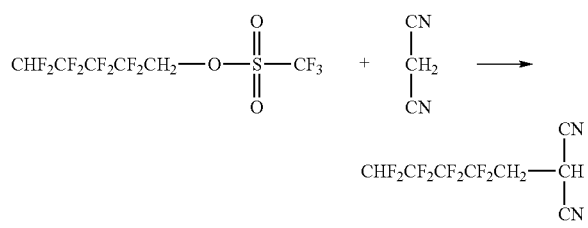

15 g of (2,2,3,3,4,4,5,5-octafluoropentyl)trifluoromethanesulfonic acid and 2.6 g of malononitrile were dissolved in 20 ml of dimethyl sulfoxide, 5.5 g of potassium carbonate was added, and the mixture was stirred in a water bath for 3 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 2.0 g of 2-(2,2,3,3,4,4,5,5-octafluoropentyl)malononitrile.

2-(2,2,3,3,4,4,5,5-octafluoropentyl)malononitrile:
$^1$H-NMR(CDCl$_3$, TMS) δ(ppm): 2.90(2H, dt), 4.15(1H, t), 6.06(1H, tt).

Reference Production Example 13

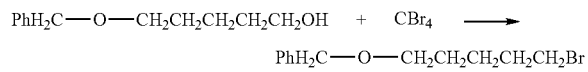

7.0 g of 5-hydroxypentyl benzyl ether and 10.6 g of triphenylphosphine were added to 50 ml of methyl tert-butyl ether and then cooled to 0° C. Further, 13.2 g of carbon tetrabromide was added and the mixture was stirred at room temperature for 3 hours. Thereafter, 100 ml of hexane was added and the mixture was concentrated under reduced pressure. The residue was subjected to silica gel column chromatography to obtain 5.5 g of 5-bromopentyl benzyl ether.

5-bromopentyl benzyl ether:
$^1$H-NMR(CDCl$_3$, TMS) δ(ppm): 1.49-1.57(2H, m), 1.61-1.68(2H, m), 1.85-1,92(2H, m), 3.41(2H, t), 2.48(2H, t), 4.50 (2H, s), 7.26-7.37(5H, m).

Reference Production Example 14

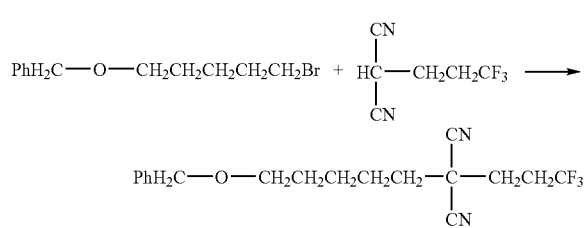

3.5 g of 2-(3,3,3-trifluoropropyl)malononitrile, 5.5 g of 5-bromopentyl benzyl ether and 0.70 g of potassium iodide were dissolved in 20 ml of dimethyl sulfoxide, 3.3 g of potassium carbonate was added, and the mixture was stirred at room temperature for 9 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 5.9 g of 2-(5-benzyloxypentyl)-2-(3,3,3-trifluoropropyl)malononitrile.

2-(5-benzyloxypentyl)-2-(3,3,3-trifluoropropyl)malononitrile:
$^1$H-NMR(CDCl$_3$, TMS) δ(ppm): 1.48-1.57(2H, m), 1.64-1.76(4H, m), 1.95-2.00(2H, m), 2.20-2.44(2H, m), 2.44-2.56 (2H, m), 3.49(2H, t), 4.50(2H, s), 7.28-7.35(5H, m).

Reference Production Example 15

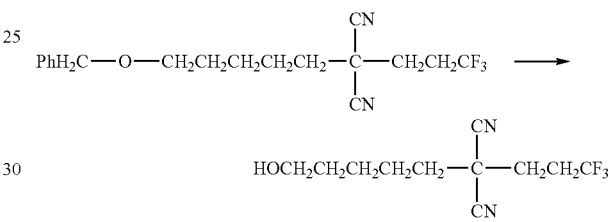

1.8 g of 2-(5-benzyloxypentyl)-2-(3,3,3-trifluoropropyl)malononitrile was added to 20 ml of acetonitrile was cooled to 0° C. To the mixture, 1.6 g of sodium iodide added and 1.3 g of trifluoroborane-diethyl ether complex dissolved in 5 ml of acetonitrile was further added dropwise. The mixture was stirred at 0° C. for 1 hour and at room temperature for 6 hours. Thereafter, water was added to the reaction mixture, followed by extraction with chloroform. The organic layer was washed successively with water and aqueous saturated sodium chloride, dried over anhydrous magnesium sulfate, and then concentrated under reduced pressure. The residue was subjected to silica gel column chromatography to obtain 0.40 g of 2-(5-hydroxypentyl)-2-(3,3,3-trifluoropropyl)malononitrile.

2-(5-hydroxypentyl)-2-(3,3,3-trifluoropropyl)malononitrile:
$^1$H-NMR(CDCl$_3$, TMS) δ(ppm): 1.26(1H, br), 1.51-1.57 (2H, m), 1.61-1.66(2H, m), 1.72-1.79(2H, m), 1.98-2.02(2H, m), 2.18-2.23(2H, m), 2.48-2.55(2H, m), 3.69(2H, t).

Reference Production Example 16

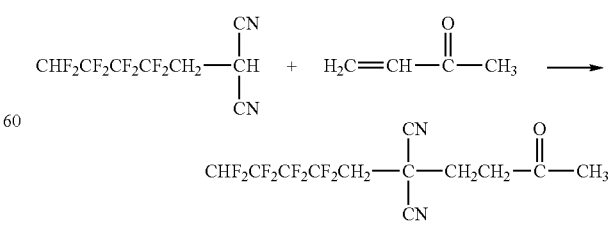

1.4 g of 2-(2,2,3,3,4,4,5,5-octafluoropentyl)malononitrile and 0.70 g of methyl vinyl ketone were dissolved in 15 ml of acetone, 0.83 g of potassium carbonate was added, and the mixture was stirred at room temperature for 4 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.5 g of 2-(2,2,3,3,4,4,5,5-octafluoropentyl)-2-(3-oxobutyl)malononitrile.

2-(2,2,3,3,4,4,5,5-octafluoropentyl)-2-(3-oxobutyl)malononitrile:
$^1$H-NMR(CDCl$_3$, TMS) δ(ppm): 2.26(3H, s), 2.39(2H, t), 2.80(2H, t), 2.94(2H, t), 6.07(1H, tt).

Reference Production Example 17

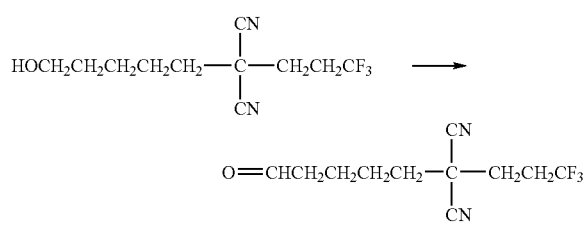

20 ml of a 15% solution of Dess-Martin periodinane=1,1,1-tris(acetyloxy)-1,1-di-hydro-1,2-benziodoxol-3-(1H)-one in dichloromethane was added dropwise to 1.5 g of 2-(5-hydroxypentyl)-2-(3,3,3-trifluoropropyl)malononitrile, and the mixture was stirred at room temperature for 5 hours. Thereafter, the reaction mixture was added to an aqueous dilute sodium hydroxide solution and then extracted with chloroform. The organic layer was washed successively with water and aqueous sodium chloride, dried over anhydrous magnesium sulfate, and then concentrated under reduced pressure. The residue was subjected to silica gel column chromatography to obtain 1.0 g of 2-(5-oxopentyl)-2-(3,3,3-trifluoropropyl)malononitrile.

2-(5-oxopentyl)-2-(3,3,3-trifluoropropyl)malononitrile:
$^1$H-NMR(CDCl$_3$, TMS) δ(ppm): 1.73-1.78(4H, m), 1.99-2.03(2H, m), 2.19-2.23(2H, m), 2.46-2.59(4H, m), 9.81(1H, t).

Reference Production Example 18

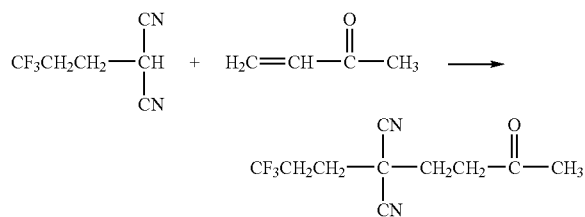

3.2 g of 2-(3,3,3-trifluoropropyl)malononitrile and 2.1 g of methyl vinyl ketone were dissolved in 30 ml of acetone, 3.3 g of potassium carbonate was added, and the mixture was stirred at room temperature for 4 hours. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 0.7 g of 2-(3,3,3-trifluoropropyl)-2-(3-oxobutyl)malononitrile.

2-(3,3,3-trifluoropropyl)-2-(3-oxobutyl)malononitrile:
$^1$H-NMR(CDCl$_3$, TMS) δ(ppm): 2.19-2,30(7H, m), 2.46-2.55(2H, m), 2.84-2.91(2H, m).

Reference Production Example 19

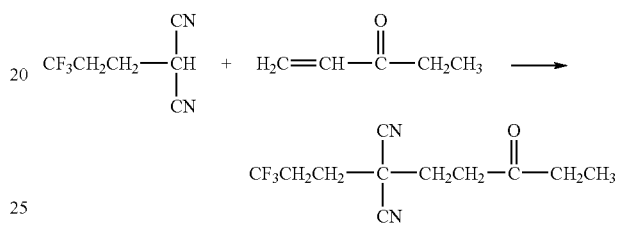

3.2 g of 2-(3,3,3-trifluoropropyl)malononitrile and 1.7 g of ethyl vinyl ketone were dissolved in 30 ml of acetone, 3.3 g of potassium carbonate was added, and the mixture was stirred at room temperature for 1 hour. Thereafter, dilute hydrochloric acid was added to the reaction mixture, followed by extraction with methyl tert-butyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 1.3 g of 2-(3,3,3-trifluoropropyl)-2-(3-oxopentyl)malononitrile.

2-(3,3,3-trifluoropropyl)-2-(3-oxopentyl)malononitrile:
$^1$H-NMR(CDCl$_3$, TMS) δ(ppm): 1.11(3H, t), 2.22-2.26 (2H, m), 2.31(2H, t), 2.46-2.58(4H, m), 2.84(2H, t).

Reference Production Example 20

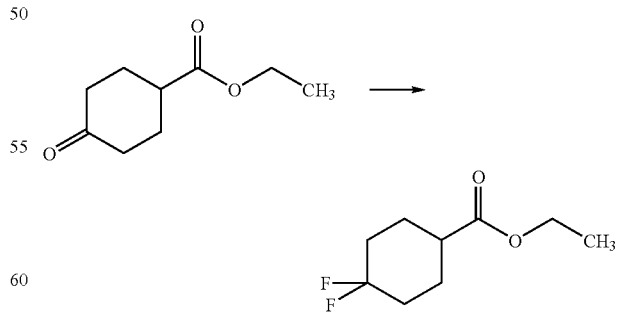

2.5 g of ethyl 4,4-difluorocyclohexanecarboxylate was obtained according to Production Example 60 except that 5.0 g of ethyl 4-oxocyclohexanecarboxylate was used in place of 2-(5-oxopentyl)-2-(3,3,3-trifluoropropyl)malononitrile.

Ethyl 4,4-difluorocyclohexanecarboxylate:

$^1$H-NMR(CDCl$_3$, TMS) δ (ppm): 1.26(3H, t), 1.69-2.16 (8H, m), 2.39(1H, m), 4.15 (2H, q).

Reference Production Example 21

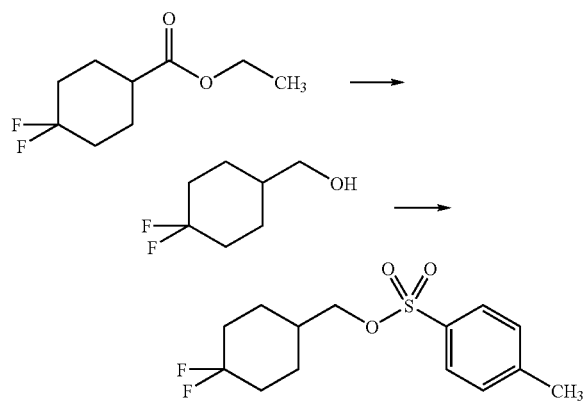

(1) Under nitrogen atmosphere, 2.3 g of ethyl 4,4-difluorocyclohexanecarboxylate was dissolved in 50 ml of tetrahydrofuran. Thereto 0.46 g of lithium aluminum hydride was added at 0° C. and the mixture was stirred at 0° C. for an hour. Thereafter, 1N aqueous sodium hydroxide was added to the reaction mixture, and formed solids were filtered and then washed with ethyl acetate. The filtrate and the washing solution were combined, dried over anhydrous magnesium sulfate, and then concentrated under reduced pressure to obtain (4,4-difluorocyclohexyl)methanol.

(2) The above (4,4-difluorocyclohexyl)methanol was dissolved in 5 ml of pyridine. Thereto 2.2 g of p-toluenesulfonyl chloride was added at 0° C. and the mixture was stirred at room temperature overnight. Thereafter, the reaction mixture was concentrated under reduced pressure. The residue was dissolved in ethyl acetate, washed successively with water, dilute hydrochloric acid and aqueous saturated sodium chloride, dried over anhydrous magnesium sulfate, and then concentrated under reduced pressure. The residue was subjected to silica gel column chromatography to obtain 3.1 g of 4,4-difluorocyclohexylmethyl p-toluenesulfonate.

4,4-Difluorocyclohexylmethyl p-toluenesulfonate:

$^1$H-NMR(CDCl$_3$, TMS) δ (ppm): 1.18-1.37(2H, m), 1.56-1.86(5H, m), 2.00-2.17(2H, br), 2.46(3H, s), 3.86(2H, d), 7.35(2H, d), 7.78 (2H, d).

Reference Production Example 22

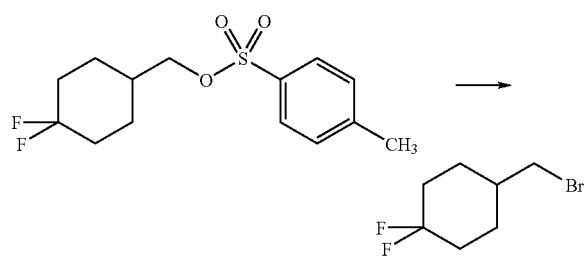

In 15 ml of acetone, 1.5 g of 4,4-difluorocyclohexylmethyl p-toluenesulfonate was dissolved. Thereto 1.6 g of lithium bromide monohydrate was added and the mixture was heated under reflux for 8 hours. After the reaction mixture was cooled to room temperature, water was added and the mixture was extracted with t-butyl methyl ether. The organic layer was washed with aqueous saturated sodium chloride, dried over anhydrous magnesium sulfate, and then concentrated under reduced pressure. The residue was subjected to silica gel column chromatography to obtain 0.76 g of 4-bromomethyl-1,1-difluorocyclohexane.

4-Bromomethyl-1,1-difluorocyclohexane:

$^1$H-NMR(CDCl$_3$, TMS) δ (ppm): 1.33-1.48(2H, m), 1.64-1.84(3H, m), 1.90-2.00(2H, m), 2.14-2.20(2H, m), 3.31(2H, d).

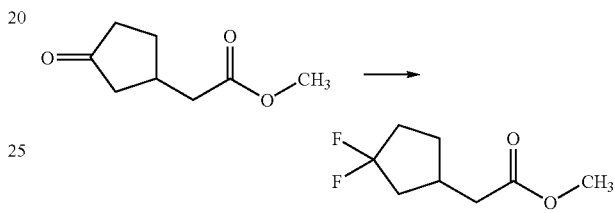

Reference Production Example 23

0.9 g of methyl (3,3-difluorocyclopentyl)acetate was obtained according to Production Example 60 except that 1.8 g of methyl (3-oxocyclopentyl)acetate was used in place of 2-(5-oxopentyl)-2-(3,3,3-trifluoropropyl)malononitrile.

Methyl (3,3-difluorocyclopentyl)acetate:

$^1$H-NMR(CDCl$_3$, TMS) δ (ppm): 1.46(1H, m), 1.75(1H, m), 1.98-2.25(3H, m), 2.29-2.44(3H, m), 2.53(1H, m), 3.68 (3H, s).

Reference Production Example 24

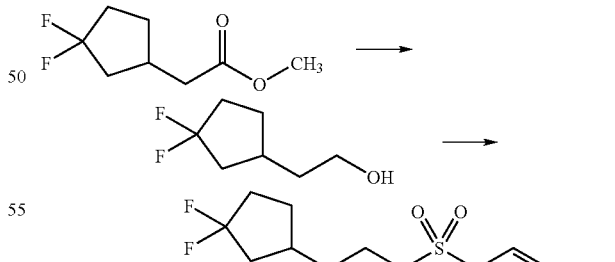

0.68 g of 2-(3,3-difluorocyclopentyl)ethyl p-toluenesulfonate was obtained according to Reference Production Example 21 except that 0.50 g of (3,3-difluorocyclopentyl)acetic acid methyl ester was used in place of ethyl 4,4-difluorocyclohexanecarboxylate.

2-(3,3-Difluorocyclopentyl)ethyl p-toluenesulfonate:

$^1$H-NMR(CDCl$_3$, TMS) δ (ppm): 1.35(1H, m), 1.59(1H, m), 1.70-1.76(2H, m), 1.85-2.24(5H, m), 2.46(3H, s), 3.98-4.08(2H, m), 7.36(2H, d), 7.79(2H, d).

Reference Production Example 25

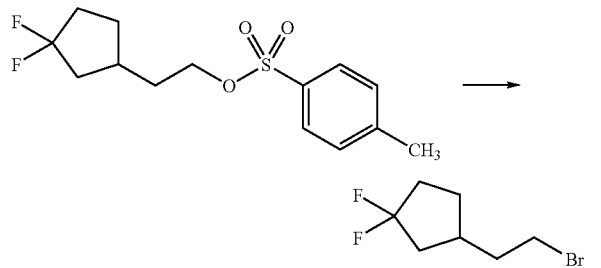

0.17 g of 3-(2-bromoethyl)-1,1-difluorocyclopentane was obtained according to Reference Production Example 22 except that 0.33 g of 2-(3,3-difluorocyclopentyl)ethyl p-toluenesulfonate was used in place of 4,4-difluorocyclohexylmethyl p-toluenesulfonate.

3-(2-Bromoethyl)-1,1-difluorocyclopentane:

$^1$H-NMR(CDCl$_3$, TMS) δ (ppm): 1.42(1H, m), 1.69(1H, m), 1.92-2.39(7H, m), 3.39 (2H, t).

Reference Production Example 26

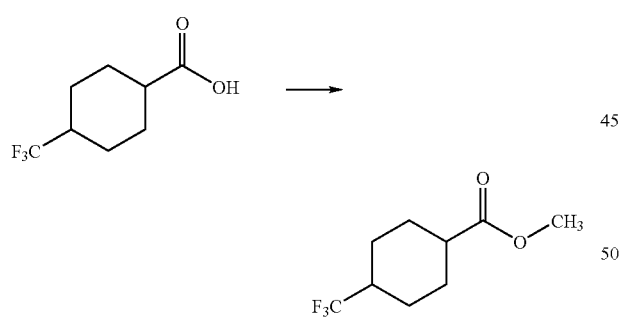

In 25 ml of methanol, 1.0 g of 4-trifluoromethylcyclohexanecarboxylic acid was dissolved. Thereto 50 mg of concentrated hydrochloric acid was added and the mixture was heated under reflux for 10 hours. After the reaction mixture was cooled to room temperature, water was added thereto and the mixture was extracted with t-butyl methyl ether. The organic layer was washed with aqueous saturated sodium chloride, dried over anhydrous magnesium sulfate, and then concentrated under reduced pressure. The residue was subjected to silica gel column chromatography to obtain 0.83 g of methyl 4-trifluoromethylcyclohexanecarboxylate (cis/trans ratio 7/1).

Methyl 4-trifluoromethylcyclohexanecarboxylate (cis/trans ratio=7/1):

$^1$H-NMR(CDCl$_3$, TMS) δ (ppm): 1.23-1.59(3H, m), 1.73-1.84(2H, m), 1.94-2.28(4H, m), 2.66(1H, m), 3.68(0.37H, s), 3.71(2.63H, s).

Reference Production Example 27

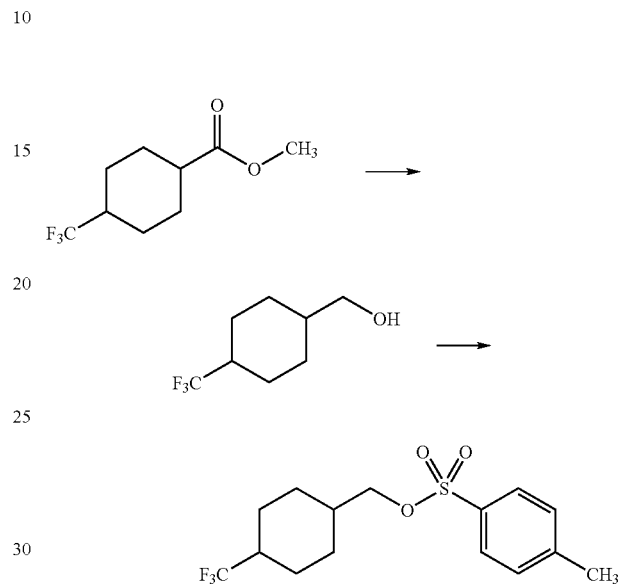

1.2 g of 4-trifluoromethylcyclohexylmethyl p-toluenesulfonate (cis/trans=12/1) was obtained according to Reference Production Example 21 except that 0.83 g of methyl 4-trifluoromethylcyclohexanecarboxylate was used in place of ethyl 4,4-difluorocyclohexanecarboxylate.

4-Trifluoromethylcyclohexylmethyl p-toluenesulfonate (cis/trans=12/1):

$^1$H-NMR(CDCl$_3$, TMS) δ (ppm): 0.91-1.68(7H, m), 1.80-2.11(3H, m), 2.47(3H, s), 3.84(0.15H, d), 3.96(1.85H, d), 7.36(2H, d), 7.76-7.84(2H, m).

Reference Production Example 28

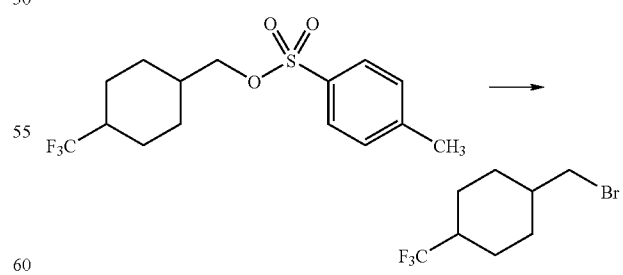

0.31 g of 1-bromomethyl-4-trifluoromethylcyclohexane (cis/trans=10/1) was obtained according to Reference Production Example 22 except that 1.2 g of 4-trifluoromethylcyclohexylmethyl p-toluenesulfonate was used in place of 4,4-difluorocyclohexylmethyl p-toluenesulfonate.

1-Bromomethyl-4-trifluoromethylcyclohexane (cis/trans= 10/1):

¹H-NMR(CDCl₃, TMS) δ (ppm): 1.01-1.82(7H, m), 1.95-2.18(3H, m), 3.30(0.18H, d), 3.41(1.82H, d).

Reference Production Example 29

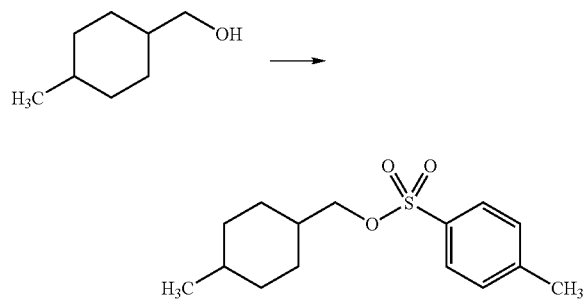

1.6 g of 4-methylcyclohexylmethyl p-toluenesulfonate (cis/trans=5/2) was obtained according to Reference Production Example 21(2) except that 0.85 g of (4-methylcyclohexyl)methanol was used in place of (4,4-difluorocyclohexyl)methanol.

4-Methylcyclohexylmethyl p-toluenesulfonate (cis/trans=5/2):

¹H-NMR(CDCl₃, TMS) δ (ppm): 0.85(0.86H, d), 0.86(2.14H, d), 0.91(1H, m), 1.09-1.21(2H, m), 1.32-1.51 (4H, m), 1.56-1.75(2H, m), 1.85(1H, m), 2.36(0.86H, s), 2.45(2.14H, s), 3.81(0.57H, d), 3.92(1.43H, d), 7.34(2H, d), 7.74-7.83(2H, m).

Reference Production Example 30

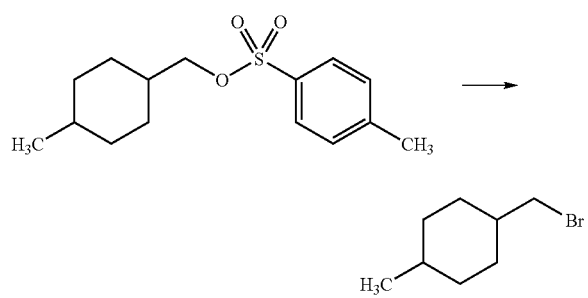

0.29 g of 1-bromomethyl-4-methylcyclohexane (cis/trans=5/2) was obtained according to Reference Production Example 22 except that 1.6 g of p-toluenesulfonic acid 4-methylcyclohexylmethyl ester was used in place of 4,4-difluorocyclohexylmethyl p-toluenesulfonate.

1-Bromomethyl-4-methylcyclohexane (cis/trans=5/2):

¹H-NMR(CDCl₃, TMS) δ (ppm): 0.86-1.09(4H, m), 1.22-1.37(2H, m), 1.43-1.92(7H, m), 3.28(0.57H, d), 3.38(1.43H, d).

Reference Production Example 31

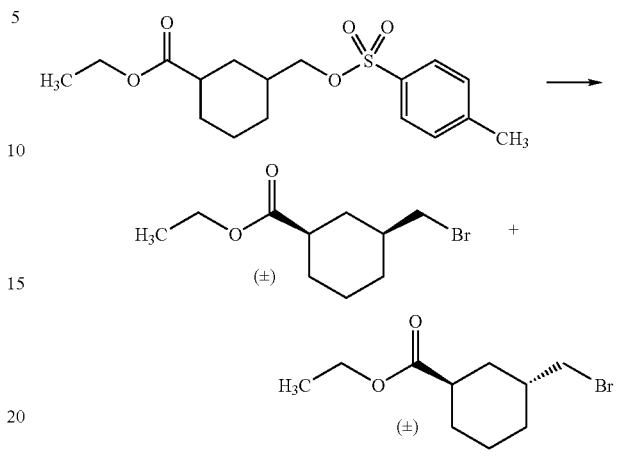

1.9 g of ethyl cis-3-bromomethylcyclohexanecarboxylate and 0.41 g of ethyl trans-3-bromomethylcyclohexanecarboxylate were obtained according to Reference Production Example 22 except that 3.8 g of ethyl 3-(toluene-4-sulfonyloxymethyl)cyclohexanecarboxylate was used in place of 4,4-difluorocyclohexylmethyl p-toluenesulfonate.

Ethyl cis-3-bromomethylcyclohexanecarboxylate:

¹H-NMR(CDCl₃, TMS) δ (ppm): 0.92-1.37(7H, m), 1.69 (1H, m), 1.82-2.00(3H, m), 2.11(1H, br), 2.33(1H, m), 3.30 (2H, d), 4.13(2H, q).

Ethyl trans-3-bromomethylcyclohexanecarboxylate:

¹H-NMR(CDCl₃, TMS) δ (ppm): 1.15-1.64(8H, m), 1.77 (1H, m), 1.90-2.01(2H, m), 2.13(1H, m), 2.66(1H, m), 3.33 (2H, d), 4.15(2H, q).

Reference Production Example 32

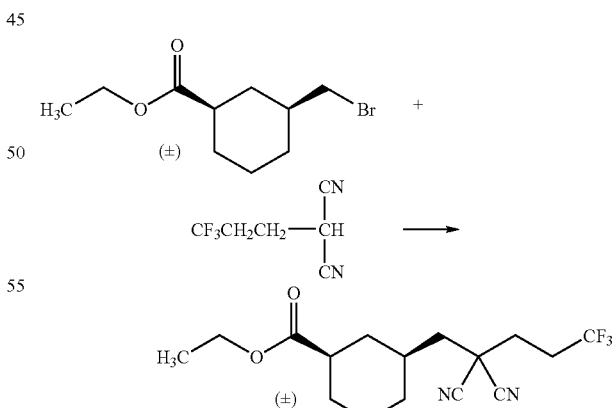

1.1 g of ethyl cis-3-(2,2-dicyano-5,5,5-trifluoropentyl)cyclohexanecarboxylate was obtained according to Production Example 84 except that 1.1 g of ethyl cis-3-bromomethylcyclohexanecarboxylate was used in place of 4-bromomethyl-1,1-difluorocyclohexane.

Ethyl cis-3-(2,2-dicyano-5,5,5-trifluoropentyl)cyclohexanecarboxylate:

$^1$H-NMR(CDCl$_3$, TMS) δ (ppm): 1.08(1H, m), 1.21-1.45 (7H, m), 1.82(1H, m), 1.91(2H, d), 1.99-2.08(2H, br), 2.11-2.24(3H, m), 2.38(1H, m), 2.46-2.60(2H, m), 4.13(2H, q).

Reference Production Example 33

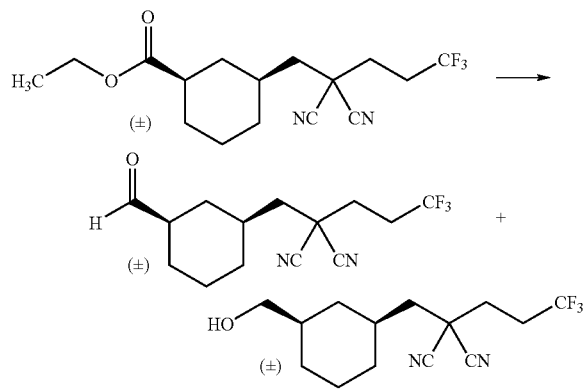

Under nitrogen atmosphere, 1.1 g of ethyl cis-3-(2,2-dicyano-5,5,5-trifluoropentyl)cyclohexanecarboxylate was dissolved in 10 ml of tetrahydrofuran. Thereto 7.0 ml of a solution (0.93 mol/L) of diisobutylaluminum hydride in hexane was added dropwise at −78° C. and the mixture was stirred at −78° C. for 2 hours. The reaction mixture was poured into aqueous saturated sodium chloride and then extracted with t-butyl methyl ether. The organic layer was dried over anhydrous sodium sulfate and then concentrated under reduced pressure. The residue was subjected to silica gel column chromatography to obtain 0.18 g of cis-2-(3-formylcyclohexylmethyl)-2-(3,3,3-trifluoropropyl)malononitrile and 0.32 g of cis-2-(3-hydroxymethylcyclohexylmethyl)-2-(3,3,3-trifluoropropyl)malononitrile.

cis-2-(3-Formylcyclohexylmethyl)-2-(3,3,3-trifluoropropyl)malononitrile:

$^1$H-NMR(CDCl$_3$, TMS) δ (ppm): 1.00-2.10(10H, m), 2.15-2.27(3H, m), 2.34-2.61(3H, m), 9.64 (1H, s).

cis-2-(3-Hydroxymethylcyclohexylmethyl)-2-(3,3,3-trifluoropropyl)malononitrile:

$^1$H-NMR(CDCl$_3$, TMS) δ (ppm): 0.78-1.45(4H, m), 1.61 (1H, m), 1.77-1.92(5H, m), 1.97-2.08(2H, br), 2.17-2.27(2H, m), 2.46-2.60(2H, m), 3.45-3.56(2H, br).

Reference Production Example 34

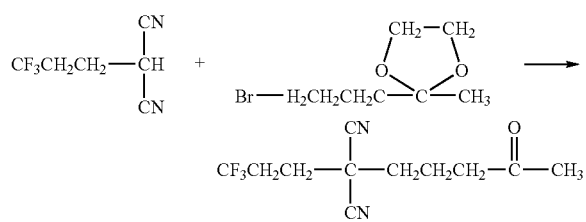

In 30 ml of acetone, 2.7 g of 2-(3,3,3-trifluoropropyl)malononitrile and 3.5 g of 2-(3-bromopropyl)-2-methyl-1,3-dioxolane were dissolved. Thereto 2.3 g of potassium carbonate was added and the mixture was stirred at room temperature for 5 hours. Thereafter, the reaction mixture was added to dilute hydrochloric acid and stirred for an hour. The reaction mixture was extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 1.4 g of a compound represented by the formula:

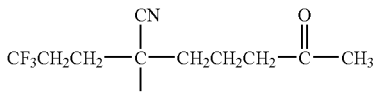

$^1$H-NMR(CDCl$_3$, TMS) δ (ppm): 1.91-1.99(2H, m), 2.01-2.06(2H, m), 2.18(3H, s), 2.20-2.24(2H, m), 2.46-2.57(2H, m), 2.62(2H, t).

Reference Production Example 35

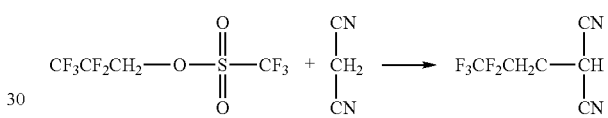

In 30 ml of ethylene glycol dimethyl ether, 8.4 g of 2,2,3,3,3-pentafluoropropyl trifluoromethanesulfonate and 5.9 g of malononitrile were dissolved. Thereto 12.3 g of potassium carbonate was added and the mixture was stirred at room temperature for 8 hours. Thereafter dilute hydrochloric acid was added to the reaction mixture and the mixture was extracted with t-butyl methyl ether. The organic layer was washed successively with water, aqueous saturated sodium hydrogen carbonate and aqueous saturated sodium chloride, dried over anhydrous magnesium sulfate, and then concentrated under reduced pressure. The residue was subjected to silica gel column chromatography to obtain 2.1 g of 2-(2,2,3,3,3-pentafluoropropyl)malononitrile.

2-(2,2,3,3,3-Pentafluoropropyl)malononitrile:

$^1$H-NMR(CDCl$_3$, TMS) δ (ppm): 2.86(2H, dt), 4.14(1H, t).

Then, Formulation Examples will be described. The term "part" represents a part by weight. In addition, the present compound will be designated by the aforementioned compound numbers.

Formulation Example 1

9 Parts of any one of the present compounds (1) to (96) is dissolved in 37.5 pats of xylene and 37.5 parts of N,N-dimethylformamide. Thereto 10 parts of polyoxyethylene styryl phenyl ether and 6 parts of calcium dodecylbenzene sulfonate are added and mixed by stirring thoroughly to obtain an emulsion.

Formulation Example 2

5 Parts of SORPOL 5060 (registered trade name for TOHO Chemical Industry Co., LTD.) is added to 40 parts of any one of the present compounds (1) to (96) and mixed thoroughly. Then, 32 parts of CARPLEX #80 (registered trade name for Shionogi & Co., Ltd., synthetic anhydrous silicon oxide fine powder) and 23 parts of 300 mesh diatomaceous earth are added thereto and mixed with a juice mixer to obtain a wettable preparation.

Formulation Example 3

3 Parts of any one of the present compounds (1) to (96), 5 parts of synthetic hydrous silicon oxide fine powder, 5 parts of sodium dodecylbenzenesulfonate, 3.0 parts of bentonite and 57 parts of clay are mixed by stirring thoroughly. To this mixture an appropriate amount of water is added. The mixture is further stirred, granulated with a granulator, and then air-dried to obtain a granule.

Formulation Example 4

4.5 Parts of any one of the present compounds (1) to (96), 1 part of synthetic hydrous silicon oxide fine powder, 1 part of Dorires B (manufactured by Sankyo) as a flocculant, and 7 parts of clay are mixed thoroughly with a mortar and then by stirring with a juice mixer. To the resultant mixture 86.5 parts of cut clay is added and mixed by stirring thoroughly to obtain a powder.

Formulation Example 5

10 Parts of any one of the present compounds (1) to (96), 35 parts of white carbon containing 50 parts of polyoxyethylene alkylether sulfate ammonium salt, and 55 parts of water are mixed and then finely-divided by a wet grinding method to obtain a preparation.

Formulation Example 6

0.5 Parts of any one of the present compounds (1) to (96) is dissolved in 10 parts of dichloromethane. This solution is mixed with 89.5 parts of Isopar M (isoparaffin: registered trade name for Exxon Chemical) to obtain an oil.

Formulation Example 7

0.1 Parts of any one of the present compounds (1) to (96) and 49.9 parts of NEO-THIOZOL (Chuo Kasei Co., Ltd.) are placed in an aerosol can. An aerosol valve is fitted to the can and the can is then charged with 25 parts of dimethyl ether and 25 parts of LPG. The can is shaken and an actuator is fitted to the can to obtain an oily aerosol.

Formulation Example 8

An aerosol container is charged with 0.6 parts of any one of the present compounds (1) to (96), 0.01 part of BHT, 5 parts of xylene, a mixture of 3.39 parts of a deodorized kerosene and 1 part of an emulsifying agent [Atmos 300 (registered trade name for Atmos Chemical Ltd.)] and 50 parts of distilled water. A valve part is attached to the container and the container is then charged with 40 parts of a propellant (LPG) through the valve under increased pressure to obtain an aqueous aerosol.

Formulation Example 9

Figure 2:
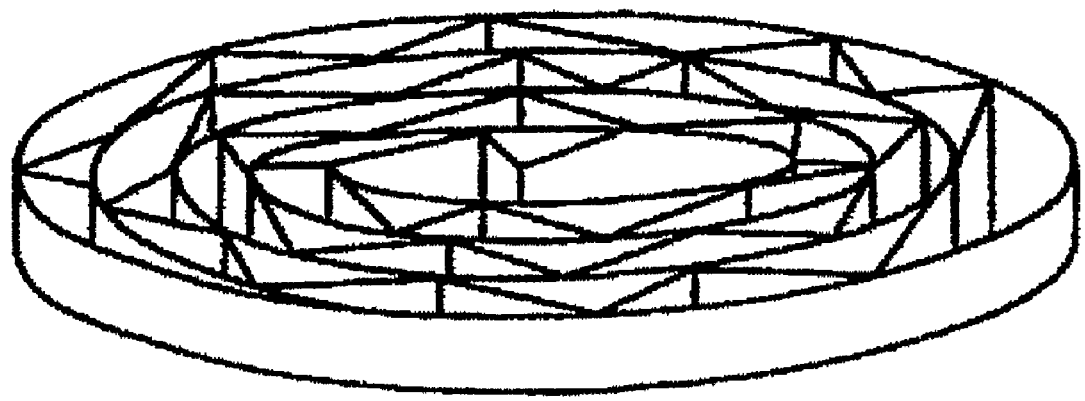
FIG. 2 is a perspective view of a solid carrier used in Formulation Example 9.

A paperware with a honeycomb structure and with 0.5 cm (thickness)×69 cm (length)×0.2 cm (width) is rolled from one end of the paper to make a carrier with a diameter of 5.5 cm and a width of 0.2 cm (see FIG. 1 and FIG. 2). 5 Parts of any one of the present compounds (1) to (96) is dissolved in 95 parts of acetone. An appropriate amount of the resultant solution is applied to said carrier uniformly and acetone is then air-dried to obtain a preparation.

Formulation Example 10

A circle with a diameter of 5 cm is cut out from a three dimensional knitted fabric (trade name: Fusion, type: AKE69440, produced by Asahi Kasei Fibers Corporation, thickness: 4.3 mm, weight: 321 g/m$^2$, made of polyamide). 5 Parts of any one of the present compounds (1) to (96) is dissolved in 95 parts of acetone. An appropriate amount of the solution is applied to said circle of the three dimensional knitted fabric uniformly and acetone is then air-dried to obtain a preparation.

Formulation Example 11

98 Parts by weight of an ethylene-methyl methacrylate copolymer (content of methyl methacrylate: 10% by weight, MFR=2 [g/10 min]) and 2 parts by weight of any one of the present compounds (1) to (96) are melted and kneaded at 130° C. with a 45 mm$\phi$ same directional biaxial extruder and then at 150° C. with a 40 mm$\phi$ extruder, extruded in the sheet form through a T die, and then cooled with a cooling roll to obtain a resin preparation.

Formulation Example 12

98 Parts by weight of an ethylene-vinyl acetate copolymer (content of vinyl acetate: 10% by weight, MFR=2 [g/10 min]) and 2 parts by weight of any one of the present compounds (1) to (96) are melted and kneaded at 13DOC with a 45 mm$\phi$ same directional biaxial extruder and then at 150° C. with a 40 mm$\phi$ extruder, extruded in the sheet from through a T die, and then cooled with a cooling roll to obtain a resin preparation.

Formulation Example 13

Figure 3:
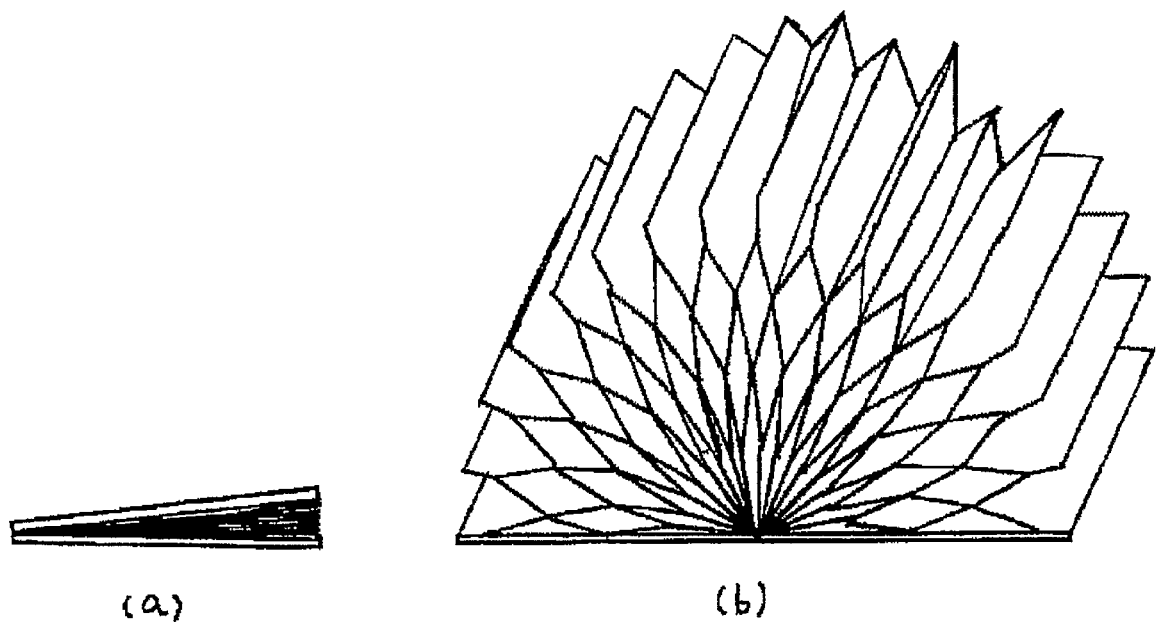
FIG. 3 shows a paper having a foldable structure used in Formulation Example 13. A folded paper (a) is spread out up to 180° with one of planar members as an axis and thereby, for example, one form (b) for use which comprises tubular structures is obtained.

5 Parts of any one of the present compounds (1) to (96) is dissolved in 95 parts of acetone. An appropriate amount of this solution is applied to a paper (2000 cm$^2$) having a foldable structure shown in FIG. 3 and acetone is 5 air-dried to obtain a preparation.

Formulation Example 14

Figure 4:
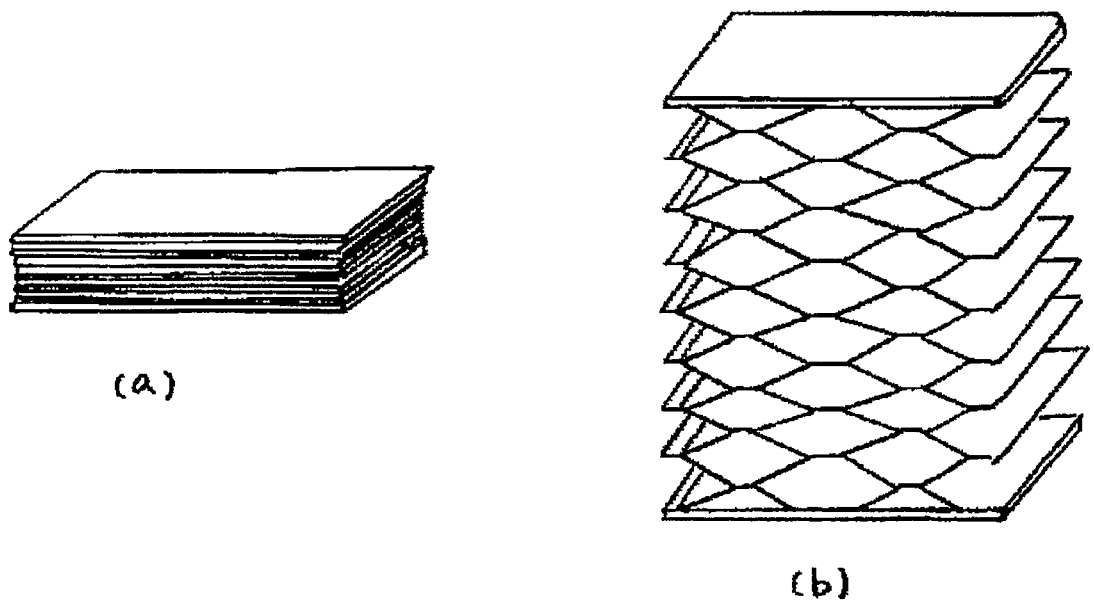
FIG. 4 shows a paper having a foldable structure used in Formulation Example 14. A folded paper (a) is spread by pulling apart planar members facing each other, and thereby one form (b) for use which comprises tubular structures is obtained.

5 Parts of any one of the present compounds (1) to (96) is dissolved in 95 parts of acetone. An appropriate amount of this solution is applied to a paper (2000 cm$^2$) having a foldable structure shown in FIG. 4 and acetone is air-dried to obtain a preparation.

Formulation Example 15

3.6 Parts of any one of the present compounds (1) to (96) and 14.3 parts of acetone are mixed to obtain a solution. To the solution, 0.2 parts of zinc oxide, 1.0 part of α-starch and 42.8 parts of azodicarbonamide are added and 38.1 parts of water is then added. The mixture is kneaded, molded into granules with an extruder, and then dried. The granules containing the present compound are placed in the upper space of a container whose central part is partitioned with an aluminum partition, and 50 g of calcium oxide is placed in the lower space of the container to obtain a smoking preparation.

Formulation Example 16

0.5 Parts of zinc oxide, 2 parts of α-starch and 97.5 parts of azodicarbonamide are mixed and water is added thereto. The mixture is kneaded, molded into granules with an extruder, and then dried to obtain granules. 2 g of the granule is impregnated uniformly with an acetone solution containing 0.58 g of any one of the present compounds (1) to (96) and then dried to obtain granules containing any one of the present compounds (1) to (96). The granules containing the present compound are placed in the upper space of a container whose central part is partitioned with an aluminum partition, and 50 g of calcium oxide is placed in the lower space of the container to obtain a smoking preparation.

Formulation Example 17

0.5 g of any one of the present compounds (1) to (96) is dissolved in 20 ml of acetone and then mixed uniformly together with 99.4 g of a mosquito coil carrier [a mixture of tabu powder (powder of Machilus thunbergii): dregs powder (powder of parts other than the active component of pyrethrum): wood powder at a weight ratio of 4:3:3] and 0.3 g of a green pigment by stirring. Thereto 120 ml of water is added. The mixture is kneaded thoroughly, molded, and then dried to obtain a mosquito coil.

Formulation Example 18

10 Parts of any one of the present compounds (1) to (96), 40 parts of acetyltributyl citrate, 40 parts of isononyl adipate, 5 parts of a blue pigment and 5 parts of a perfume are mixed to obtain a solution. The solution is uniformly impregnated into a base material for an electric mosquito mat (a board obtained by hardening fibrils of a mixture of cotton linters and pulp) having 3.4 cm×2.1 cm and a thickness of 0.22 cm to obtain an electric mosquito mat.

Formulation Example 19

0.1 Parts of any one of the present compounds (1) to (96) is dissolved in 99.9 parts of a deodorized kerosine and the solution is placed in a vinyl chloride container. Into the container, a liquid-absorbing wick (obtained by sintering inorganic powder with a binder) whose upper part can be heated with a heater is inserted to obtain a part of a liquid-absorbing wick-type heat-vaporizing pesticidal product.

Formulation Example 20

0.2 Parts of any one of the present compounds (1) to (96) and 49.8 parts of NEO-THIOZOL (Chuo Kasei Co., Ltd.) are placed in an aerosol can and an aerosol valve is fitted to the can. The can is then charged with 25 parts of dimethyl ether and 25 parts of LPG and is shaken. An actuator for a total amount spraying-type aerosol is fitted to the can obtain an aerosol.

Formulation Example 21

99.8 Parts of diethylene glycol monoethyl ether is added to 0.2 parts of any one of the present compounds (1) to (96) and mixed thoroughly by stirring to obtain a spot-on preparation.

Formulation Example 22

1 mL of a solution of 3.3 parts of any one of the present compounds (1) to (96) and 96.7 parts of acetone is uniformly applied to a disc (diameter: 3 cm, thickness: 3 mm) which is obtained by compressing (4 t/cm$^2$) 4000 mg of 2,4,6-triisopropyl-1,3,5-trioxane, and then is dried to obtain a tablet.

Formulation Example 23

A uniform mixture of 200 mg of any one of the present compounds (1) to (96) and 4000 mg of 2,4,6-triisopropyl-1,3,5-trioxane is compressed (4 t/cm$^2$) into a disc (diameter: 3 cm, thickness: 3 mm) to obtain a tablet.

Formulation Example 24

200 mg of any one of the present compounds (1) to (96) and 4000 mg of 2,4,6-triisopropyl-1,3,5-trioxane are placed in a 50 mL screw tube, melted by heating, and then cooled to room temperature to obtain a tablet.

Then, it will be demonstrated by Experimental Examples that the present compound is effective as the active ingredient of a pesticidal composition. The present compound will be designated by the aforementioned compound numbers.

Experimental Example 1

Preparations of the present compounds (1), (2), (3), (4), (5), (22), (23), (24), (28), (29), (30), (31), (32), (35), (36), (37), (38), (39), (46), (48), (49), (51), (53), (54), (56), (58), (59), (60), (61), (64), (66), (67), (68), (69), (70), (71), (72), (73), (74), (75), (76), (77), (78), (79), (80), (81), (82), (83), (85), (86), (87), (88), and (89) obtained according to Formulation Example 5 were diluted so that the active ingredient concentration was 500 ppm to obtain experimental pesticidal solutions.

At the same time, 50 g of molding Bonsoru 2 (manufactured by Sumitomo Chemical Co., Ltd.) was put into a polyethylene cup, and 10 to 15 seeds of rice were planted therein. The rice plants were grown until the second foliage leaf is developed and then cut into the same height of 5 cm. The experimental pesticidal solution prepared as described above was sprayed in an amount of 20 ml/cup to the rice plants. After the pesticidal solution sprayed onto the rice plants was dried, the rice plants were put into a plastic cup for preventing the escape of test pests. 30 first-instar larvae of *Nilaparvata lugens* were released into the plastic cup and the cup was sealed with a lid and then left in a greenhouse (25° C.). On the sixth day after release of *Nilaparvata lugens* larvae, the number of parasitic *Nilaparvata lugens* on the rice plants was examined.

As a result, on the plants treated with the present compounds (1), (2), (3), (4), (5), (22), (23), (24), (28), (29), (30), (31), (32), (35), (36), (37), (38), (39), (46), (48), (49), (51), (53), (54), (56), (58), (59), (60), (61), (64), (66), (67), (68), (69), (70), (71), (72), (73), (74), (75), (76), (77), (78), (79), (80), (81), (82), (83), (85), (86), (87), (88), and (89), the number of the parasitic pest was 3 or smaller.

Experimental Example 2

Preparations of the present compounds (1), (2), (3), (4), (5), (9), (10), (11), (15), (16), (17), (20), (21), (22), (23), (24), (25), (27), (29), (30), (31), (32), (35), (36), (37), (38), (39), (46), (47), (48), (49), (50), (51), (52), (53), (54), (55), (56), (58), (59), (60), (61), (62), (64), (66), (67), (68), (69), (70), (71), (73), (74), (75), (76), (77), (78), (79), (80), (81), (82), (83), (85), (86), (87), and (89) obtained according to Formulation Example 5 were diluted with water so that the active ingredient concentration was 500 ppm to prepare experimental pesticidal solutions.

A filter paper having a diameter of 5.5 cm was spread on the bottom of a polyethylene cup having a diameter of 5.5 cm and 0.7 ml of the experimental pesticidal solution was added dropwise onto the filter paper. As a bait 30 mg of sucrose was uniformly placed on the filter paper. Into the polyethylene cup, 10 female *Musca domestica* imagoes were released and the cup was sealed with a lid. After 24 hours, the number of surviving *Musca domestica* was examined and the death rate of the pest was calculated.

As a result, in treatments with the present compounds (1), (2), (3), (4), (5), (9), (10), (11), (15), (16), (17), (20), (21), (22), (23), (24), (25), (27), (29), (30), (31), (32), (35), (36), (37), (38), (39), (46), (47), (48), (49), (50), (51), (52), (53), (54), (55), (56), (58), (59), (60), (61), (62), (64), (66), (67), (68), (69), (70), (71), (73), (74), (75), (76), (77), (78), (79), (80), (81), (82), (83) (85), (86), (87), and (89), the death rate of the pest was 90% or more.

Experimental Example 3

Preparations of the present compounds (3), (4), (5), (9), (10), (17), (20), (21), (22), (23), (24), (25), (27), (29), (30), (31), (32), (35), (36), (37), (38), (46), (47), (48), (50), (52), (53), (54), (55), (56), (58), (59), (60), (61), (64), (66), (67), (68), (69), (71), (72), (73), (74), (75), (78), (79), (80), (81), (82), (83), (87), (88), (89), and (93) obtained according to Formulation Example 5 were diluted with water so that the active ingredient concentration was 500 ppm to prepare experimental pesticidal solutions.

A filter paper having a diameter of 5.5 cm was spread on the bottom of a polyethylene cup having a diameter of 5.5 cm and 0.7 ml of the experimental pesticidal solution was added dropwise onto the filter paper. As a bait 30 mg of sucrose was uniformly placed on the filter paper. Into the polyethylene cup, two male *Blattalla germanica* imagoes were released and the cup was sealed with a lid. After 6 days, the number of surviving *Blattalla germanica* was examined and the death rate of the pest was calculated.

As a result, in treatments with the present compounds (3), (4), (5), (9), (10), (17), (20), (21), (22), (23), (24), (25), (27), (29), (30), (31), (32), (35), (36), (37), (38), (46), (47), (48), (50), (52), (53), (54), (55), (56), (58), (59), (60), (61), (64), (66), (67), (68), (69), (71), (72), (73), (74), (75), (78), (79), (80), (81), (82), (83), (87), (88), (89), and (93), the death rate of the pest was 100%.

Experimental Example 4

Preparations of the present compounds (1), (3), (4), (8), (9), (10), (11), (12), (17), (20), (21), (22), (23), (28), (29), (30), (31), (32), (35), (36), (37), (38), (39), (43), (46), (47), (48), (49), (51), (53), (54), (55), (56), (58), (59), (60), (61), (62), (63), (65), (66), (67), (68), (69), (70), (71), (72), (73), (74), (75), (76), (77), (78), (79), (80), (81), (82), (83), (85), (87), (89), and (93) obtained according to Formulation Example 5 were diluted with water so that the active ingredient concentration was 500 ppm to prepare experimental pesticidal solutions.

0.7 ml of the experimental pesticidal solution was added to 100 mL of ion-exchanged water (active ingredient concentration: 3.5 ppm). Into the solution, 20 last-instar larvae of *Culex pipiens pallens* were released. After one day, the surviving number was examined and the death rate of the pest was calculated.

As a result, in treatments with the present compounds (1), (3), (4), (8), (9), (10), (11), (12), (17), (20), (21), (22), (23), (28), (29), (30), (31), (32), (35), (36), (37), (38), (39), (43), (46), (47), (48), (49), (51), (53), (54), (55), (56), (58), (59), (60), (61), (62), (63), (65), (66), (67), (68), (69), (70), (71), (72), (73), (74), (75), (76), (77), (78), (79), (80), (81), (82), (83), (85), (87), (89), and (93), the death rate of the pest was 90% or more.

Experimental Example 5

Acetone solutions containing 0.057% (w/v) of the present compounds (20), (23), (24), (30), (31), (35) and (37) were prepared. On a filter paper having a diameter of 3.8 cm, 0.2 ml of the solution was added dropwise uniformly and air-dried (corresponding to treatment with 100 mg/m² of the present compound). About 20 imagoes of *Ctenocephalised felis* were released into a 200 mL glass bottle. The bottle was sealed with a lid whose inside the filter paper was set. After 24 hours, the number of surviving *Ctenocephalised felis* was examined and the death rate of the pest was calculated.

As a result, in treatments with the present compounds (20), (23), (24), (30), (31), (35) and (37), the death rate of the pest was 80% or more.

Experimental Example 6

Spot-on preparations of the present compounds (23), (24), (30) and (31) were prepared according to Formulation Example 21. Onto the dorsal line skin of a female mouse (body weight about 30 g), 0.1 ml of the spot-on preparation was added dropwise. This mouse was put into a wire bag slightly larger than the size of the mouse so that it could not move about. This mouse was placed in a 900 mL glass bottle in which a filter paper was spread on the bottom, and 20 imagoes of *Ctenocephalised felis* were released into the glass bottle. The upper side of the glass bottle was covered with a nylon net. After 24 hours, the number of surviving *Ctenocephalised felis* was examined and the death rate of the pest was calculated.

As a result, in treatments with the present compounds (23), (24), (30) and (31), the death rate of the pest was 95% or more.

Experimental Example 7

A 0.25% (w/v) solution of the present compound (31) in methanol was prepared. Onto one side of a polypropylene film having 5.7 cm (height)×16.5 cm (width), 0.22 ml of the solution was added dropwise uniformly (except for 5 mm width from the edges of the film) and then air-dried. Thereafter, the film was folded in half widthwise in a way that the side containing the present compound became the inner face of the folded film. Then, the two longer sides (5 mm width each) of the folded film were heat-sealed to obtain a pouch. 10 young mites of *Haemaphysalis longicornis* were put into the polypropylene film pouch. The opening part of the polypropylene film pouch was closed with a clip. After 48 hours, the number of surviving *Haemaphysalis longicornis* was examined and the death rate of the pest was calculated.

As a result, in treatment with the present compound (31), the death rate of the pest was 100%.

Experimental Example 8

A 2% (w/v) solution of the present compound (31) in acetone was prepared. Onto a filter paper with 10 cm×12.5 cm, 2.5 ml of the solution was added dropwise uniformly and then air-dried. This filter paper was suspended from the center of the ceiling of a glass chamber with 70 cm (width)×70 cm (depth)×70 cm (height) and therein 20 imagoes of *Megaselia*

*spiracularis* were released. After 2 hours, all test pests were collected, put in a plastic cup together with absorbent cotton impregnated with 5% sugar water, and then left at 25° C. After 24 hours, the number of surviving *Megaselia spiracularis* was examined and the death rate was calculated.

As a result, in treatment with the present compound (31), the death rate of the pest was 100%.

Experimental Example 9

A 2% (w/v) solution of the present compound (31) in acetone was prepared. Onto a filter paper with 10 cm×12.5 cm, 2.5 ml of the solution was added dropwise uniformly and then air-dried. This filter paper was suspended from the center of the ceiling of a glass chamber with 70 cm (width)×70 cm (depth)×70 cm (height) and therein 20 imagoes of *Clogmia albipunctata* were released. After 2 hours, all test pests were collected, put into a plastic cup together with absorbent cotton impregnated with 5% sugar water, and then left at 25° C. After 24 hours, the number of surviving *Clogmia albipunctata* was examined and the death rate was calculated (2 repetitions).

As a result, in treatment with the present compound (31), the death rate of the pest was 83%.

Experimental Example 10

A 1% (w/v) solution of the present compound (31) in acetone was prepared. Onto a filter paper with 10 cm×25 cm, 5 ml of the solution was added dropwise uniformly and then air-dried. This filter paper was suspended from the center of the ceiling center of a Peet-Grady chamber with 1.8 m (width)×1.8 m (depth)×1.8 m (height) and therein about 50 female imagoes of *Culex pipiens pallens* were released. After 1 hour, all test pests were collected, put into a plastic cup together with absorbent cotton impregnated with 5% sugar water, and then left at 25° C. After 24 hours, the number of surviving *Culex pipiens pallens* was examined and the death rate was calculated.

As a result, in treatment with the present compound (31), the death rate of the pest was 86%.

Experimental Example 11

A 1% (w/v) solution of the present compound (31) in acetone was prepared. Onto a filter paper with 10 cm×25 cm, 5 ml of the solution was added dropwise uniformly and then air-dried. This filter paper was suspended from the center of the ceiling center of a Peet-Grady chamber with 1.8 m (width)×1.8 m (depth)×1.8 m (height) and therein about 50 imagoes of *Musca domestica* were released. After 1 hour, all test pests were collected, put into a plastic cup together with absorbent cotton impregnated with 5% sugar water, and then left at 25° C. After 24 hours, the number of surviving *Musca domestica* was examined and the death rate was calculated.

As a result, in treatment with the present compound (31), the death rate of the pest was 92%.

Experimental Example 12

The present compound (31) was dissolved in a 0.05% (w/v) solution of Sudan red 7B in acetone so that the present compound concentration was 0.005% (w/v) to prepare an experimental pesticidal solution. Onto the notum of the thorax of ergates of *Coptotermes formosanus*, 0.2 μl of this experimental solution was added dropwise. After one day from treatment, the number of surviving pests was examined and the death rate of the pest was calculated.

As a result, in treatment with the present compound (31), the death rate of the pest was 100%.

Experimental Example 13

7.5 mg of the present compound (31) was dissolved in 30 mL of a mixture of 90 parts by weight of Isopar M (isoparaffin, the registered trade name of Exxon Chemical) and 10 parts by weight of dichloromethane to prepare a 0.025% (w/v) oil. A plastic container (diameter: 9.5 cm, height: 4 cm, bottom part of 16 mesh wire) containing 10 imagoes (5 males and 5 females) of *Blattella germanica* was placed on the bottom of a CSMA chamber (width: 46 cm, depth: 46 cm, height: 70 cm).

1.5 ml of the oil was directly sprayed on test cockroaches from the upper side of the CSMA chamber. After 30 seconds from spraying, the container containing cockroaches was removed. All cockroaches were transferred to another clean plastic container (200 mL) and left together with feed and water at 25° C. After 3 days, the number of surviving *Blattella germanica* was examined and the death rate of the pest was calculated.

As a result, in treatment with the present compound (31), the death rate of the pest was 100%.

Experimental Example 14

1% (w/v) solutions of the present compounds (4), (20), (22), (23), (24), (29), (30), (31), (35), (36), (37), (38), (46), (53), (54), (56), (57), (59), (61), (66), (67), (68), (69), (70), (71), (79), (81), (83), (84), (89), and (90) in acetone were prepared. Onto the sternum of the thorax of female imagoes of *Blattella germanica*, 1 μl of the acetone solution was added dropwise. The imagoes were transferred to a plastic cup having a diameter of about 9 cm and a height of about 4.5 cm and left together with feed and water at 25° C. After 7 days, the number of surviving *Blattella germanica* was examined and the death rate of the pest was calculated. 10 imagoes of *Blattella germanica* were put in a cup and three replicate experiments were performed.

As a result, in treatments with the present compounds (4), (20), (22), (23), (24), (29), (30), (31), (35), (36), (37), (38), (46), (53), (54), (56), (57), (59), (61), (66), (67), (68), (69), (70), (71), (79), (81), (83), (84), (89), and (90), the death rate of the pest was 100%.

Experimental Example 15

2.5% (w/v) solutions of the present compounds (23), (24) and (31) in acetone were prepared. 0.1 ml of the solution was added dropwise onto a filter paper with 2 cm×2 cm and then air-dried. This filter paper was attached to the center of the inside bottom of a paper box having 10 cm (width)×2 cm (height)×7 cm (depth) with a two-sided tape. One hole of 5 mm in width and 2 cm in height was made through one side of this box. This box was placed in a plastic vat with 25 cm×20 cm×8 cm in height and therein 10 females and 10 males of *Blattella germanica* were released. The inside wall of the plastic vat used in this experiment was coated with talc for preventing the escape of cockroaches. The plastic vat contained feed and water and left at 25° C. After 7 days, *Blattella germanica* was observed and the death rate of the pest was calculated. This experiment was repeated two times.

As a result, the death rate of the pest was 97.5% in treatment with the present compound (23) and the death rate of the pest was 100% in the treatments with the present compounds (24) and (31).

Experimental Example 16

5% (w/v) solutions of the present compounds (23), (24) and (31) in acetone were prepared. 0.1 ml of the solution was added dropwise onto a filter paper with 2 cm×2 cm and then air-dried. This filter paper was attached to the center of the inside bottom of a paper box having 10 cm (width)×2 cm (height)×7 cm (depth) with a two-sided tape. One hole of 2 mm in width and 2 cm in height was made through one side of this box. This box was placed in a plastic vat with 25 cm×20 cm×8 cm in height and therein 3 females and 3 males of *Periplaneta fuliginosa* were released. The inside wall of the plastic vat used in this experiment was coated with talc for preventing the escape of cockroaches. The plastic vat contained feed and water and left at 25° C. After 7 days, *Periplaneta fuliginosa* was observed and the death rate of the pest was calculated. This experiment was repeated two times.

As a result, the death rate of the pest was 91.7% in treatment with the present compound (23) and the death rate of the pest was 100% in the treatments with the present compounds (24) and (31).

Experimental Example 17

A 5% (w/v) solution of the present compound (31) in acetone was prepared. 0.1 ml of the solution was added dropwise onto a filter paper with 2 cm×2 cm and then air-dried. This filter paper was attached to the center of the inside bottom of a paper box having 10 cm (width)×2 cm (height)×7 cm (depth) with a two-sided tape. One hole of 2 mm in width and 2 cm in height was made through one side of this box. This box was placed in a plastic vat with 25 cm×20 cm×8 cm in height and therein 3 females and 3 males of *Periplaneta americana* were released. The inside wall of the plastic vat used in this experiment was coated with talc for preventing the escape of cockroaches. The plastic vat contained feed and water and left at 25° C. After 7 days, *Periplaneta americana* was observed and the death rate of the pest was calculated. This experiment was repeated two times.

As a result, the death rate of the pest was 100% in treatments with the present compound (31).

Experimental Example 18

Plastic cups (diameter: 12.5 cm, height: 8 cm) containing 10 (5 males and 5 females) imagoes of *Blattella germanica* were placed at the two corners of a Peet-Grady chamber with 1.8 m (width)×1.8 m (depth)×1.8 m (height). A plastic container containing water was placed at the center of the bottom of the Peet-Grady chamber and a smoking preparation of the present compound (31) prepared according to Formulation Example 16 was placed in this plastic cup. After 2 hours, *Blattella germanica* was collected, transferred to a 200 mL plastic cup, and left together with feed and water at 25° C. After 72 hours, the number of surviving *Blattella germanica* was examined and the death rate of the pest was calculated.

As a result, the death rate of the pest was 100% in treatment with the present compound (31).

Experimental Example 19

18.8 mg of the present compound (31) was dissolved in 30 mL of a mixed solvent of 90 parts by weight of Isopar M (isoparaffin, the registered trade name of Exxon Chemical) and 10 parts by weight of dichloromethane to prepare a 0.0625% (w/v) oil. A plastic cup (200 mL) containing 10 imagoes of *Formica fusca japonica* was placed on the bottom of a CSMA chamber (width: 46 cm, depth: 46 cm, height: 70 cm). 0.4 ml of the oil was directly sprayed on the test *Formica fusca japonica* from the upper side of the CSMA chamber. After 10 seconds from spraying, the container containing *Formica fusca japonica* was removed. *Formica fusca japonica* was transferred to another plastic container (200 mL) and left together with feed and water at 25° C. After 72 hours from pesticide treatment, *Formica fusca japonica* was observed and the death rate of the pest was calculated.

As a result, the death rate of the pest was 100% in treatment with the present compound (31).

Experimental Example 20

1 ml of a 0.1% by weight solution of the present compound (31) in acetone was added dropwise to 1 g of a commercially available powdery unrefined sugar, mixed thoroughly and then air-dried to obtain a poison bait. A cotton ball impregnated with water and 0.5 g of the poison bait on an aluminum dish were placed in a plastic cup (860 mL) containing 10 imagoes of *Formica fusca japonica*. After 48 hours, the number of surviving *Formica fusca japonica* was examined and the death rate of the pest was calculated.

As a result, the death rate of Formica fusca japonica was 100% in this experiment.

Experimental Example 21

3 ml of a 0.5% by weight solution of the present compound (31) in acetone is added dropwise to 3 g of animal powdery feed, mixed thoroughly, and then air-dried to obtain a poison bait. 1 g of this poison bait is placed on an aluminum dish and the dish is placed in a plastic cup (860 mL) containing 20 imagoes (10 males and 10 females) of *Blattella germanica*. The pest is given water and kept at 25° C. After 7 days, the number of surviving *Blattella germanica* is examined and the activity of the poison bait is obtained. The poison bait containing the present compound (31) exhibits sufficient pesticidal effect on *Blattella germanica*.

Experimental Example 22

A 10% (w/v) solution of the present compound (31) in acetone is prepared. 10 mL of the solution is uniformly added dropwise to a filter paper with 10 cm×25 cm and then air-dried. The filter paper is suspended from the center of the ceiling of a chamber with 70 cm (width)×70 cm (depth)×70 cm (height). After 20 imagoes (10 males and 10 females) of *Blattella germanica* are released, the door of the chamber is closed. Feed and water are placed in the glass chamber. After 72 hours, the number of surviving *Blattella germanica* is examined and the pesticidal effect on *Blattella germanica* is confirmed.

Experimental Example 23

A 5% (w/v) solution of the present compound (31) in acetone is prepared. 0.1 ml of the solution is added dropwise to a filter paper with 2 cm×2 cm and then air-dried. 10 imagoes of *Formica fusca japonica* are released in a plastic cup having a diameter of 12.5 cm and a height of 8 cm. After feed and water are placed therein, the cup is closed with a lid. The aforementioned pesticide-treated filter paper is attached to the inner surface of the lid. In addition, the inside wall of the cup is coated with talc for preventing the climbing of ants. This cup is kept at 25° C. After 7 days, surviving of *Formica*

75

*fusca japonica* is observed and the pesticidal effect on *Formica fusca japonica* is confirmed.

Experimental Example 24

1.5 g of the present compound (31) is dissolved in 30 mL of a mixed solvent of 90 parts by weight of Isopar M (isoparaffin; the registered trade name of Exxon Chemical) and 10 parts by weight of dichloromethane to prepare a 5% (w/v) oil. A plastic cup (860 mL) containing 10 imagoes of *Halyomorpha mista* is covered with a nylon net (mesh width: 2 mm) and then placed on the bottom of a CSMA chamber (width: 46 cm, depth: 46 cm, height: 70 cm). 0.4 ml of the oil is directly sprayed on the test *Halyomorpha mista* from the upper side of the CSMA chamber. After 10 seconds from spraying, the cup containing *Halyomorpha mista* is removed, and feed and water are placed in the cup. After 72 hours from pesticide treatment, *Halyomorpha mista* is observed and the pesticidal effect on *Halyomorpha mista* is confirmed.

Experimental Example 25

An electric mosquito mat of the present compound (31) prepared according to Formulation Example 18 is set on a heater for an electric mosquito mat and then placed on the centre of the floor of a chamber having 70 cm (width)×70 cm (depth)×70 cm (height). After the electric mosquito mat is initiated to be heated with the heater, about 20 female imagoes of *Culex pipiens pallens* are released in the chamber. After 20 minutes, all test pests are collected, placed in a plastic cup together with absorbent cotton impregnated with 5% sugar water, and left at 25° C. After 24 hours, the number of surviving *Culex pipiens pallens* is examined and then the pesticidal effect on *Culex pipiens pallens* is confirmed.

Experimental Example 26

A part of a liquid-absorbing wick-type heat-vaporizing pesticidal product of the present compound (31) prepared according to Formulation Example 19 is set on a heater for a liquid absorbing wick-type heat-vaporizing pesticide, and then placed on the center of the floor of a chamber having 70 cm (width)×70 cm (depth)×70 cm (height). After the part of a liquid-absorbing wick-type heat-vaporizing pesticidal product is initiated to be heated with the heater, about 20 female imagoes of *Culex pipiens pallens* are released in the chamber. After 20 minutes, all test pests are collected, placed in a plastic cup together with absorbent cotton impregnated with 5% sugar water, and left at 25° C. After 24 hours, the number of surviving *Culex pipiens pallens* is examined and then the pesticidal effect on *Culex pipiens pallens* is confirmed.

Experimental Example 27

Figure 5:
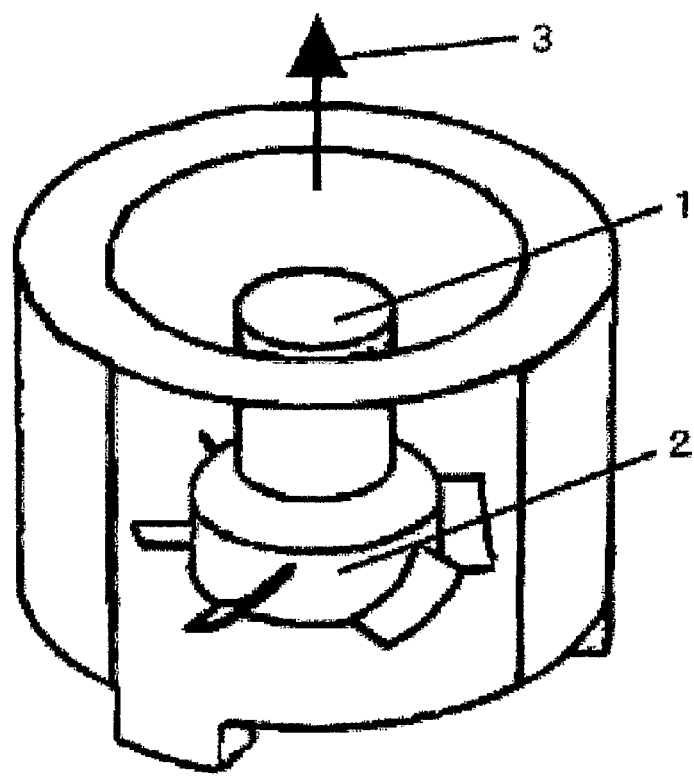
FIG. 5 is a perspective view of a plastic cylinder used in Formulation Example 21, which has a height of 7 cm and a diameter of 8.3 cm and is equipped with an electric fan at the bottom thereof. The numbers mean as follows; 1: a motor; 2: a fan; 3: the flow direction of air.
Figure 6:
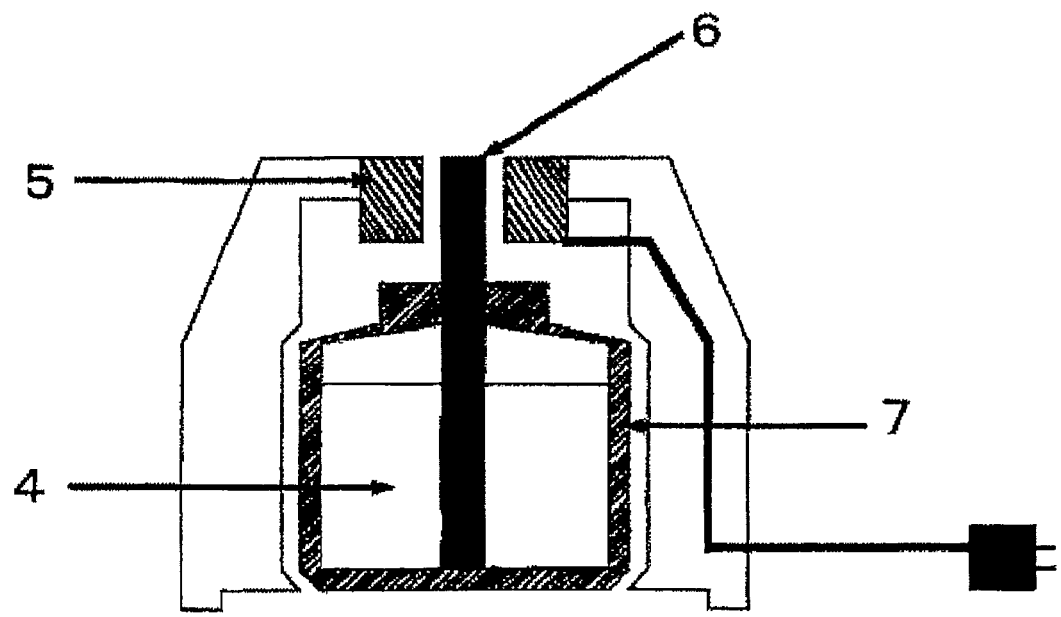
FIG. 6 shows an insecticidal device used in Experimental Example 26. The numbers mean as follows; 4: pesticidal liquid for heat volatilization; 5: a heating element; 6: a wick absorbing liquid; 7: a container containing pesticidal liquid.

A preparation of the present compound (31) prepared according to Formulation Example 10 is set at the upper part of an electric fun shown in FIG. 5 and then placed on the center of the floor of a chamber having 70 cm (width)×70 cm (depth)×70 cm (height). After the electric fan is operated to initiate to ventilate the preparation, about 20 female imagoes of *Culex pipiens pallens* are released in the chamber. After 20 minutes, all test pests are collected, placed in a plastic cup together with absorbent cotton impregnated with 5% sugar water, and left at 25° C. After 24 hours, the number of surviving *Culex pipiens pallens* is examined and then the pesticidal effect on *Culex pipiens pallens* is confirmed.

INDUSTRIAL APPLICABILITY

According to the present invention, pests such as insects, mites and nematodes can be effectively controlled.

The invention claimed is:
1. A nitrile compound represented by the formula (I):

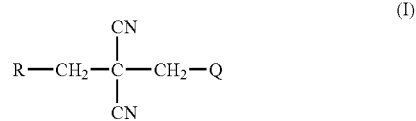

wherein R represents C1-C4 fluoroalkyl,
Q represents C1-C11 alkyl optionally substituted with one or more halogen, C2-C6 alkenyl optionally substituted with one or more halogen, or C2-C6 alkynyl optionally substituted with one or more halogen.

2. The nitrile compound according to claim 1, wherein Q is C1-C6 alkyl optionally substituted with one or more halogen, C2-C6 alkenyl optionally substituted with one or more halogen, or C2-C6 alkynyl optionally substituted with one or more halogen.

3. The nitrile compound according to claim 1, wherein R is C2-C4 fluoroalkyl having 3 to 5 fluorine atoms.

4. The nitrile compound according to claim 1, wherein R is C3-C4 fluoroalkyl group having 6 to 8 fluorine atoms.

5. The nitrile compound according to claim 1, wherein R is C2 fluoroalkyl.

6. The nitrile compound according to claim 1, wherein R is 2,2,2-trifluoroethyl.

7. The nitrile compound according to claim 1, wherein Q is C4-C6 alkyl optionally substituted with one or more halogen.

8. The nitrile compound according to claim 1, wherein Q is C3-C4 alkyl optionally substituted with one or more halogen.

9. The nitrile compound according to claim 1, wherein Q is C4 alkyl group optionally substituted with one or more halogen.

10. The nitrile compound according to claim 1, wherein Q is 1,1,2,2,3,3,4,4-octafluorobutyl.

11. A pesticidal composition comprising the nitrile compound as defined in claim 1 and an inert carrier.

12. A method of controlling a pest, which comprises applying an effective amount of the nitrile compound as defined in claim 1 to said pest or a place where said pest inhabits.

13. The nitrile compound according to claim 2, wherein Q is C4-C6 alkyl optionally substituted with one or more halogen.

14. The nitrile compound according to claim 3, wherein Q is C4-C6 alkyl optionally substituted with one or more halogen.

15. The nitrile compound according to claim 4, wherein Q is C4-C6 alkyl optionally substituted with one or more halogen.

16. The nitrile compound according to claim 5, wherein Q is C4-C6 alkyl optionally substituted with one or more halogen.

17. The nitrile compound according to claim 6, wherein Q is C4-C6 alkyl optionally substituted with one or more halogen.

18. The nitrile compound according to claim 2, wherein Q is C3-C4 alkyl optionally substituted with one or more halogen.

19. The nitrile compound according to claim 3, wherein Q is C3-C4 alkyl optionally substituted with one or more halogen.

20. The nitrile compound according to claim 4, wherein Q is C3-C4 alkyl optionally substituted with one or more halogen.

21. The nitrile compound according to claim 5, wherein Q is C3-C4 alkyl optionally substituted with one or more halogen.

22. The nitrile compound according to claim 6, wherein Q is C3-C4 alkyl optionally substituted with one or more halogen.

23. The nitrile compound according to claim 2, wherein Q is C4 alkyl group optionally substituted with one or more halogen.

24. The nitrile compound according to claim 3, wherein Q is C4 alkyl group optionally substituted with one or more halogen.

25. The nitrile compound according to claim 4, wherein Q is C4 alkyl group optionally substituted with one or more halogen.

26. The nitrile compound according to claim 5, wherein Q is C4 alkyl group optionally substituted with one or more halogen.

27. The nitrile compound according to claim 6, wherein Q is C4 alkyl group optionally substituted with one or more halogen.

28. The nitrile compound according to claim 2, wherein Q is 1,1,2,2,3,3,4,4-octafluorobutyl.

29. The nitrile compound according to claim 3, wherein Q is 1,1,2,2,3,3,4,4-octafluorobutyl.

30. The nitrile compound according to claim 4, wherein Q is 1,1,2,2,3,3,4,4-octafluorobutyl.

31. The nitrile compound according to claim 5, wherein Q is 1,1,2,2,3,3,4,4-octafluorobutyl.

32. The nitrile compound according to claim 6, wherein Q is 1,1,2,2,3,3,4,4-octafluorobutyl.

33. The nitrile compound according to claim 1, wherein Q is C1-C6 alkyl optionally substituted with one or more halogen, C2-C6 alkenyl optionally substituted with one or more halogen, or C2-C6 alkynyl optionally substituted with one or more halogen.

* * * * *

UNITED STATES PATENT AND TRADEMARK OFFICE
CERTIFICATE OF CORRECTION

PATENT NO. : 7,662,402 B2
APPLICATION NO. : 10/584402
DATED : February 16, 2010
INVENTOR(S) : Oohira et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 677 days.

Signed and Sealed this

Twenty-eighth Day of December, 2010

David J. Kappos
*Director of the United States Patent and Trademark Office*